US009809640B2

(12) United States Patent
Vitek et al.

(10) Patent No.: US 9,809,640 B2
(45) Date of Patent: *Nov. 7, 2017

(54) APOE PEPTIDE DIMERS AND USES THEREOF

(71) Applicant: COGNOSCI, INC., Research Triangle Park, NC (US)

(72) Inventors: Michael P. Vitek, Research Triangle Park, NC (US); Dale J. Christensen, Research Triangle Park, NC (US)

(73) Assignee: Cognosci, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/875,919

(22) Filed: Oct. 6, 2015

(65) Prior Publication Data

US 2016/0096877 A1 Apr. 7, 2016

Related U.S. Application Data

(63) Continuation of application No. 13/520,623, filed as application No. PCT/US2011/020393 on Jan. 6, 2011, now abandoned.

(60) Provisional application No. 61/292,668, filed on Jan. 6, 2010.

(51) Int. Cl.
*C07K 14/775* (2006.01)
*A61K 38/17* (2006.01)
*A61K 47/48* (2006.01)
*A61K 38/00* (2006.01)

(52) U.S. Cl.
CPC ........ *C07K 14/775* (2013.01); *A61K 38/1709* (2013.01); *A61K 47/48246* (2013.01); *A61K 38/00* (2013.01)

(58) Field of Classification Search
CPC ................ A61K 38/00; A61K 38/1709; A61K 47/48246; C07K 14/775
See application file for complete search history.

(56) References Cited

U.S. PATENT DOCUMENTS

| | | | |
|---|---|---|---|
| 4,493,795 | A | 1/1985 | Nestor et al. |
| 5,990,088 | A | 11/1999 | Ensoli et al. |
| 6,652,860 | B1 | 11/2003 | Singh et al. |
| 2002/0151004 | A1 | 10/2002 | Craig |
| 2003/0077641 | A1 | 4/2003 | Laskowitz et al. |
| 2003/0125242 | A1 | 7/2003 | Rosenecker et al. |
| 2006/0199778 | A1 | 9/2006 | Ellis-Behnke et al. |
| 2007/0110770 | A1 | 5/2007 | van den Elzen et al. |
| 2007/0224201 | A1 | 9/2007 | Wu et al. |
| 2009/0131315 | A1 | 5/2009 | Vitek et al. |
| 2009/0185997 | A1 | 7/2009 | Laskowitz et al. |
| 2011/0166079 | A1 | 7/2011 | Vitek et al. |
| 2013/0005645 | A1 | 1/2013 | Vitek et al. |
| 2016/0008424 | A1 | 1/2016 | Vitek et al. |

FOREIGN PATENT DOCUMENTS

| | | | |
|---|---|---|---|
| JP | H08-502730 A | 3/1996 | |
| JP | 2006-516089 | 6/2006 | |
| WO | WO 1992/010512 A1 | 6/1992 | |
| WO | WO 1994/004178 A1 | 3/1994 | |
| WO | WO 2006/029028 A2 | 3/2006 | |
| WO | WO 2008080082 A2 * | 7/2008 | ......... A61K 38/1709 |
| WO | WO 2011/085110 A1 | 7/2011 | |

OTHER PUBLICATIONS

"Designing Custom Peptides", SIGMA Genosys (2004), pp. 1-2.
Aleshkov et al., "Contribution of cysteine 158, the glycosylation site threonine 194, the amino-and carboxy-terminal domains of apolipoprotein E in the binding to amyloid peptide beta (1-40)", Biochemistry (1999), 38(28): 8918-8925.
Berendsen, "A Glimpse of the Holly Grail?", Science (1998), 282(5389): 642-643.
Bradley et al., "Limits of Cooperativity in a Structurally Modular Protein: Response of the Notch Ankyrin Domain to Analogous Alanine Substitut⁻ons in Each Repeat", J. Mol. Biol. (2002), 324: 373-386.
Browning et al., "Apolipoprotein E (ApoE), a Novel Heparin-binding Protein Inhibits the Development of Kaposi's Sarcoma-like Lesions in BALB/c nu/nu Mice," Journal of Experimental Medicine (1994), 180: 1949-1954.
Chen, L.L. et al., "Production of multimeric forms of CD4 through a sugar-based cross-linking strategy", The Journal of Biological Chemistry (1991), 266(27): 18237-18243.
Christensen et al., "PP2A activation as a strategy for treatment of breast cancer", Cancer Research Meeting Abstract (2011), vol. 71, Issue 8, XP002714899.
Christensen et al., "SET oncoprotein overexpression in B-cell chronic lymphocytic leukemia and non-Hodgkin lymphoma: a predictor of aggressive disease and a new treatment target.", Blood (2011), 118(15): 4150-4158.
Christensen et al., "Targeting Destruction of Mcl-1 by Activation of Protein Phosphatase 2A in CLL and B-Cell Lymphomas", Blood (2010), 116(21): 1703-1704.
Christensen et al., "The SET Oncogene, a Potent PP2A Inhibitor, Is Elevated in CLL and Antagonism of SET Induces Apoptosis", Blood (2009), 14(22): 331.
European Patent Application No. 11732150.5, Extended European Search Report dated Oct. 30, 2013.

(Continued)

*Primary Examiner* — Hasan Ahmed
*Assistant Examiner* — Erinne Dabkowski
(74) *Attorney, Agent, or Firm* — Cooley LLP

(57) ABSTRACT

The present invention provides novel pharmaceutical compositions comprising ApoE-derived peptide dimers. In particular, the ApoE peptide dimers of the invention comprise at least two ApoE mimetic domains and can comprise one or more protein transduction domains. Methods of treating various conditions, such as cancer, inflammatory conditions, and neurodegenerative diseases, by administering the pharmaceutical compositions of the invention are also disclosed.

14 Claims, 32 Drawing Sheets

(56) References Cited

OTHER PUBLICATIONS

Green, et al., "Quantitative evaluation of the lengths of homobifunctional protein cross-linking reagents used as molecular rulers", Protein Science (2001), 10: 1293-1304.
Keegan et al., "Isolation of an additional member of the fibroblast growth factor receptor family, FGFR-3", Proc. Natl. Acad. Sci. USA (1991), 88: 1095-1099.
Kojima et al., "Anti-tumor Activity of an Antibiotic Peptide Derived from Apoprotein E", in vivo (2005), 19: 261-264.
Konig et al., "Basic fibroblast growth factor (bFGF) upregulates the expression of bcl-2 in B cell chronic lymphocytic leukemia cell lines resulting in delaying apoptosis", Leukemia (1997), 11: 258-265.
Laffont et al., "Apolipoprotein E Activates Akt Pathway in Neuro-2a in an Isoform-Specific Manner", Biochemical and Biophysical Research Communications (2002), 292: 83-87.
Li et al., "Apolipoprotein E derived peptides ameliorate clinical disability and inflammatory infiltrates into the spinal cord in a murine model of multiple sclerosis," Journal of Pharmacology and Experimental Therapeutics (2006), 318(3): 956-965.
Ngo et al., "Computational Complexity, Protein Structure Prediction, and the Levinthal Paradox", The Protein Folding Problem and Tertiary Structure Prediction, (1994), Chapter 14, pp. 491-494.
PCT/US2011/020393, International Search Report and Written Opinion, dated Jun. 1, 2011.
PCT/US2011/020393, International Preliminary Report on Patentability, dated Jul. 10, 2012.
Pegahi et al., "Spontaneous and cytokine-evoked production of matrix metalloproteinases by bone marrow and peripheral blood pre-B cells in childhood acute lymphoblastic leukaemia," Eur. Cytokine Netw. (2005), 16(3): 223-232.
Pierce, Crosslinking Reagents Technical Handbook, pp. 19 and Appendix I, 2006.
Price et al., "Tumorigenicity and Metastasis of Human Breast Carcinoma Cell Lines in Nude Mice," Cancer Research (1990), 50: 717-721.
Rait et al., "Inhibitory effects of the combination of HER-2 antisense oligonucleotide and chemotherapeutic agents used for the treatment of human breast cancer," Cancer Gene Therapy (2001), 8: 728-739.
Rudinger, "Characteristics of the Amino Acids as Components of a Peptide Hormone Sequence", Peptide Hormones, JA Parsons, Ed. (1976), pp. 1-7.
Singh, K., "The Apolipoprotein E-mimetic Peptide COG112 Inhibits the Inflammatory Response to Citrobacter rodentium in Colonic Epithelial Cells by Preventing NF-kB Activation", The Journal of Biological Chemistry (2008), 283: 16752-16761.
Vagner et al., "Peptidomimetics, a synthetic tool of drug discovery", Curr Opin Chem Biol. (2008), 12(3): 292-296.
Voet et al., "Abnormal hemoglobins", Biochemistry (1995), Second Edition, John Wiley & Sons Inc., pp. 235-241.
Vogel et al., "Apolipoprotein E: A Potent Inhibitor of Endothelial and Tumor Cell Proliferation," Journal of Cellular Biochemistry (1994), 54: 299-308.
Wang et al., "Antisense targeting of basic fibroblast growth factor and fibroblast growth factor receptor-1 in human melanomas blocks intratumoral angiogenesis and tumor growth," Nature Medicine (1997), 3: 887-893.
Weisgraber et al., "Identification of the disulfide-linked homodimer of apolipoprotein E3 in plasma. Impact on receptor binding activity", The Journal of Biological Chemistry (1991), 266(18): 12029-12034.
Yamauchi et al., "Role of the N- and C-terminal domains in binding of apolipoprotein E isoforms to heparan sulfate and dermatan sulfate: a surface plasmon resonance study", Biochemistry (2008), 47(25): 6702-6710.
Chen, Yu-Chi, et al. "Apolipoprotein E is required for cell proliferation and survival in ovarian cancer." Cancer Research (2005); 65.1: 331-337.
Mechanisms of Carcinogenesis, 2010, International Agency for Research on Cancer, Section 3, p. 190, col. 1, first paragraph, 37 pages.
Sakashita, Katsuya, et al. "Clinical significance of ApoE expression in human gastric cancer." Oncology Reports (2008); 20.6: 1313-1319.

* cited by examiner

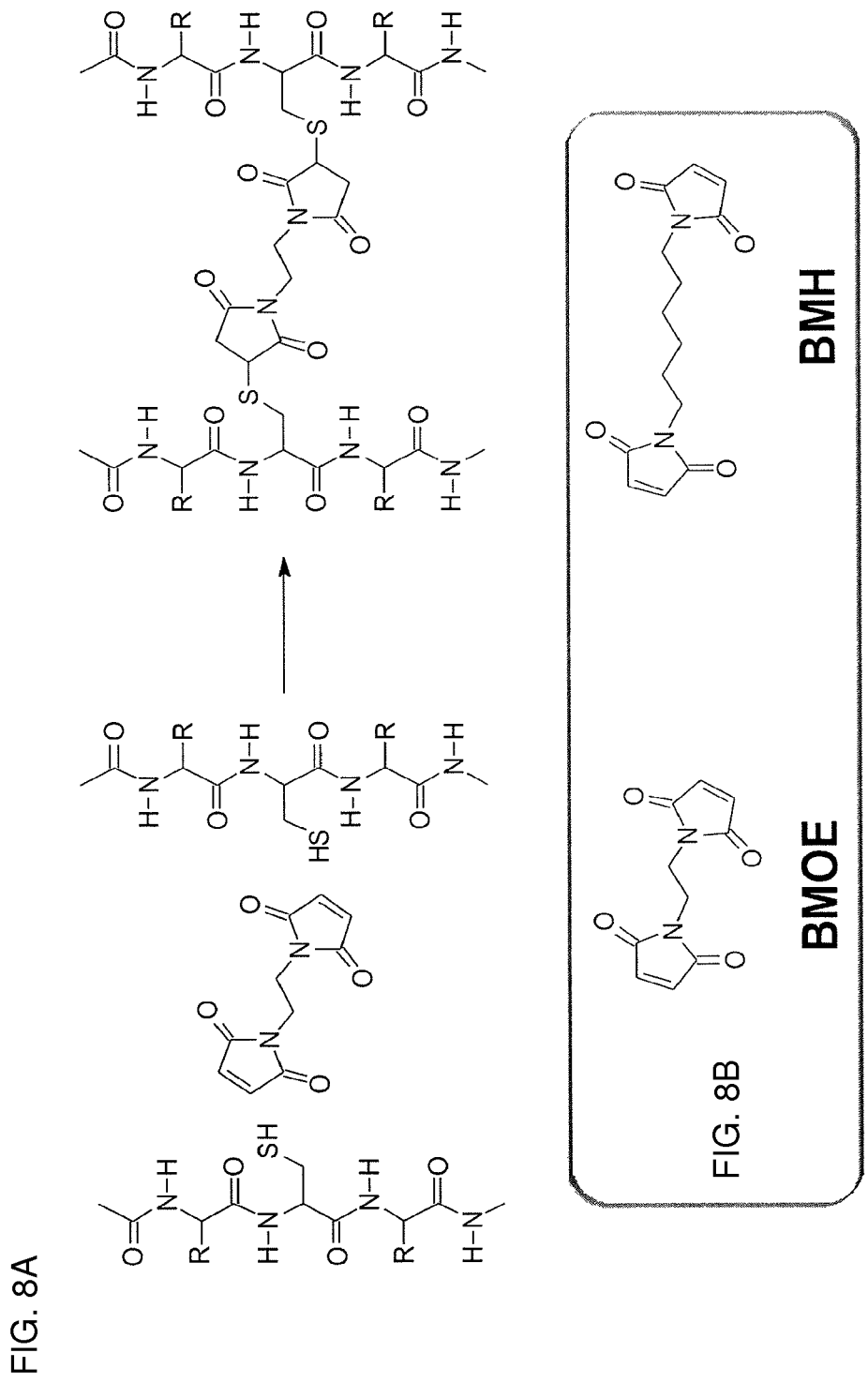

FIG. 10A
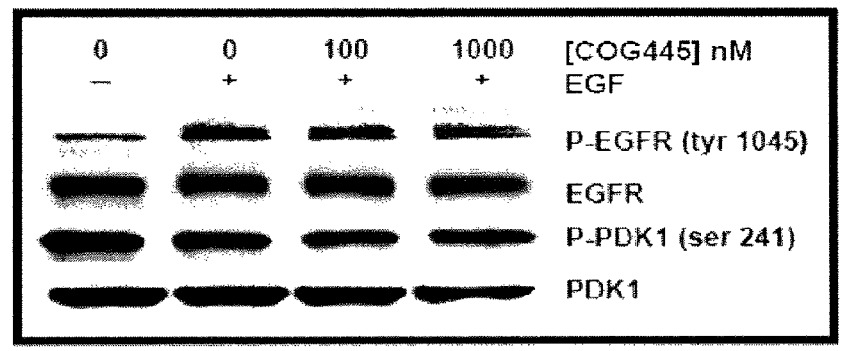
FIG. 10B COG445 Inhibits EGF-induced Akt Activation
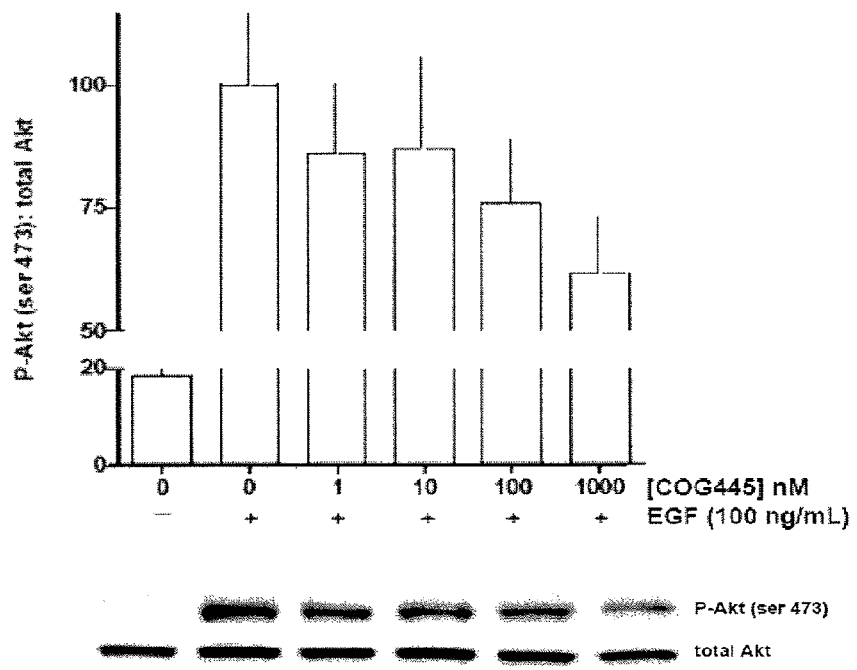

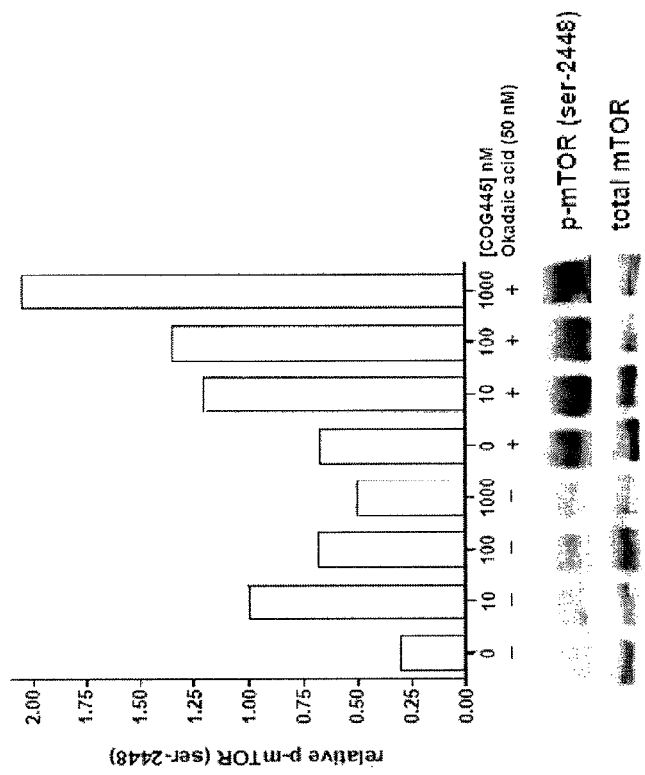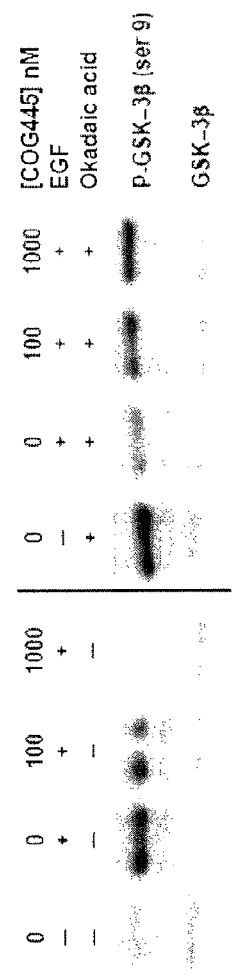
FIG. 13A
FIG. 13B c-Myc: 58-TPPLSP-63 (SEQ ID NO: 89)

Mcl-1: 159-SLPSTP-164 (SEQ ID NO: 89)

APOE PEPTIDE DIMERS AND USES THEREOF

CROSS-REFERENCE TO RELATED APPLICATIONS

This application is a continuation of U.S. application Ser. No. 13/520,623, filed Sep. 17, 2012, which is a national stage application of PCT/US2011/020393, filed Jan. 6, 2011, which claims the benefit of U.S. Provisional Application No. 61/292,668, filed Jan. 6, 2010, which are herein incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: COGO_022_01WO_SeqList_ST25.txt, date recorded: Jan. 6, 2011, file size 40 kilobytes).

FIELD OF THE INVENTION

The present invention relates to pharmaceutical compositions comprising peptide dimers derived from apolipoprotein E (ApoE). The present invention also relates to methods of treating various disease states, such as cancer and neurodegenerative diseases, with the novel compositions.

BACKGROUND OF THE INVENTION

Cancer is a class of diseases in which a group of cells exhibit uncontrolled growth, invasion and destruction of adjacent tissues, and metastasis (spread of aberrant cells spread to other locations in the body), or in which cells fail to undergo programmed cell death (e.g. apoptosis) at the appropriate time. Cancer causes about 13% of all deaths worldwide and according to the American Cancer Society, 7.6 million people died from cancer in the world during 2007. Current treatment for cancer depends upon the specific type of cancer and tissue involved, but includes surgery, chemotherapy, radiation therapy, immunotherapy, and monoclonal antibody therapy among other methods. Although these treatment methods have been successful in some cases, they are hindered by adverse side effects or limited efficacy. For example, the efficacy of eliminating cancerous tissue by surgical removal of tumors is often limited by the tendency of cancers to invade adjacent tissue and metastasize to other sites in the body. Chemotherapy, as well as radiation treatment, is often limited by toxicity or damage to other tissues in the body. Thus, cancer remains a major health concern and there is a need for improved methods of treating cancer.

Inflammation is strongly correlated to cancer initiation, progression and metastasis (Mantovani et al. (2008) Nature, Vol. 454: 436-444). Pro-inflammatory mediators such as prostaglandins, cytokines, reactive oxygen/nitrogen species, and growth factors, activate PI3K/Akt signaling that increases pro-survival, proliferative, and metastatic processes (Dillon et al. (2007) Oncogene, Vol. 26: 1338-1345; Qiao et al. (2008) Cell Cycle, Vol. 7: 2991-2996; Prueitt et al. (2007) International Journal of Cancer, Vol. 120: 796-805; Wang and DuBois (2006) Gut, Vol. 55: 115-122). Mutations in the PI3K/Akt pathway are common in human tumors, which result in unregulated PI3K/Akt signaling (Carnero et al. (2008) Curr Cancer Drug Targets, Vol. 8: 187-98; Dillon et al., 2007; Yuan and Cantley (2008) Oncogene, Vol. 27: 5497-5510). Thus, pharmacological control of the PI3K/Akt signaling axis is an aim for cancer therapeutics.

Akt kinase activity is directly regulated by the tumor suppressor protein phosphatase 2A (PP2A), which functions to dephosphorylate Akt at threonine 308 and serine 473 (Andjelkovic et al. (1996) Proc. Natl. Acad. Sci., Vol. 93: 5699-5704; Resjö et al. (2002) Cellular Signalling, Vol. 14: 231-238). However, PP2A activity is commonly decreased in human cancers (Chen et al. (2004) Cancer Cell, Vol. 5: 127-136). One mechanism by which PP2A activity is suppressed in cancer is by the formation of complexes with endogenous protein inhibitors such as CIP2A and $I_2$PP2A (Junttila et al. (2007) Cell, Vol. 130: 51-62; Li et al. (1996) J. Biol. Chem., Vol. 271: 11059-11062). $I_2$PP2A, which is also known as SET, is a potent inhibitor of PP2A and has been implicated in AML and blast crisis CML (Li et al., 1996; Neviani et al. (2005) Cancer Cell, Vol. 8: 355-368). Despite the endogenous inhibition in many human cancers, PP2A activity can be pharmacologically increased and is a potential molecular target for cancer therapeutics (Guichard et al. (2006) Carcinogenesis, Vol. 27: 1812-1827; Perrotti and Neviani (2008) Cancer and Metastasis Reviews, Vol. 27: 159-168; Switzer et al. (2009) Oncogene, Vol. 28: 3837-3846).

ApoE-derived peptides have shown promising effects in abating injury in inflammation-associated neuropathologies, such as Alzheimer's disease, multiple sclerosis and traumatic brain injury (Hoane et al. (2009) Journal of Neurotrauma, Vol. 26: 121-129; Li et al. (2006) J Pharmacol Exp Ther, Vol. 318: 956-965; Wang et al. (2007) Neuroscience, Vol. 144: 1324-33; WO 2006/029028; WO 2003/026479). Inflammation is a common feature of both neurological diseases and cancer, and PI3K/Akt signaling is also unregulated in neurodegenerative diseases such as Alzheimer's (Griffin et al. (2005) J Neurochem, Vol. 93: 105-17; Pei et al. (2003) Acta Neuropathol, Vol. 105: 381-92). Also, the expression of PP2A subunits is decreased in Alzheimer's patients, which is consistent with increased tau hyperphosphorylation observed in this pathology (Vogelsberg-Ragaglia et al. (2001) Experimental Neurology, Vol. 168: 402-412). ApoE peptides have also been reported to increase PP2A activity by relieving inhibition by SET (see, e.g., WO 2008/080082). Thus, ApoE peptides represent a viable therapeutic approach for treating various conditions, including cancer, inflammatory conditions, and neurodegenerative diseases.

Although several ApoE peptides have proven to be effective in treating specific conditions, there is a need in the art to develop new ApoE-derived peptides with increased potency and greater safety windows. In particular, it is desirable to develop new ApoE-based peptide therapeutics that can effectively treat multiple conditions.

SUMMARY OF THE INVENTION

The present invention is based, in part, on the discovery that dimerization of ApoE peptides increases their biological activity. Thus, the present invention provides novel ApoE peptide therapeutics with increased potency as compared to monomeric ApoE peptides. For instance, in one embodiment, a peptide dimer of the invention comprises a first ApoE peptide and a second ApoE peptide, wherein said first and second ApoE peptides are covalently linked by a linking moiety. In certain embodiments, the first and second ApoE peptides contain a sequence derived from the LDL receptor binding region of the native ApoE holoprotein. The first and second ApoE peptides may be identical or may be different.

In some embodiments, at least one of the ApoE peptides in the dimer is conjugated to a protein transduction domain through, optionally, one or more linking residues. In other embodiments, both the first and second ApoE peptides in the dimer are each conjugated to a protein transduction domain through, optionally, one or more linking residues. The one or more linking residues can include cysteine residues, or modified amino acids, such as azidohomoalanine or propargylglycine. The protein transduction domain can be a peptide derived from antennapedia, TAT, SynB1, SynB3, SynB5, and polyarginine.

The first and second ApoE peptides in the peptide dimers of the invention may be covalently linked by a linking moiety. The linking moiety can include a disulfide bridge, a bismaleimide (e.g., bismaleimido-ethane or bismaleimido-hexane), a 1,4-disubstituted triazole, and N,N-dipropargylamine.

The present invention also includes pharmaceutical compositions of the ApoE peptide dimers of the invention. In one embodiment, the pharmaceutical composition comprises an effective amount of an ApoE peptide dimer as described herein and a pharmaceutically acceptable carrier. In some embodiments, the pharmaceutical compositions may further comprise additional therapeutic compounds depending on the particular condition to be treated.

The present invention also provides methods of treating, preventing, or ameliorating various conditions or diseases, including cancer, neurodegenerative disorders (e.g., ALS, Alzheimer's disease, Parkinson's disease, and Huntington's disease), and inflammatory conditions (e.g., multiple sclerosis, inflammatory bowel disease, Crohn's disease, and rheumatoid arthritis) by administering an effective amount of at least one ApoE peptide dimer as described herein.

The present invention also includes a method for predicting or evaluating the efficacy of a therapeutic intervention for treating cancer in a patient. In one embodiment, the method comprises measuring the expression level of SET protein in a biological sample from a patient, and comparing the measured level to the expression level of SET protein in a control sample, wherein the measured expression level of SET protein is indicative of the therapeutic efficacy of the therapeutic intervention. In certain embodiments, the therapeutic intervention is an ApoE peptide or peptide dimer described herein. The biological sample can be, for example, a tumor biopsy from a solid tumor or mononuclear cells isolated from a blood sample. In one embodiment, the biological sample is CD19+/CD5+ leukemia cells.

The present invention also encompasses a kit for predicting the therapeutic efficacy of ApoE peptides or peptide dimers for treating cancer in a patient. In one embodiment, the kit comprises a reagent for measuring SET protein expression in a biological sample and instructions for measuring SET protein expression for predicting or evaluating the efficacy of an ApoE peptide or peptide dimer for treating cancer in a patient.

BRIEF DESCRIPTION OF THE DRAWINGS

FIG. 2A shows mass spectra of original lot #313 of COG112. FIG. 2B shows mass spectra of COG112 from lot #313 reduced with dithiothreitol. FIG. 2C shows mass spectra of COG112 exposed to oxidizing conditions to form a dimer. Red arrows indicate peaks that are characteristic of a COG112 disulfide bridged dimer.

FIG. 4A: 32D-BCR/Abl chronic myelogenous leukemia cells were treated with COG449 (1 μM), COG445 (1 μM) (disulfide-linked COG112 dimer) or no treatment, and the PP2A activity was measured. FIG. 4B: 32D:BCR/Abl cell cultures were treated with no compound, 1 μM COG449, or 5 μM FTY720 for 30 minutes followed by lysis in an NP40 lysis buffer. PP2A was immunoprecipitated and assayed with the PP2A Immunoprecipitation assay kit (Upstate) according to the manufacturer's directions.

FIGS. 8A-8B. Bismaleimide coupling. FIG. 8A: The chemical transformation involved in the bismaleimide coupling reaction. Cysteine residues incorporated during peptide synthesis are coupled together through a bismaleimide compound such as bismaleimido-ethane (BMOE) or bismaleimido-hexane (BMH). FIG. 8B: Chemical structures of BMOE and BMH.

FIG. 9A: Heterocoupling of a propargylglycine peptide and an azidohomoalanine peptide results in a heterodimeric peptide. FIG. 9B: Homodimeric peptides can be synthesized by coupling two azidohomoalanine-containing monomer peptides with N,N-dipropargylamine.

FIGS. 10A-10B. COG445 inhibits EGF-induced Akt activation in breast cancer and glioblastoma cell lines. FIG. 10A: Western blot analysis of U87 glioblastoma cells exposed to the indicated concentrations of COG445 peptide in the presence of EGF. The blot is probed with antibodies for the activated EGF receptor (P-EGFR), total EGF receptor, activated PDK1 (P-PDK1), and total PDK1. FIG. 10B: Western blot and densitometry analysis of Akt activation induced by EGF in U87 cells in the presence of increasing concentrations of COG445.

FIG. 11A: Western blot analysis of MDA-MB-231 cells treated with the indicated concentrations of COG445 and EGF in the presence or absence of okadaic acid. The blot is probed with an antibody for activated Akt (P-Akt) and total Akt. FIG. 11B: Densitometry analysis of Akt activation induced by EGF in MDA-MB-231 cells in the presence of increasing concentrations of COG445 with and without okadaic acid treatment. The ratio of phosphorylated Akt to total Akt is normalized to that of the EGF alone control. FIG. 11C: Nonlinear regression analysis of the data depicted in FIG. 11B.

FIG. 13A: Western blot and densitometry analysis of phosphorylated m-TOR levels in MDA-MB-231 cells treated with EGF and the indicated concentrations of COG445 in the presence or absence of okadaic acid. FIG. 13B: Western blot analysis of phosphorylated GSK-3β levels in MDA-MB-231 cells treated with EGF and the indicated concentrations of COG445 in the presence or absence of okadaic acid.

FIG. 16A: Scatter plot of the SET/β-Actin ratio measured for 16 CLL patients and 6 normal B-cell samples showing a significant increase in expression of SET in B-CLL cells relative to normal B-cells. Representative Western blots are shown. FIG. 16B: mRNA was isolated from the same patient and volunteer samples and SET mRNA was quantified by qPCR.

FIG. 17A: mRNA was isolated from Raji and Ramos cells and normal B-cells and SET mRNA was quantified by qPCR. FIG. 17B: Western blots showing SET and GAPDH from the same cells in panel A showing a significant increase in expression of SET in B-cell lymphoma lines relative to normal B-cells (N004 and N007).

FIG. 20A: Sequence homology of the c-myc regulatory sites and the Mcl-1 sequence from 159-164 showing conservation of the S/T-X-S-S-S/T-P (SEQ ID NO: 89) motif. FIG. 20B: A schematic representation of the proposed regulatory complex for Mcl-1 (adapted from figure provided by R. Sears).

FIG. 21A shows an immunoblot of SET that co-immunoprecipitated with Mcl-1. FIG. 21B shows an immunoblot of PP2A that co-immunoprecipitated with Mcl-1. FIG. 21C shows an immunoblot of Pin1 that co-immunoprecipitated with Mcl-1. FIG. 21D shows an immunoblot of Axin that co-immunoprecipitated with Mcl-1.

FIG. 25A shows the expression of SET by qRT-PCR in 13 TNBC patient samples relative to normal tissue (N). FIG. 25B shows the expression of CIP2A by qRT-PCR in 13 TNBC patient samples relative to normal tissue (N).

FIG. 30A: $4\times10^6$ MDA-MB-231 cells were injected with Matrigel into the 4th mammary glands of immune compromised mice and treated daily by subcutaneous injection of 10 mg/kg COG449 starting at day 10. FIG. 30B: $4\times10^6$ MDA-MB-231 cells were injected with Matrigel into the 4th mammary glands of immune compromised mice and treated by intravenous tail vein injection 3× week at 1 mg/kg starting at day 27 post injection. Tumor volume was determined by caliper measurement.

DETAILED DESCRIPTION OF THE INVENTION

Figure 1:
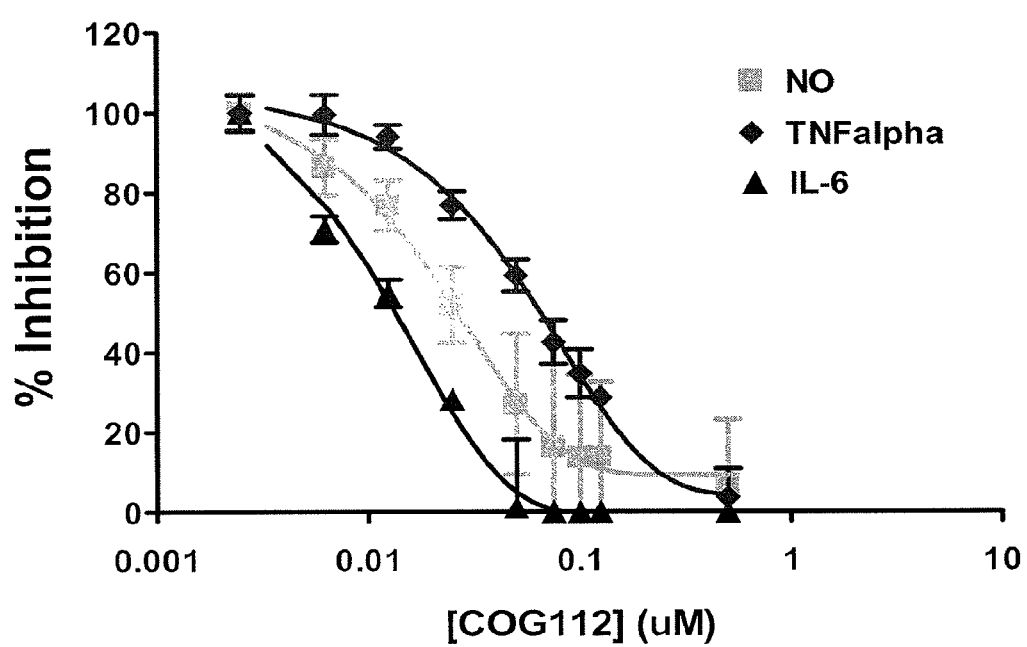
FIG. 1. COG 112 inhibits LPS-induced production of inflammatory cytokines in BV2 microglia cells. Inhibition curves for COG112 in the production of NO (green squares), TNFα (red diamonds), and IL-6 (blue triangles) by BV2 microglia. Compounds were added to the final concentrations indicated on the graph along with 100 ng/mL of LPS. After 24 hours the media was removed and assayed by two-site ELISA (BioSource) and quantitated relative to a standard curve on the same plate.

The inventors previously discovered that ApoE synthetic peptides were useful in treating various types of cancer. See WO 2010/002982, filed Jul. 1, 2009, which is herein incorporated by reference in its entirety. Here, the inventors have expanded upon their earlier work finding surprisingly that dimers of the synthetic ApoE peptides exhibit increased biological activity as compared to their monomeric counterparts. The inventors discovered that one particular lot of ApoE peptide, which was particularly potent in activity assays, had been oxidized to form peptide dimers. Additional experiments demonstrated that ApoE peptide dimers formed through irreversible linkages were even more potent than the reversibly-linked dimers. Accordingly, the present invention provides novel peptide dimers derived from the receptor binding region of ApoE. In one embodiment, the peptide dimer comprises a first ApoE peptide and a second ApoE peptide, wherein said first and second ApoE peptides are covalently linked by a linking moiety.

ApoE peptides, also referred to as COG peptides, are peptides derived from the native ApoE holoprotein. The peptide dimers of the present invention comprise at least two ApoE peptides or ApoE mimetic domains. The ApoE peptides or mimetic domains may be derived from the LDL receptor binding region of the ApoE holoprotein, namely amino acids 130-150 of full-length ApoE protein. In certain embodiments, the ApoE peptides or mimetic domains of the invention may be derived from at least amino acids 133-140 of ApoE. In one embodiment of the invention, the ApoE peptide is derived from amino acids 130-149 of ApoE. In another embodiment, the ApoE peptide is derived from amino acids 133-149 of ApoE. In still another embodiment, the ApoE peptide is derived from amino acids 138-149 of ApoE. As used herein, the phrase "derived from" refers to a peptide that contains at least 80% identity to a particular amino acid sequence from the ApoE protein or a peptide that has at least 5, 6, 7, 8, 9, 10, 11, 12, 13, 14, 15, 16, 17, 18, 19, or 20 contiguous amino acid residues from a receptor binding region of the ApoE protein (e.g. amino acids 130-150). By way of example, a peptide having a sequence corresponding to amino acids 133-149 with one, two, or three point mutations or amino acid modifications would be considered to be derived from amino acids 133-149 of the ApoE protein. ApoE peptides or mimetic domains can be derivatives of a peptide containing five or more, ten or more residues, or 15 or more residues from amino acids 133-149 of native ApoE protein, including derivatives having non-natural amino acid substitutions, such as amino isobutyric acid and acetyl lysine, and other modifications that enhance the alpha-helical content of the peptide.

In one embodiment of the invention, the first and/or second ApoE peptide of the peptide dimer has a sequence of LRVRLASHLRKLRKRLL (SEQ ID NO: 3 (COG133)). The COG133 monomer has previously proven useful in treating or reducing cerebral ischemia or cerebral inflammation. See U.S. Application Publication No. 2003/0077641 A1, filed Sep. 23, 2002, incorporated herein by reference in its entirety. In another embodiment, the first and/or second ApoE peptide is an analog or derivative of COG133. For instance, the first and/or second ApoE peptide has a sequence selected from the group consisting of AS(Aib)LRKL(Aib)KRLL (SEQ ID NO: 5 (COG1410)), LRVRLAS(Aib)LKRLRK(Nitro-Arg)LL (SEQ ID NO: 4 (COG248)), and LRVRLAS(Aib)LRKLR(K-Ac)RLL (SEQ ID NO: 35 (COG345)). Other ApoE analogs or derivatives can be incorporated into the ApoE peptide dimers of the invention. For instance, a large number of analogs of the ApoE 130-150 peptide were previously created and their activity tested in a cell-based assay for suppression of release of inflammatory cytokines and free radicals and in receptor binding assays. Lynch et al. (2003) J. Biol. Chem., Vol. 278(4): 48529-33 and U.S. Application Publication Serial No. 2003/0077641 A1, filed Sep. 23, 2002; U.S. Pat. No. 7,205,280, issued Apr. 17, 2007; and U.S. application Ser. No. 09/260,430, filed Mar. 1, 1999, the contents of each of which are incorporated herein by reference in their entireties. In particular, the improved ApoE analogs described in WO 2006/029028, which is herein incorporated by reference in its entirety, are suitable first and/or second ApoE peptides or mimetic domains of the peptide dimers of the invention. For instance, ApoE peptides or mimetic domains can include, but are not limited to:

```
                                       (SEQ ID NO: 42)
LRVRLASH-(NMe)-LRKLRKRLL-NH2

(SEQ ID NO: 43)
Ac-ASH-Aib-RKLRKRLL-NH2

(SEQ ID NO: 44)
Ac-AS-Aib-LRKLRKRLL-NH2

(SEQ ID NO: 45)
Ac-DS-Aib-LRKLRKRLL-NH2

(SEQ ID NO: 46)
Ac-ASHLRKL-Aib-KRLL-NH2

(SEQ ID NO: 47)
Ac-DR-Aib-ASHLRKLRKR-Aib-L-NH2

(SEQ ID NO: 48)
Ac-DS-Aib-LRKLRKR-Aib-L-NH2

(SEQ ID NO: 49)
Ac-DR-Aib-ASHLRKL-Aib-KRLL-NH2

(SEQ ID NO: 50)
Ac-DS-Aib-LRKL-Aib-KRLL-NH2

(SEQ ID NO: 51)
Ac-DR-Aib-AS-Aib-LRKLRKRLL-NH2

(SEQ ID NO: 52)
Ac-DR-Aib-ASHLRKLRKRLL-NH2
```

-continued

Ac-CAS-Aib-LRKL-Aib-KRLL-NH₂ (SEQ ID NO: 53)

Ac-DS-Aib-LRKL-Aib-KRLL-NH₂ (SEQ ID NO: 54)

Ac-AS-Aib-LRKL-Aib-KRLV-NH₂ (SEQ ID NO: 55)

Ac-AS-Aib-LRKL-Aib-KRLM-NH₂ (SEQ ID NO: 56)

Ac-AS-Aib-LRKL-Aib-KRLI-NH₂ (SEQ ID NO: 57)

Ac-AS-Aib-LRKL-Aib-KRLA-NH₂ (SEQ ID NO: 58)

Ac-AS-Aib-LRKL-Aib-KALL-NH₂ (SEQ ID NO: 59)

Ac-AS-Aib-LRKL-Aib-K(orn)LL-NH₂ (SEQ ID NO: 60)

Ac-AS-Aib-LRKL-Aib-K(narg)LL-NH₂ (SEQ ID NO: 61)

Ac-AS-Aib-LRKL-Aib-K(harg)LL-NH₂ (SEQ ID NO: 62)

Ac-AS-Aib-LRKL-Aib-K(dmarg)LL-NH₂ (SEQ ID NO: 63)

Ac-AS-Aib-LRKL-Aib-ARLL-NH₂ (SEQ ID NO: 64)

Ac-AS-Aib-LRKL-Aib-(aclys)RLL-NH₂ (SEQ ID NO: 65)

Ac-AS-Aib-LRKL-Aib-(azlys)RLL-NH₂ (SEQ ID NO: 66)

Ac-ASH-Aib-RKL-Aib-KRLL-NH₂ (SEQ ID NO: 67)

Ac-AS-Aib-LRKL-Aib-KRL-(NLe)-NH₂ (SEQ ID NO: 68)

Ac-AS-Aib-LRKL-Aib-KR-(NLe)-L-NH₂ (SEQ ID NO: 69)

Ac-AS-Aib-LRKL-Aib-KR-(NLe)-(NLe)-NH₂ (SEQ ID NO: 70)

Ac-AS-Aib-LRKL-Aib-K(orn)L-(NLe)-NH₂ (SEQ ID NO: 71)

Ac-AS-Aib-LRKL-Aib-K(orn)-(NLe)-L-NH₂ (SEQ ID NO: 72)

Ac-AS-Aib-LRKL-Aib-K(orn)-(NLe)-(NLe)-NH₂ (SEQ ID NO: 73)

Ac-AS-Aib-LRKL-Aib-K(harg)L-(NLe)-NH₂ (SEQ ID NO: 74)

Ac-AS-Aib-LRKL-Aib-K(harg)-(NLe)-L-NH₂ (SEQ ID NO: 75)

Ac-AS-Aib-LRKL-Aib-K(harg)-(NLe)-(NLe)-NH₂ (SEQ ID NO: 76)

Ac-AS-Aib-L(orn)KL-Aib-KRLL-NH₂ (SEQ ID NO: 77)

Ac-AS-Aib-L(orn)KL-Aib-K(orn)LL-NH₂ (SEQ ID NO: 78)

Ac-AS-Aib-L(orn)KL-Aib-KRL-(NLe)-NH₂ (SEQ ID NO: 79)

Ac-AS-Aib-L(orn)KL-Aib-KRL-(NLe)-(NLe)-NH₂ (SEQ ID NO: 80)

Ac-AS-Aib-L(orn)KL-Aib-K(orn)L-(NLe)-NH₂ (SEQ ID NO: 81)

Ac-AS-Aib-L(orn)KL-Aib-K(orn)-(NLe)-(NLe)-NH₂ (SEQ ID NO: 82)

Ac-ASHLRKLRKRLL-NH₂ (apoE138-149) (SEQ ID NO: 83)

Ac-ASHCRKLCKRLL-NH₂ (SEQ ID NO: 84)

Ac-ASCLRKLCKRLL-NH₂ (SEQ ID NO: 85)

Ac-CSHLRKLCKRLL-NH₂ (SEQ ID NO: 86)

Ac-ASHLRKCRKRCL-NH₂ (SEQ ID NO: 87)

Ac-ASHCRKLRKRCL-NH₂ (SEQ ID NO: 88)

wherein (NMe)-L is an N-methylated Leucine, Aib is amino iso-butyric acid, (orn) is ornithine, (narg) is nitroarginine, (NLe) is norleucine, (harg) is homoarginine, (dmarg) is dimethyl arginine, (aclys) is acetyl lysine, (azlys) is azalysine and Ac is an acetylated amino terminus. Other ApoE peptides or mimetic domains derived from the receptor binding region of ApoE protein are also contemplated. For instance, ApoE peptides or mimetic domains that comprise a sequence corresponding to amino acids 133-149 of ApoE protein and retain (i.e. not substituted) one or more key residues selected from the group consisting of S139, R142, K143, L144, K146, R147 and L149, but have one or more amino acid substitutions at other positions are suitable first and/or second ApoE peptides or mimetic domains of the peptide dimers of the invention.

In certain embodiments of the invention, the first and second ApoE peptides of the peptide dimer are the same. For example, in one embodiment, the peptide dimer comprises a first ApoE peptide and a second ApoE peptide, wherein the first and second peptide have a sequence of SEQ ID NO: 3 (COG133). In other embodiments, the first and second ApoE peptides of the peptide dimer are different. By way of example, the peptide dimer can comprise a first ApoE peptide and a second ApoE peptide, wherein the first ApoE peptide has a sequence of SEQ ID NO: 3 (COG133) and the second ApoE peptide has a sequence of SEQ ID NO: 5 (COG1410). Peptide dimers including all possible permutations of the different ApoE peptides described herein are encompassed by the present invention.

In another embodiment of the invention, the first and/or second ApoE peptide of the peptide dimer is conjugated to a protein transduction domain (PTD). PTDs are short basic peptides that enhance the intracellular delivery of cargo. Some non-limiting examples of PTDs that may be conjugated to the ApoE peptides include peptides derived from antennapedia, SynB1, SynB3, SynB5, TAT, and polyarginine. For instance, exemplary PTD sequences that can be conjugated to the first and/or second ApoE peptides include:

RQIKIWFQNRRMKWKK (SEQ ID NO: 8)

YGRKKRRQRRR (SEQ ID NO: 9)

```
GRKKRRQRRRPPQ         (SEQ ID NO: 36)

RRMKWKK               (SEQ ID NO: 37)

RGGRLSYSRRRFSTSTGR    (SEQ ID NO: 38)

RRLSYSRRRF            (SEQ ID NO: 39)

RGGRLAYLRRRWAVLGR     (SEQ ID NO: 40)

RRRRRRRR              (SEQ ID NO: 41)

WKK
```

In certain embodiments, the first and/or second ApoE peptide is conjugated to a PTD having a sequence of RQIKIWFQNRRMKWKK (SEQ ID NO: 8); YGRKKRRQRRR (SEQ ID NO: 9), or WKK. In one embodiment, the first ApoE peptide is conjugated to a first PTD through one or more first linking residues. Thus, the peptide dimers of the invention can comprise a first ApoE peptide conjugated to a first PTD and a second ApoE peptide that is not conjugated to a PTD. In such embodiments, the peptide dimers comprise two ApoE peptides or mimetic domains and a single PTD. In another embodiment, the first ApoE peptide is conjugated to a first PTD through one or more first linking residues and the second ApoE peptide is conjugated to a second PTD through one or more second linking residues. In such embodiments, the peptide dimers comprise two ApoE peptides or mimetic domains and two PTDs. Thus, the peptide dimers of the invention can comprise two ApoE peptide domains with zero, one, or two PTDs. See Example 3 and FIG. 7.

The ApoE peptides and PTDs of the dimers can be any combination of the ApoE peptides and PTDs described herein. In particular embodiments, the PTDs are selected from peptides derived from antennapedia or TAT (e.g., SEQ ID NO: 8, SEQ ID NO: 9, or the WKK sequence) and the ApoE peptides are selected from COG133 (SEQ ID NO: 3), COG248 (SEQ ID NO: 4), COG1410 (SEQ ID NO: 5), or COG345 (SEQ ID NO: 35) as described in Tables II and IV of Example 3. In a certain embodiment, the ApoE peptide is COG133 (SEQ ID NO: 3) and the PTD has a sequence of SEQ ID NO: 8. In another embodiment, the ApoE peptide is COG133 (SEQ ID NO: 3) and the PTD has a sequence of WKK. In another embodiment, the peptide dimer comprises a first peptide and a second peptide, wherein said first peptide and said second peptide are covalently linked by a bismaleimido-ethane, and wherein the first and second peptide have a sequence of SEQ ID NO: 1, SEQ ID NO: 15, or SEQ ID NO: 90. For example, in one particular embodiment, the peptide dimer comprises a first peptide and a second peptide, wherein the first and second peptide have a sequence of SEQ ID NO: 1, and wherein said first peptide and said second peptide are covalently linked by a bismaleimido-ethane linker between the cysteine residues at position 17 in SEQ ID NO: 1 (e.g., the peptide dimer is COG449; see Table I). In another particular embodiment, the peptide dimer comprises a first peptide and a second peptide, wherein the first and second peptide have a sequence of SEQ ID NO: 15, and wherein said first peptide and said second peptide are covalently linked by a bismaleimido-ethane linker between the cysteine residues at the amino terminus of each peptide (i.e. at position 1 in SEQ ID NO: 15) (e.g., the peptide dimer is COG492; see Table I). In still another particular embodiment, the peptide dimer comprises a first peptide and a second peptide, wherein the first and second peptide have a sequence of SEQ ID NO: 90, and wherein said first peptide and said second peptide are covalently linked by a bismaleimido-ethane linker between the cysteine residues at position 4 in SEQ ID NO: 90 (e.g., the peptide dimer is COG493; see Table I).

The first and/or second ApoE peptide may optionally be conjugated to the PTD through one or more linking residues. As used herein, a "linking residue" refers to at least one amino acid or modified amino acid that is capable of undergoing a reaction to cross-link ApoE peptide monomers to form stable dimers. In some embodiments, the linking residues are amenable to cross-linking using maleimide groups, such as those described in FIG. 8, or cross-linking through the formation of stable 1,4-disubstituted triazoles as described in FIG. 9. Exemplary linking residues include cysteine, azidohomoalanine, and propargylglycine. Other suitable linking residues can be ascertained by those of skill in the art.

The peptide dimers of the invention comprise a first ApoE peptide and a second ApoE peptide, wherein said first and second ApoE peptides are covalently linked by a linking moiety. As used herein, a "linking moiety" may be a compound or molecule that cross-links peptide monomers such that the peptide chains are separated by at least four atoms. The linking moiety can be selected to create various lengths of the linker between the peptide monomers. For instance, the linking moiety may be selected such that the peptide chains are separated by at least 6 atoms, at least 8 atoms, at least 10 atoms, or at least 12 atoms. Linking moieties can be heterologous amino acids not found in the native ApoE sequence, such as additional cysteine residues or modified amino acids, such as azidohomoalanine or propargylglycine. In some embodiments, linking moieties can include molecules or compounds that are produced from a cross-linking reaction with amino acids in the peptide chains. For instance, in certain embodiments, the linking moiety is selected from the group consisting of a disulfide bridge, a bismaleimide, a 1,4-disubstituted triazole, and N,N-dipropargylamine. The bismaleimide can include, but is not limited to, bismaleimido-ethane or bismaleimido-hexane. In some embodiments, the linking moiety is not a peptide bond.

In embodiments in which the peptide dimer comprises ApoE peptides that are not conjugated to PTDs, the two ApoE peptides can be linked such that the carboxy terminus of the first ApoE peptide is linked to the amino terminus of the second ApoE peptide (e.g., direct linkage). Alternatively, the two ApoE peptides can be linked such that the two ApoE peptides are in reverse orientation relative to each other. For example, the carboxy terminus of the first ApoE peptide can be linked to the carboxy terminus of the second ApoE peptide or the amino terminus of the first ApoE peptide can be linked to the amino terminus of the second ApoE peptide. Such linkages may be accomplished by adding one or more amino acid residues capable of undergoing cross-linking reactions (e.g. cysteine, azidohomoalanine, or propargylglycine residues) to the appropriate terminus of the first and second ApoE peptides. By way of example, cysteine residues added to the amino terminus of both the first and second ApoE peptides will generate a dimer in which the first and second ApoE peptides are linked at their amino termini (see, e.g., COG492 in Example 2).

In embodiments, in which the peptide dimer comprises at least one ApoE peptide conjugated to a PTD, the dimer can be formed by cross-linking at least one of the linking residues in the ApoE-PTD conjugate and an amino acid at either the carboxy or amino terminus of the second, unconjugated ApoE peptide. If both ApoE peptides are conjugated to PTDs, the dimer is preferably formed by cross-linking at least one of the linking residues in each ApoE-PTD conjugate such that the two peptide chains are linked through internal amino acid residues.

ApoE peptides or mimetic domains may be incorporated into multimers such that an ApoE multimer contains three or more ApoE peptides or mimetic domains. One or more of the ApoE peptides in the multimer can be conjugated to a PTD as described herein. In one embodiment, the present invention provides an ApoE trimer comprising a first ApoE peptide, a second ApoE peptide, and a third ApoE peptide, wherein the first, second, and third ApoE peptides are covalently linked by a linking moiety. Other ApoE multimers are contemplated within the scope of the invention.

Peptides of the present invention can be produced by standard techniques as are known in the art. The peptides of the invention may have attached various label moieties such as radioactive labels, heavy atom labels and fluorescent labels for detection and tracing. Fluorescent labels include, but are not limited to, luciferin, fluorescein, eosin, Alexa Fluor, Oregon Green, rhodamine Green, tetramethylrhodamine, rhodamine Red, Texas Red, coumarin and NBD fluorophores, the QSY 7, dabcyl and dabsyl chromophores, BODIPY, Cy5, etc.

Modification of the peptides disclosed herein to enhance the functional activities associated with these peptides could be readily accomplished by those of skill in the art. For instance, the peptide dimers of the present invention can be chemically modified or conjugated to other molecules in order to enhance parameters such as solubility, serum stability, etc., while retaining functional activity. In particular, the first and/or second ApoE peptide of the dimer may be acetylated at its N-terminus and/or amidated at its C-terminus, or the dimers can be further conjugated, complexed or fused to molecules that enhance serum stability, including but not limited to albumin, immunoglobulins and fragments thereof, transferrin, lipoproteins, liposomes, $\alpha$-2-macroglobulin and $\alpha$-1-glycoprotein, PEG and dextran. Such molecules are described in detail in U.S. Pat. No. 6,762,169, which is herein incorporated by reference in its entirety.

The ApoE peptides of the inventive peptide dimers can further include conservative variants of the peptides described herein. As used herein, a conservative variant refers to alterations in the amino acid sequence that do not adversely affect the biological functions of the peptide. A substitution, insertion or deletion is said to adversely affect the peptide when the altered sequence prevents or disrupts a biological function associated with the peptide. For example, the overall charge, structure or hydrophobic/hydrophilic properties of the peptide may be altered without adversely affecting a biological activity. Accordingly, the amino acid sequence can be altered, for example to render the peptide more hydrophobic or hydrophilic, without adversely affecting the biological activities of the peptide. Ordinarily, the conservative substitution variants, analogs, and derivatives of the peptides, will have an amino acid sequence identity to the disclosed sequences, SEQ ID NOs: 3, 4, 5, and 35, of at least about 55%, at least about 65%, at least about 75%, at least about 80%, at least about 85%, at least about 90%, at least about 95%, or at least about 96% to 99%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the first and/or second ApoE peptides of the peptide dimers of the present invention include molecules having the amino acid sequence disclosed in SEQ ID NOs: 3, 4, 5, and 35; fragments thereof having a consecutive sequence of at least about 3, 4, 5, 6, 10, 15, or more amino acid residues of the therapeutic peptide; amino acid sequence variants of such peptides wherein an amino acid residue has been inserted N- or C-terminal to, or within, the disclosed sequence; and amino acid sequence variants of the disclosed sequence, or their fragments as defined above, that have been substituted by another residue. Contemplated variants further include those containing predetermined mutations by, e.g., homologous recombination, site-directed or PCR mutagenesis, and the corresponding peptides of other animal species, including but not limited to rabbit, rat, porcine, bovine, ovine, equine and non-human primate species, and derivatives wherein the peptide has been covalently modified by substitution, chemical, enzymatic, or other appropriate means with a moiety other than a naturally occurring amino acid (for example, a detectable moiety such as an enzyme or radioisotope).

Methods of cross-linking peptides to form peptide dimers are known to those in the art and can include, but are not limited to, coupling via maleimide groups and coupling using "click chemistry" (see Example 3 and FIGS. 8-9). The skilled artisan can ascertain other suitable methods for covalently linking the ApoE peptides described herein to form peptide dimers without undue experimentation.

The ApoE peptide dimers of the invention can be in free form or the form of a salt, where the salt is pharmaceutically acceptable. These include inorganic salts of sodium, potassium, lithium, ammonium, calcium, magnesium, iron, zinc, copper, manganese, and the like. Various organic salts of the peptide may also be made with, including, but not limited to, acetic acid, propionic acid, pyruvic acid, maleic acid, succinic acid, tartaric acid, citric acid, benozic acid, cinnamic acid, salicylic acid, etc.

In one embodiment, the peptide dimers of the present invention are used in combination with a pharmaceutically acceptable carrier. Thus, the present invention also provides pharmaceutical compositions suitable for administration to a subject. Such compositions comprise an effective amount of an ApoE peptide dimer of the present invention in combination with a pharmaceutically acceptable carrier. The carrier can be a liquid, so that the composition is adapted for parenteral administration, or can be solid, i.e., a tablet or pill formulated for oral administration. Further, the carrier can be in the form of a nebulizable liquid or solid so that the composition is adapted for inhalation. When administered parenterally, the composition should be pyrogen free and in an acceptable parenteral carrier. Active agents can alternatively be formulated encapsulated in liposomes, using known methods. Preparation of a peptide dimer of the present invention for intranasal administration can be carried out using techniques as are known in the art. The inventive peptide dimers may also be formulated for topical administration, for example in the form of creams or gels. Topical formulations are particularly useful for treating skin cancers or inflammatory skin conditions. In other embodiments, the ApoE peptide dimers may be formulated for rectal administration, such as in the form of suppositories. In some embodiments, rectal administration of the ApoE peptide dimers may be preferred for treatment of colorectal cancer, inflammatory bowel disease, or Crohn's disease.

Pharmaceutical preparations of the peptide dimers of the present invention can optionally include a pharmaceutically acceptable diluent or excipient.

The ApoE peptide dimers of the invention may contain further modifications or be formulated to specifically target specific tissues, such as inflamed tissues or cancerous tumors. For instance, the ApoE peptide dimers may be conjugated to other peptides that localize to tumor cells, such as those described in U.S. Pat. No. 6,380,161, U.S. Publication No. 2003/0232013, WO 2009/155556, and WO 2009/143023. Additionally or alternatively, the ApoE peptide dimers may be encapsulated into liposomes. The liposomes may contain a targeting ligand to localize the liposomes to particular tissues or tumor sites.

An effective amount of an ApoE peptide dimer of the present invention is an amount that decreases at least one symptom or pathology associated with cancer, such as tumor size, tumor growth, spread of cancer cells, number of cancer cells, and survival, compared to that which would occur in the absence of the peptide. An effective amount of an ApoE peptide dimer can also be an amount that decreases microglial activation (i.e., an amount that decreases the production of neurotoxic and neuromodulatory compounds by microglia) as compared to that which would occur in the absence of the compound. The effective amount (and the manner of administration) will be determined on an individual basis and will be based on the specific composition of the peptide dimer being used and a consideration of the subject (size, age, general health), the specific condition being treated (e.g. cancer, neurodegenerative disorder, inflammatory condition), the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the peptide dimers described herein can be determined using in vitro tests, animal models or other dose-response studies, as are known in the art.

The peptide dimers of the present invention can be administered acutely (i.e., during the onset or shortly after events leading to a diagnosis of a particular condition), or can be administered prophylactically (e.g., before scheduled surgery, or before the appearance of signs or symptoms of a particular condition), or administered during the course of a particular disease or condition to reduce or ameliorate the progression of symptoms that would otherwise occur. The timing and interval of administration is varied according to the subject's symptoms, and can be administered at an interval of several hours to several days, over a time course of hours, days, weeks or longer, as would be determined by one skilled in the art.

The typical daily regime can be from about 0.01 µg/kg body weight per day, from about 1 mg/kg body weight per day, from about 10 mg/kg body weight per day, from about 100 mg/kg body weight per day, from about 1,000 mg/kg body weight per day. Depending on the particular ApoE peptide dimer to be administered, dosages can be between about 1 mg/kg and about 500 mg/kg body weight per day, preferably between about 25 mg/kg and about 400 mg/kg body weight per day, or more preferably between about 50 mg/kg and about 250 mg/kg body weight per day.

The present invention provides methods of treating cancer in a subject in need thereof by administering an effective amount at least one ApoE peptide dimer as described herein. In certain embodiments, said at least one ApoE peptide dimer comprises a sequence selected from the group consisting of SEQ ID NOs: 1, 3, 4, 5, 6, 7, 10, 11, 12, 13, 14, 15, 35, 90, and effective fragments and variants thereof. ApoE peptide dimers can reduce one or more symptoms associated with cancer, including but not limited to tumor formation, tumor growth, number of cancerous cells, spread of cancerous cells to healthy tissue, and decreased survival. Cancers that may be treated with the peptide dimers and methods of the invention include, but are not limited to, various forms of leukemia (CLL, CML, ALL, AML), breast cancer, ovarian cancer, cervical cancer, prostate cancer, colorectal cancer, lung cancer, pancreatic cancer, brain cancer (e.g., gliomas), skin cancer (melanoma and nonmelanoma), head and neck cancers, bladder cancer, endometrial cancer, renal cell cancer, thyroid cancer, stomach cancer, esophageal cancer, gall bladder cancer, liver cancer, lymphoma (e.g. non-Hodgkin's lymphoma), and sarcoma. In one embodiment, the ApoE peptide dimers can reduce activation of signaling pathways, such as the Akt pathway, that are aberrantly activated in various forms of cancer (see Example 5). ApoE peptides can also activate PP2A (Examples 2, 5, and 10). PP2A has been reported to negatively regulate endothelial cell motility, which is required for angiogenesis and tumor metastasis in cancers (Gabel et al., 1999, Otolaryngol Head Neck Surg. 121: 463-468; Young, M R., 1997, Adv Exp Med Biol. 407: 311-318). Inhibition of PP2A by okadaic acid increased cell motility by disrupting the cytoskeletal network thereby enhancing the invasive properties of the tumor cells. Thus, peptide dimers of the present invention would reduce tumor cell metastasis and cancer-associated angiogenesis by activating PP2A. In one embodiment of the invention, administration of the ApoE peptide dimer increases PP2A activity in a cancer cell of the subject. In another embodiment, administration of the ApoE peptide dimer decreases Akt kinase activity in a cancer cell of the subject. In yet another embodiment, administration of the ApoE peptide dimer induces cytotoxicity in cancer cells in the subject.

The present invention also provides a method for the treatment of leukemia comprising administering at least one ApoE peptide dimer in an amount that would reduce symptoms of the disease as compared to that which would occur in the absence of the peptide dimer. In one embodiment, the leukemia is chronic myelogenous leukemia (CML). SET (i.e., $I_2PP2A$), an endogenous negative regulator of PP2A, is overexpressed in CML and inhibits PP2A, thus maintaining activation of the oncogenic BCR/ABL kinase pathway (Neviani et al. (2005) Cancer Cell. 8: 355-368). Therefore, administration of an ApoE peptide dimer of the invention would activate PP2A, which would then be free to dephosphorylate regulators of cell proliferation and survival as well as suppress the oncogenic activity of the BCR/ABL kinase thus reducing leukemogenesis. In another embodiment, the leukemia is chronic lymphocytic leukemia (CLL). In preferred embodiments, administration of the ApoE peptide dimer decreases the number of CD5+ B cells in the subject. In another embodiment, the leukemia is acute lymphocytic leukemia (ALL).

The present invention also encompasses methods of treating breast cancer in a subject by administering an effective amount of at least one ApoE peptide dimer to the subject. In one embodiment, the breast cancer is characterized by Her2 expression. In another embodiment, the breast cancer is characterized by estrogen receptor expression. In another embodiment, the breast cancer is characterized by progesterone receptor expression. The ApoE peptide dimers of the invention can be used to treat any of the three main subtypes of breast cancer: luminal tumors (ER+/HER2−), HER2 amplified tumors (HER2+), and triple negative breast cancer (TNBC, ER−/PR−/HER2−). In certain embodiments, the breast cancer to be treated with an ApoE peptide dimer of the invention is triple negative breast cancer characterized by lack of expression of the estrogen receptor, progesterone receptor, and HER2 receptor. Administration of ApoE peptide dimers preferably reduce tumor growth following their administration.

The ApoE peptide dimers of the present invention may be used alone to treat cancer or in combination with other therapeutic agents commonly used to treat cancer, such as, e.g. chemotherapy agents (chlorambucil, cyclophosphamide), corticosteroids (prednisone, prednisolone), fludarabine, pentostatin, cladribine, imatinib (Gleevec), dasatinib (Sprycel), hormonal therapy (tamoxifen, aromatase inhibitors), sorafenib, gefitinib, and radiation. In some embodiments, the ApoE peptide dimers are administered in combination with sorafenib or gefitinib to treat cancer. As used herein, "in combination" means that the ApoE peptide dimer and other therapeutic agents are administered such that their effects overlap in time. Thus, the ApoE peptide dimer can be administered simultaneously with the other therapeutic agent or before or after the other therapeutic agent.

The present invention provides a method for predicting or evaluating the efficacy of a therapeutic intervention for treating cancer in a patient. In one embodiment, the method comprises measuring the expression level of SET protein in a biological sample from a patient, and comparing the measured level to the expression level of SET protein in a control sample, wherein the measured expression level of SET protein is indicative of the therapeutic efficacy of the therapeutic intervention. In certain embodiments, the therapeutic intervention is an ApoE peptide or peptide dimer of the invention. The present inventors have discovered that ApoE mimetic peptides and peptide dimers bind to SET (i.e., $I_2PP2A$) and relieve its inhibition of endogenous PP2A, thereby increasing PP2A activity in the cell. Without being bound by any particular theory, it is believed that this increase in PP2A activity induced by ApoE peptides or peptide dimers triggers apoptosis leading to cytotoxicity of cancer cells. Therefore, cancer cells that overexpress SET protein are particularly susceptible to ApoE peptide-induced cytotoxicity. Accordingly, the present invention includes a method for predicting therapeutic efficacy of an ApoE peptide or peptide dimer for treating cancer in a patient by measuring the expression level of SET protein in a biological sample from the patient and comparing the measured level to the expression level of SET protein in a control sample, wherein the measured expression level of SET protein is predictive of the therapeutic efficacy of the ApoE peptide or peptide dimer.

In one embodiment, a measured SET expression level of at least 2-fold relative to the control sample is predictive of therapeutic efficacy of an ApoE peptide or peptide dimer for treating cancer in the patient. In some embodiments, a measured SET expression level of at least 4-fold, at least 5-fold, at least 8-fold, at least 10-fold, at least 12-fold, at least 15-fold, or at least 20-fold relative to the control sample is predictive of therapeutic efficacy of an ApoE peptide or peptide dimer for treating cancer in the patient. In one embodiment, the method is predictive of therapeutic efficacy of an ApoE peptide or peptide dimer for treating breast cancer in the patient. In another embodiment, the method is predictive of therapeutic efficacy of an ApoE peptide or peptide dimer for treating triple negative breast cancer (estrogen receptor negative, progesterone receptor negative, and HER2 receptor negative) in the patient. In another embodiment, the method is predictive of therapeutic efficacy of an ApoE peptide or peptide dimer for treating B-cell lymphoma (e.g. non-Hodgkin's lymphoma) in the patient. In still another embodiment, the method is predictive of therapeutic efficacy of an ApoE peptide or peptide dimer for treating leukemia (e.g. CML or CLL) in the patient.

SET expression can be measured by assessing the level of SET protein or SET transcript. SET expression can be measured by methods known in the art including, but not limited to, Northern Blot, PCR, RT-PCR, Western Blot, immunoassay (e.g. ELISA or multiplexed assays), 2D gel electrophoresis, and hybridization. In one embodiment, SET protein expression is measured.

In certain embodiments, the method for predicting the efficacy of ApoE peptide therapy for treating cancer in a patient further comprises administering at least one ApoE peptide or peptide dimer to the patient following assessment of SET expression in the patient's biological sample. Any ApoE peptide or dimer thereof described herein is suitable for use in the method. For instance, in some embodiments, an ApoE peptide or dimer thereof having a sequence selected from the group consisting of SEQ ID NOs: 1, 3, 4, 5, 6, 7, 10, 11, 12, 13, 14, 15, 35, 90 and effective fragments and variants thereof is administered to the patient. In another embodiment, the method further comprises adjusting the particular type of ApoE peptide or peptide dimer or dosage of the ApoE peptide or peptide dimer based on the expression level of the SET protein in the patient's biological sample. SET expression levels can be measured multiple times over a particular period of time or treatment period in a patient.

The biological sample can be any tissue sample that contains cancerous cells. For instance, the biological sample can include, but is not limited to, a biopsy from a solid tumor (e.g. breast cancer, lymphoma, sarcoma, etc.) or peripheral blood mononuclear cells (PBMCs) isolated from blood. In one embodiment, the biological sample is CD19+/CD5+ leukemia cells. The control sample can be any tissue sample that contains normal or non-cancerous cells such as PBMCs isolated from a normal, age-matched patient or non-cancerous tissue (e.g. breast, lymph, skin, etc.) isolated from the patient to be treated or from a normal, age-matched control patient.

The present invention also encompasses a kit for predicting or evaluating the efficacy of an ApoE peptide or peptide dimer for treating cancer in a patient. In one embodiment, the kit comprises a reagent for measuring SET protein expression in a biological sample and instructions for measuring SET protein expression for predicting or evaluating the efficacy of an ApoE peptide or peptide dimer for treating cancer in a patient. In some embodiments, the reagent for measuring SET expression can include SET-specific antibodies, ELISA reagents, and primers and probes for amplifying and detecting SET mRNA. In other embodiments, the kit may further comprise one or more normalization controls. For example, the normalization control may be an exogenously added RNA or protein that is not naturally present in the sample or it may be a protein or RNA known to be expressed constitutively in a particular biological sample or cell, such as beta-actin. In such embodiments, the kit may further provide reagents (antibodies, primers, probes, etc.) for detecting and quantitating the normalization control. In some embodiments, the kit can further comprise a set of reference values to which the measured SET expression levels can be compared.

The present invention provides a method of reducing glial activation or microglial activation in a subject in need thereof by administering to the subject at least one of the ApoE peptide dimers of the invention. In one embodiment, the microglial activation is associated with central nervous system (CNS) inflammation, traumatic brain injury, cerebral ischemia or cerebral edema. Thus, the present methods and compositions are useful in preventing, suppressing or reducing the activation of glia in the CNS that occurs as a part of acute or chronic CNS disease. The effect of the present methods and peptide dimers can be assessed at the cellular or tissue level (e.g., histologically or morphometrically), or by assessing a subject's neurological status. The suppression or reduction of glial activation can be assessed by various methods as would be apparent to those in the art; one such method is to measure the production or presence of compounds that are known to be produced by activated glia, and compare such measurements to levels of the same compounds in control situations. Alternatively, the effects of the present methods and peptide dimers in suppressing, reducing or preventing microglial activation can be assessed by comparing the signs and/or symptoms of CNS disease in treated and control subjects, where such signs and/or symptoms are associated with or secondary to activation of microglia.

The present methods and peptide dimers are useful in preventing, treating, or ameliorating neurological signs and symptoms associated with acute CNS injury. As used herein, acute CNS injury includes but is not limited to stroke (caused by thrombosis, embolism or vasoconstriction), closed head injury, global cerebral ischemia (e.g., ischemia due to systemic hypotension of any cause, including cardiac infarction, cardiac arrhythmia, hemorrhagic shock, and post coronary artery bypass graft brain injury), focal ischemia and intracranial hemorrhage. Ischemic damage to the central nervous system can result from either global or focal ischemic conditions. Global ischemia occurs where blood flow to the entire brain ceases for a period of time, such as during cardiac arrest. Focal ischemia occurs when a portion of the brain is deprived of normal blood flow, such as during thromboembolytic occlusion of a cerebral vessel, traumatic head injury, edema and brain tumors. Much of the CNS damage due to cerebral ischemia occurs during the hours or even days following the ischemic condition, and is secondary to the release of cytotoxic products by damaged tissue.

The present methods and peptide dimers are also useful in preventing, treating, or ameliorating the neurological signs and symptoms associated with inflammatory conditions affecting the nervous system including the CNS, including but not limited to multiple sclerosis, vasculitis, acute disseminated encephalomyelitis and Guillain-Barre syndrome. In this regard, the ApoE peptide dimers of the invention can be used alone or in combination with other known anti-inflammatory drugs or cytokines to formulate pharmaceutical compositions for the treatment of CNS inflammatory conditions.

In another embodiment, the present invention provides a method of reducing neuronal cell death in a subject in need thereof comprising administering to the subject an effective amount of at least one ApoE peptide dimer described herein. In some embodiments, the neuronal cell death is associated with glutamate excitotoxicity. It was previously found that the COG 133 monomer peptide significantly suppressed neuronal cell death and calcium influx associated with N-methyl-D-aspartate exposure (see, e.g., U.S. Application Publication No. 2003/0077641 A1, herein incorporated by reference in its entirety). Thus, the peptide dimers of the present invention provide the basis for improved therapeutic compositions for treating diseases associated with glutamate excitotoxicity mediated by overstimulation of the NMDA receptor. For instance, glutamate excitotoxicity has been associated with neurolathyrism, amyotrophic lateral sclerosis (ALS) (Doble (1999) Pharmacol. Ther., Vol. 81:163-221), schizophrenia (Nguimfack (2002) Encephale, Vol. 28: 147-153), Huntington's chorea, Parkinson's (Nguimfack, 2002; Mytilineou et al. (1997) J. Neurochem., Vol. 68: 33-39; Klopman and Sedykh (2002) BMC Pharmacol., Vol. 2: 8; Le and Lipton (2001) Drugs Aging, Vol. 18: 717-724), bipolar disorder (Farber et al. (2002) Mol. Psychiatry, Vol. 7: 726-733), multiple sclerosis in humans and experimental autoimmune encephalitis (EAE) in animals (Paul and Bolton (2002) J. Pharmacol. Exp. Ther., Vol. 302: 50-57), depression, stroke (Le and Lipton, 2001), epilepsy and the inherited neurometabolic disease d-2-hydroxyglutaric aciduria (Kolker et al. (2002) Eur. J. Neurosci., Vol. 16: 21-28), in addition to Alzheimer's Disease (Bi et al. (2002) Neuroscience, Vol. 112: 827-840; Bi et al. (2002) J. Neurol. Sci., Vol. 200: 11-18) and traumatic brain injury (Rao et al. (2001) Brain Res., Vol. 911: 96-100; Regner et al. (2001) J. Neurotrauma, Vol. 18: 783-792; Xu and Luo (2001) Chin. J. Traumatol., Vol. 4: 135-138).

Thus, the present invention includes the use of the disclosed peptide dimers in methods and pharmaceutical formulations for the treatment of any of the above diseases or disorders, and in combined therapeutic compositions containing other known compounds useful for treating the various disorders. For instance, in some embodiments, the peptide dimers of the invention can be used to treat neurolathyrism, amyotrophic lateral sclerosis (ALS), Huntington's disease, Parkinson's disease, or schizophrenia in a subject in need thereof.

Riluzole (RILUTEK®, Rhone-Poulenc) is a substance with glutamate antagonistic properties that is used for neuroprotective treatment in amyotrophic lateral sclerosis and which has been tested in clinical trials for treatment of Huntington's disease and Parkinson's disease (Schiefer et al. (2002) Mov. Disord., Vol. 17: 748-757; Doble, 1999). Schiefer and colleagues recently demonstrated that riluzole prolongs survival time and alters nuclear inclusion formation in a transgenic mouse model of Huntington's disease. Thus, given the probable NMDA antagonistic role of the peptide dimers of the invention, these peptide dimers could be used in pharmaceutical formulations for the treatment of ALS, Huntington's and Parkinson's, alone or in combination with other glutamate antagonists, such as riluzole.

L-deprenyl is an inhibitor of monoamine oxidase (MAO)-B that delays the emergence of disability and the progression of signs and symptoms of Parkinson's disease, and is predicted to exert a protective effect from events occurring downstream from activation of glutamate receptors (Mytilineou et al., 1997). MAO-B inhibitors, dopamine receptor antagonists, such as levodopa, and NMDA receptor antagonists have all been shown to have an antiparkinson effect, and multidrug combinations have been shown to synergistically enhance the antiparkinson effects of the drugs (Klopman and Sedykh, 2002). Thus, given the probable NMDA antagonistic role of the peptide dimers of the invention, these peptide dimers could be used in pharmaceutical formulations for the treatment of Parkinson's, alone or in combination with other NMDA receptor antagonists, MAO-B inhibitors, such as L-deprenyl, and dopamine receptor agonists, such as levodopa.

The production of free radicals as a result of glutamate excitotoxicity has been implicated in the pathogenesis of schizophrenia (Nguimfack, 2002). Thus, researchers have begun to examine treatment of schizophrenia with antioxidizing substances used in other neurological diseases such as ALS, Parkinson's and Huntington's disease. Given that the peptide dimers of the invention likely have NMDA receptor antagonistic properties and can be used to inhibit the production of free radicals as a result of glutamate excitotoxicity, these peptide dimers can be used in pharmaceutical formulations for the treatment of schizophrenia, alone or in combination with other antioxidizing substances.

The present invention also includes a method of treating, preventing or ameliorating the symptoms of multiple sclerosis in a subject in need thereof by administering to the subject an effective amount of at least one ApoE peptide dimer of the invention. Multiple sclerosis (MS) is an immunologically mediated disease, as determined by observation of the response to immunotherapy and the existence of an animal model, experimental autoimmune encephalitis (EAE). See, for example, Mix et al. (2004) J. Neuroimmunol., Vol. 151(1-2): 158-70, Anderson, et al. (2004), Ann. Neurol., Vol. 55(5):654-9, and Ni et al. (2004) Mult. Scler., Vol. 10(2): 158-64. Interferon (IFN) beta-1b, IFN beta-1a, and glatiramer acetate (COPAXONE®, Teva), current therapies used for relapsing or remitting MS, have mechanisms of action that address the immunologic pathophysiology of MS (Dhib-Jalbut (2002) Neurology, Vol. 58: S3-S9). For instance, the interferons bind to cell surface-specific receptors, initiating a cascade of signaling pathways that end with the secretion of antiviral, antiproliferative, and immunomodulatory gene products. Glatiramer acetate, a synthetic molecule, inhibits the activation of myelin basic protein-reactive T cells and induces a T-cell repertoire characterized by anti-inflammatory effects. Several currently marketed treatments, including IV immunoglobulin (GAMAGARD®, Baxter), methotrexate (RHEUMATREX©, American Cyanamid), and azathioprine (IMURAN®, GlaxoSmithKline), have been evaluated as treatments for relapsing-remitting multiple sclerosis in combination with the approved therapies (Calabresi (2002) Neurology, Vol. 58: S10-S22). Given that the NMDA receptor antagonist memantine (NAMENDA®, Merz) has been shown to prevent the breakdown of and restore the blood-brain barrier and reduce symptoms associated with pathogenesis of EAE in vivo (Paul and Bolton, 2002), the peptide dimers of the present invention can be used alone or in combination with other NMDA receptor antagonists or in addition to interferons or glatiramer acetate for the treatment of MS in humans.

The present invention encompasses a method of treating, preventing or ameliorating the symptoms of rheumatoid arthritis, psoriatic arthritis, ankylosing spondylitis or polyarticular-course juvenile rheumatoid arthritis in a subject in need thereof by administering to the subject at least one ApoE peptide dimer as described herein. Current therapies for arthritis include peptides and proteins that bind with tumor necrosis factor. Etanercept (ENBREL®, Amgen) is a dimeric fusion protein consisting of the extracellular ligand binding portion of the human 75 kd tumor necrosis factor receptor linked to the Fc portion of human IgG1. Adalimumab (HUMIRA®, Abbott) is a recombinant human IgG1 monoclonal antibody. Tumor necrosis factor binding proteins have shown outstanding results in slowing the progression and lessening the symptoms of rheumatoid arthritis and other rheumatic diseases. Thus, the ApoE peptide dimers of the present invention can be used alone or in combination with other drug for the treatment of rheumatic diseases, including for example, rheumatoid arthritis, ankylosing spondylitis, polyarticular-course juvenile rheumatoid arthritis, and psoriatic arthritis.

The present methods and ApoE peptide dimers are also useful in treating, preventing, or ameliorating neurological signs and symptoms associated with chronic neurological disease, including but not limited to Alzheimer's disease (AD) and HIV-associated encephalopathy. The finding by the present inventors that ApoE peptide dimers are particularly potent in suppressing microglial activation provides a role for the peptide dimers of the invention in the treatment of any neurological disease involving microglial activation. For example, microglia express markers of activation in AD, suggesting that crucial inflammatory events in AD involve microglia. Such activated microglia cluster near amyloid plaques (Griffin et al. (1995) J. Neuropath. Exp. Neurol., Vol. 54: 276). Microglia are also activated in epilepsy (Sheng et al. (1994) J. Neurochem, Vol. 63: 1872).

It has been shown that uptake and pathogenic effects of amyloid beta peptide are blocked by NMDA receptor antagonists (Bi et al., 2002). Other studies indicate that anti-inflammatory drugs can delay the onset or progression of AD (Breitner et al. (1995) Neurobiol. Aging, Vol. 16: 523; Rogers et al. (1993) Neurology, Vol. 43: 1609). Thus, the peptide dimers of the present invention can be used alone or in combination with other NMDA receptor antagonists or other known pharmaceuticals and especially anti-inflammatory drugs used for the treatment of AD in compositions and methods for the treatment of AD in humans.

The present invention includes a method of treating, preventing or ameliorating the symptoms of bacterial sepsis in a subject in need thereof by administering to the subject an effective amount of an ApoE peptide dimer of the invention. Monomeric ApoE receptor binding peptides have been shown to protect against LPS-induced production of cytokines in the periphery in an in vivo animal model of sepsis. See U.S. Application Publication No. 2003/0077641 A1, which is herein incorporated by reference in its entirety. Thus, the peptide dimers of the present invention can be used alone or in combination with other known anti-inflammatory cytokines and antibodies in compositions and methods for the treatment of sepsis.

It is known that the inflammatory process mediates an aspect of the atherosclerotic process. See, e.g., Hansson (1994) Basic Res. Cardiol., Vol. 89: 41; Berliner et al. (1995) Circulation, Vol. 91: 2488; Watanabe et al. (1997) Int. J. Cardiol., Vol. 54: 551. ApoE is known to be secreted by macrophages locally at blood vessel walls (although the amount secreted by macrophages in an individual is trivial compared to the amount of ApoE produced by the liver). In the classic model of atherosclerosis, ApoE functions to remove cholesterol from the blood stream and deliver it to macrophages or to the liver. However, it has become apparent that ApoE secreted by macrophages at the blood vessel wall decreases atherosclerotic plaque formation, independent of any lipid metabolism effects. For instance, ApoE-deficient mice are accepted as a model of hypercholesteremia and atherosclerotic disease. Providing ApoE-secreting macrophages to such mice dramatically decreases atherosclerotic plaque formation. Linton et al. (1995) Science, Vol. 267: 1034. Conversely, replacing a wild-type mouse's macrophages with ApoE-deficient macrophages accelerates atherosclerotic changes, even though the animal continues to produce ApoE by the liver. Fazio et al. (1997) Proc. Natl. Acad. Sci., Vol. 94: 4647.

In atherosclerosis, it is hypothesized that ApoE, via a receptor-mediated event, downregulates macrophage activation in the vicinity of blood vessel walls. Such downregulation of macrophage activation interrupts or interferes with the cascade of events associated with atherosclerotic plaque formation, to thereby reduce or slow the formation of atherosclerotic lesions. The cascade of events known to be associated with atherosclerosis includes smooth muscle cell and endothelial cell proliferation, and foam cell formation. Evidence exists that ApoE downregulates each of these processes. ApoE thus affects the presence and progression of atherosclerosis in vivo, independent of its effects on lipids. The progression of atherosclerosis can be assessed by measuring the amount or size of atherosclerotic plaques, or the percentage of the blood vessel blocked by an atherosclerotic lesion, or the rate of growth of such plaques.

Atherosclerosis refers to the thickening of the arterial intima and accumulation of lipid in artherosclerotic plaques. The present invention provides a method of treating atherosclerosis or of reducing the formation of atherosclerotic plaques in a subject in need thereof by administering one or more peptide dimers of the present invention. Conditions that can be treated by the present method include atherosclerosis of the coronary arteries; arteries supplying the CNS, such as carotid arteries; arteries of the peripheral circulation or the splanchnic circulation; and renal artery disease. Administration, such as parenteral administration, can be site-specific or into the general blood stream. In some embodiments, the peptide dimers can be combined with an additional anti-atherosclerotic drug, including HMG-CoA reductase inhibitors, also termed statins. Suitable statins for use in the methods of the invention include, for example, lovastatin (MEV ACOR®, Merck), simvastatin (ZOCOR®, Merck), pravastatin (PRAVACHOL®, Bristol Myers Squibb), rosuvastatin (CRESTOR®, AstraZeneca), fluvastatin (LESCOL®, Novartis) and atorvastatin (LIPITOR®, Warner-Lambert).

The present invention further provides a method of treating, preventing or ameliorating the symptoms of inflammatory bowel disease (IBD), Crohn's disease, or ulcerative colitis in a subject in need thereof by administering an effective amount of at least one ApoE peptide dimer of the invention. In practicing the methods of this invention, the therapeutic peptides and/or derivatives thereof may be used alone or in combination with other active ingredients. If desired, one or more agents typically used to treat inflammatory bowel disease may be used as a substitute for or in addition to the therapeutic peptides in the methods and compositions of the invention. Such agents include biologics (e.g., inflixamab, adelimumab, and CDP-870), small molecule immunomodulators (e.g., VX 702, SCIO 469, doramapimod, RO 30201 195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate and azathioprine) and alosetron.

Suitable subjects benefiting from the compositions and methods of the present invention include male and female mammalian subjects, including humans, non-human primates, and non-primate mammals. Subjects include veterinary (companion animal) subjects, as well as livestock and exotic species.

The examples which follow are set forth to illustrate the present invention, and are not to be construed as limiting thereof.

EXAMPLES

Example 1. The Cytotoxic Activity of ApoE Peptides is Enhanced by Formation of Disulfide Dimers We have previously shown that the addition of a protein transduction domain (PTD), such as an antennapedia peptide, to the apoE-mimetic COG133 peptide (LRVRLASHL-RKLRKRLL (SEQ ID NO: 3)) enhances its anti-inflammatory activity. A series of fusion peptides with COG133 conjugated to a PTD were prepared by chemical synthesis. Notably, we found that COG112 with the sequence RQIKI-WFQNRRMKWKKCLRVRLASHLRKLRKRLL (SEQ ID NO: 1), was effective in suppressing production of NO, TNFα and IL-6 with IC50s of 21 nM, 58 nM, and 12 nM, respectively, in BV2 cells following stimulation with LPS (FIG. 1). These results demonstrate a significant safety window for COG112 where effective suppression occurs at concentrations of 12-58 nM while the LD50 is >120-fold higher at 7 μM.

During the course of testing various compounds for cytotoxicity against CLL cells, we found that COG112 had an ED50 of 220 nM. These data were generated using lot #313 of the COG112 peptide. Upon depletion of the stock of lot #313, we began using a new synthesis of COG112 (lot #411) and discovered that the ED50 was reduced to 1.2 μM. While still being more potent than the apoE-mimetic COG133 lacking the antennapedia PTD, this lot was less active than lot #313.

Figure 2A:
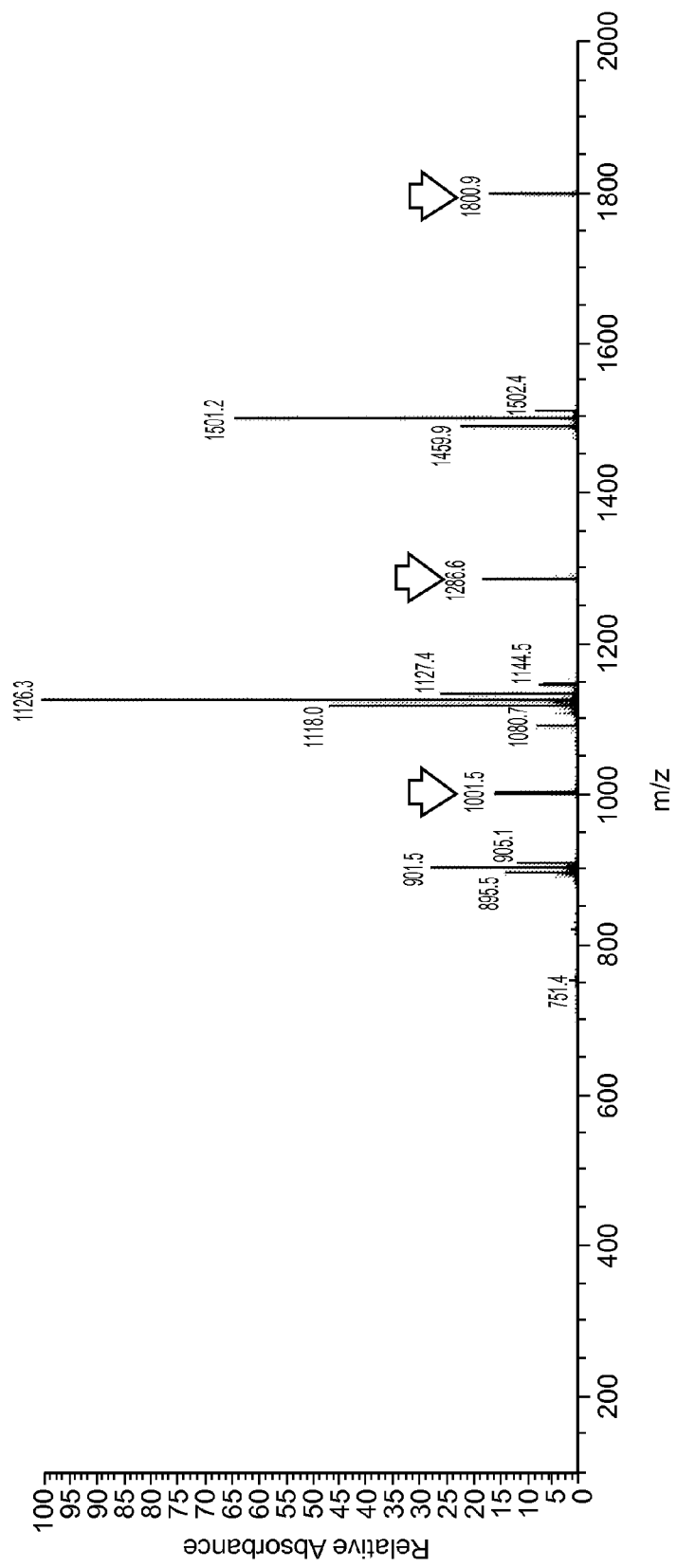
FIGS. 2A-2C. Mass spectra of the original lot #313, reduced, and chemically oxidized COG112. Mass spectra were obtained by LC/MS with electrospray ionization in the positive mode for mass detection.

To determine any possible structural differences in the two lots of COG112, we assayed COG112 from the two different lots using liquid chromatography/mass spectrometry (LC/MS) techniques with electrospray ionization in the positive detection mode. For COG112 from lot #313, a predominant peak with a mass to charge ratio (M/Z) of 1126.3 and peaks at M/Z=1800.9, 1286.6, and 1001.5 were observed (red arrows in FIG. 2A). Upon analysis, the peak at M/Z of 1800.9 arises from the Mass+5 proton form of a dimerized peptide with 5 positive charges (represented as $[M+5H]^{5+}/5$) and the 1286.6 peak arises from the $[M+7H]^{7+}/7$ species. Indeed, the dimer peptide would be expected to have peaks at M/Z=1801.3, 1501.2, 1286.9, 1126.2, 1001.1, 901.1, while the monomer peptide would be expected to give peaks at M/Z=1501.6, 1126.4, 901.3, 751.3, and 644.1.

Figure 2B:
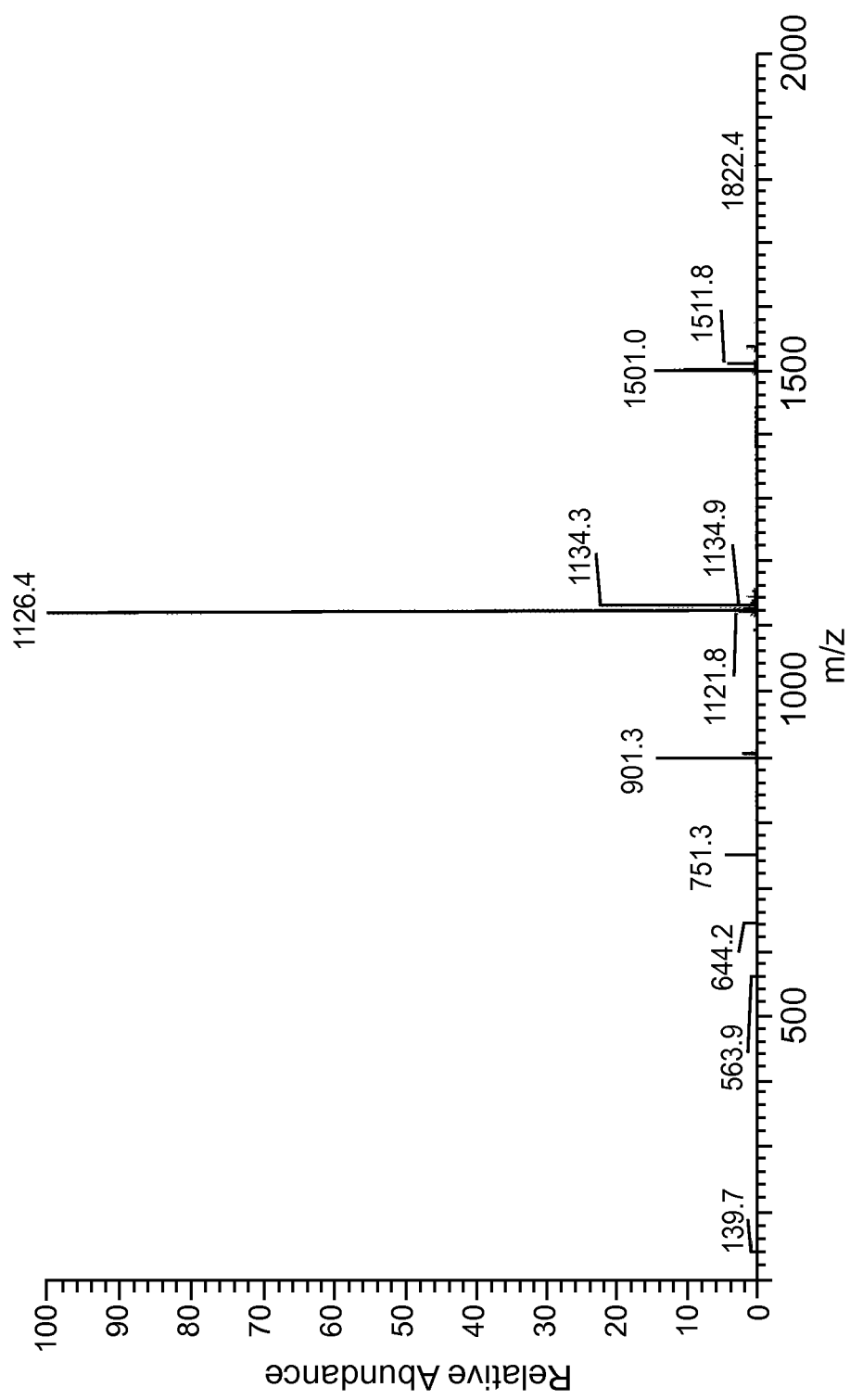
Figure 2C:
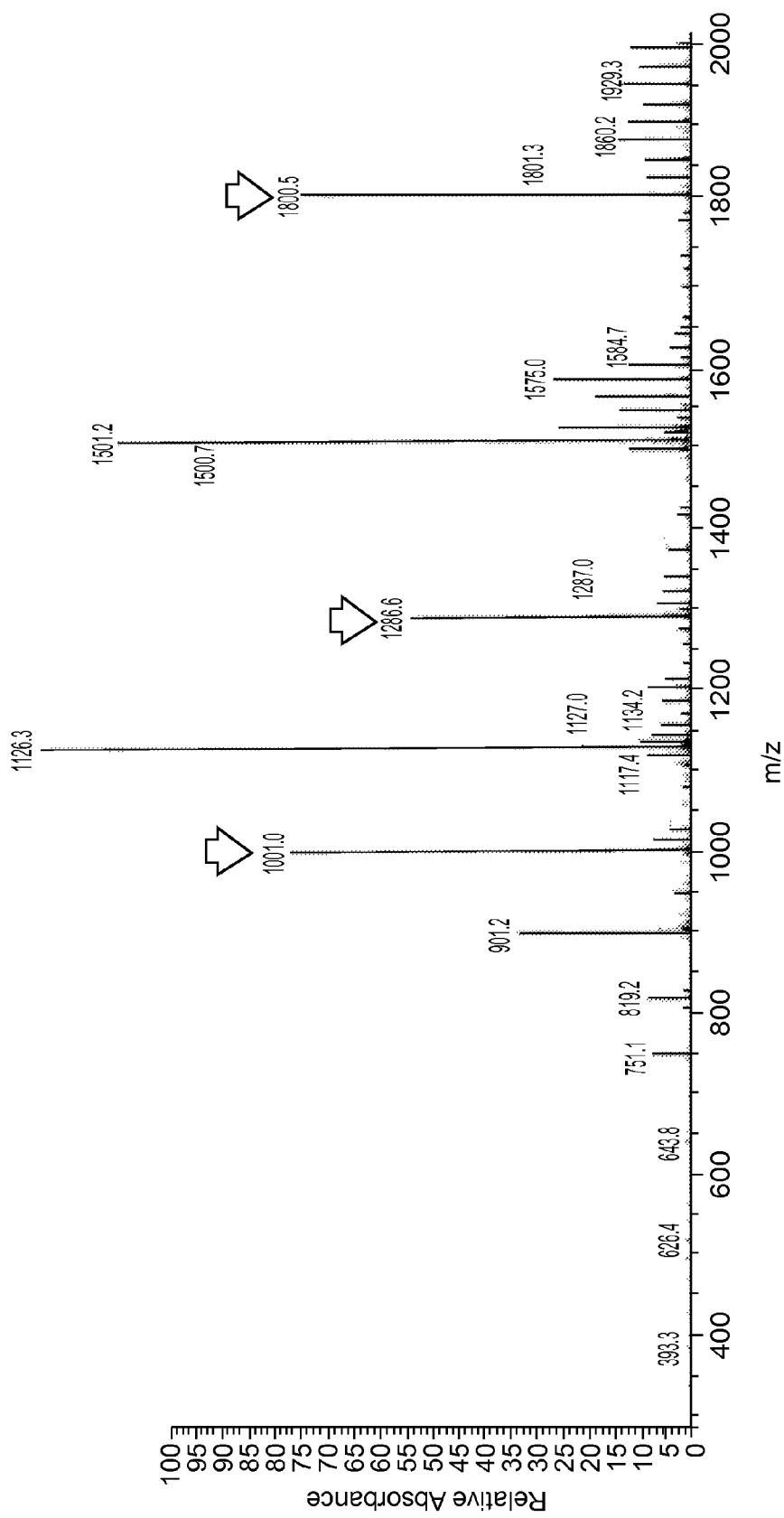

To confirm this finding, we prepared the reduced COG112 by treatment of COG112 from lot #313 with dithiothreitol to reduce the disulfides to the free thiol and repeated the LC/MS analysis (FIG. 2B). In the reduced peptide, peaks of M/Z=1501.0, 1126.4, 901.3, 751.3 and 644.2 were observed in good agreement with the peaks expected from a monomeric peptide. Confirmation that the dimer was the active form of COG112 was accomplished by forcing the formation of the disulfide by stirring the monomer in oxidative conditions and purifying the dimer (also known as COG445 to discern the dimer form from the monomer form of COG112). Analysis of COG445 by LC/MS gave MS peaks of M/Z=1800.5, 1501.3, 1286.6, 1126.1, 1001.0, and 901.2 (FIG. 2C) with the peaks at 1800.5, 1286.6 and 1001.0 being unique to the dimer form of the peptide, thereby confirming the disulfide bridge of this compound.

Having confirmed the dimer structure of COG445, we then evaluated this peptide in both the BV2 cell assay for NO release and the CLL cytotoxicity cell assay. In the BV2 assay, we confirmed an IC50 of 20 nM for NO release and an ED50 of 110 nM for cytotoxicity of CLL cells. In the case of COG445, it is important to note that the previous ED50 values (e.g., 220 nM) were reported using the molecular weight of the monomer of 4502 rather than the actual molecular weight of the dimer of 9004. Adjusting for the correct molecular weight of COG445, the ED50 value for CLL cytotoxicity is reduced to 110 nM.

Figure 3:
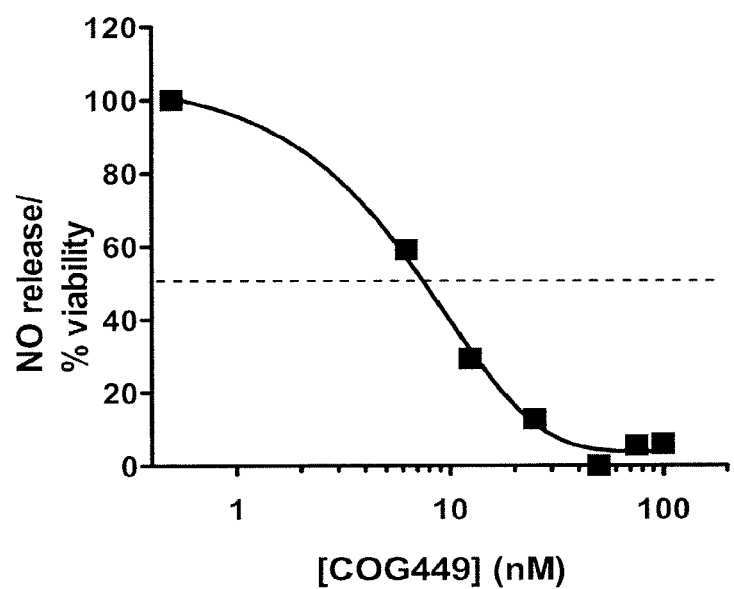
FIG. 3. NO Inhibition curve for COG449. BV2 microglia were treated with COG449 at the final concentrations indicated on the graph, along with 100 ng/mL of LPS. After 24 hours the media was removed and assayed by two-site ELISA (BioSource) and quantitated relative to a standard curve on the same plate.

Example 2. Non-Reducible COG112 Dimer Peptides Activate PP2A and are Cytotoxic to Cancer Cells After discovery that COG112 was active as a disulfide-linked dimer, we sought a method to stabilize the dimer state of COG112. We initially treated the reduced COG112 peptide with a 5-fold molar excess of bismaleimidoethane (BMOE) in dilute solution. The peptide was precipitated by addition of ether, collected by filtration, and the unreacted BMOE removed by washing prior to drying under vacuum. The BMOE-linked peptide was dissolved in buffer and mixed with a 1.5-2.0 molar excess of freshly reduced COG112. Coupling was monitored by HPLC until the reaction was complete and the resultant peptide-BMOE-linker-peptide dimer was precipitated with ether, collected, washed, and purified by reverse phase HPLC to a purity of 98%. The identity of this peptide (known as COG449) was confirmed by MS and was assayed in the BV2 NO release assay. As shown in FIG. 3, we observed an IC50 of 9.4 nM for nitric oxide release from BV2 microglia with COG449, an approximate 2-fold improvement in activity over COG445 (disulfide-linked COG112 dimer).

Figure 4A:
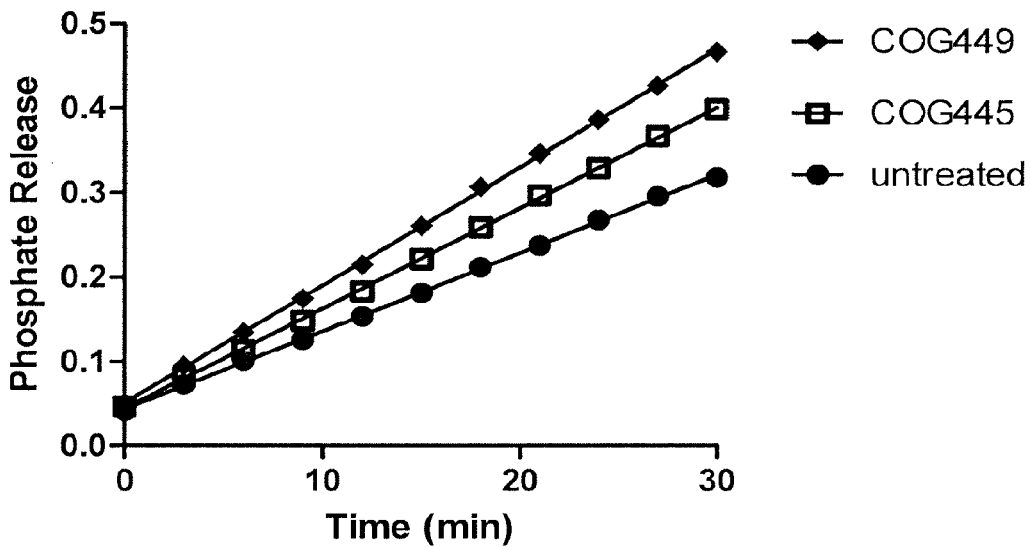
FIGS. 4A-4B. The BMOE-linked dimer peptide COG449 activates PP2A in CML cells.
Figure 4B:
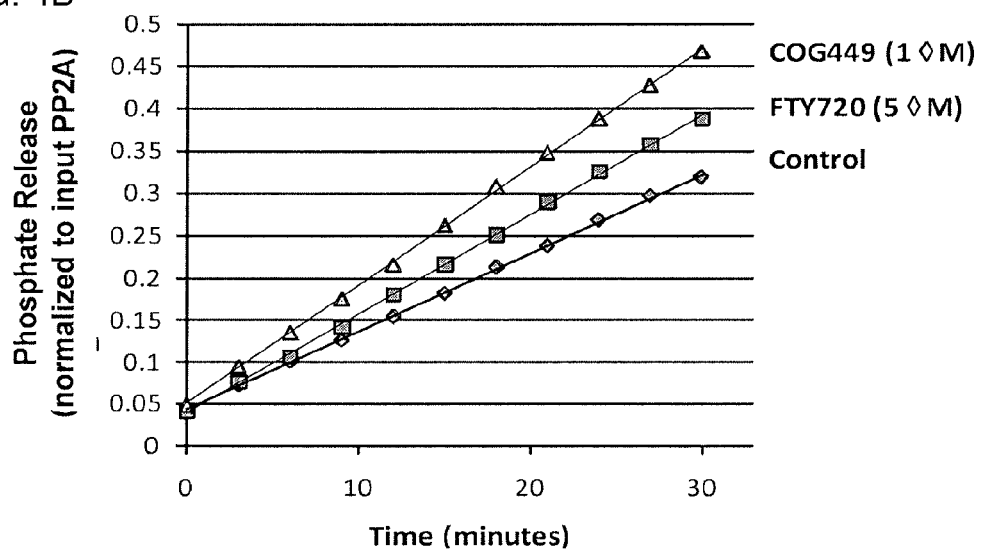

To further evaluate the effect of COG449, we measured the ability of the stable dimerized COG449 compound to activate PP2A in $32D:p210^{BCR/Abl}$ chronic myelogenous leukemia cells. Treatment with either COG445 or COG449 resulted in increased phosphate release due to activation of PP2A relative to untreated control cells (FIG. 4A). However, COG449 treatment increased the rate to a greater extent than COG445, which suggests that COG449 and other stable dimer peptides may be found to have improved potency for killing CLL cells. COG449 also exhibited enhanced PP2A activation compared to FTY720, an agent previously shown to activate PP2A (Neviani et al. (2007) J Clin Invest, Vol. 117: 2408-2421). $32D:p210^{BCR/Abl}$ chronic myelogenous leukemia cells were treated with no compound, 1 µM COG449, or 5 µM FTY720. We observed a robust increase of approximately 45% relative specific activity (phosphate release/minute/unit protein) of PP2A upon treatment with COG449 alone when compared to the untreated control, and about 20% activation compared with FTY720 (FIG. 4B).

Figure 5A:
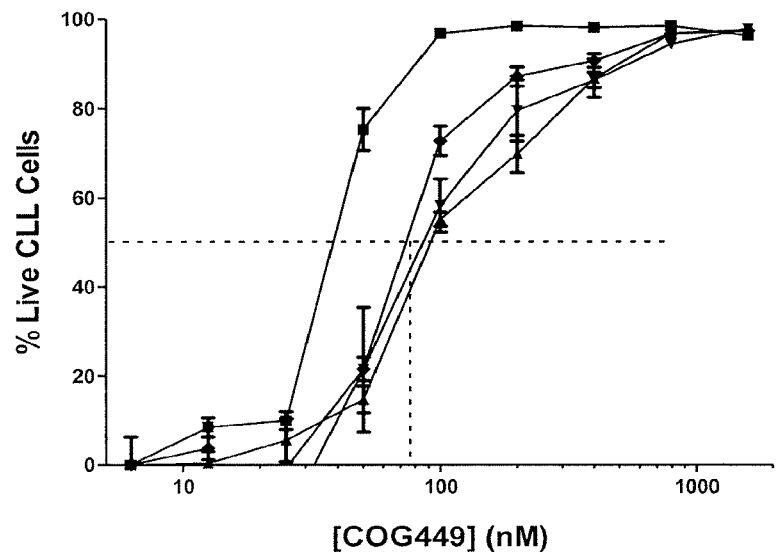
FIG. 5A: Dose response curves for COG449 cytotoxicity on CLL cells from 4 leukemia patients. Human CLL cells were isolated from blood samples and assayed for COG449 cytotoxicity. COG449 was applied to B-CLL cells (0.25×10$^6$ cells/well in a 96 well plate) and after 72 hours, viable cells were assessed using the MTS assay (Pharmacia) to determine the concentration of COG449 that was effective in killing 50% of the input CLL cells (EC50).
Figure 5B:
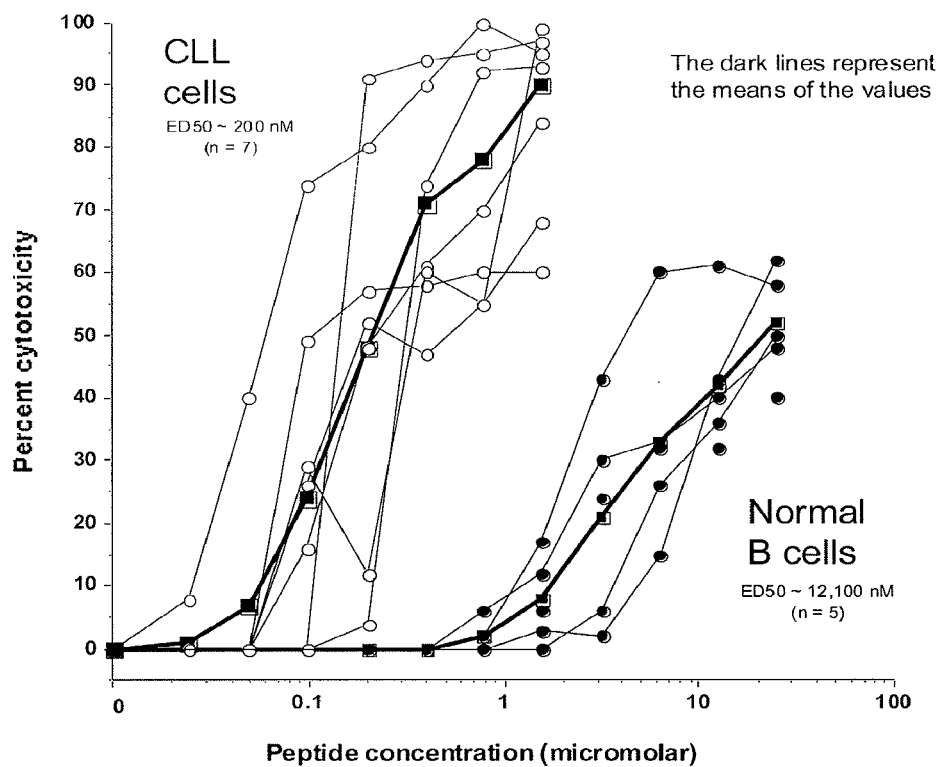
FIG. 5B: Dose response curves for COG445 on CLL cells from 7 patients or normal B-cells from 5 patients. Human CLL cells and PBMC were isolated and assayed for cytotoxicity of COG445.

Based on the activation of PP2A in serum containing media and potent suppression of NO in the BV2 assay, we tested COG 445 and COG449 for cytotoxicity against patient-derived CLL cells and normal B cells (FIG. 5). Blood from CLL patients was collected and CD5+/CD19+ CLL cells were isolated using the RosetteSep™ Human B-Cell Enrichment Cocktail, according to the manufacturer's instructions, and treated with COG compounds. Compounds were applied to B-CLL cells ($2.5 \times 10^5$ cells/well in a 96 well plate), after which the cells were treated for 72 hours. After the treatment period, viable cells were assessed using the MTS assay (Pharmacia) to determine the concentration of COG compound that was effective in killing 50% of the input CLL cells (EC50). Like the values for PP2A activation and NO release, COG449 showed increased potency compared to COG445 as listed in Table I below. The EC50 values for cytotoxicity of normal B-cells from volunteers treated with COG445 and COG449 were nearly 200 fold higher (greater than 10 µM).

In order to more fully understand the role that the PTD domain and the apoE domain of the COG peptides play in anti-CLL cytotoxic activity, we tested additional compounds with an HIV-TAT PTD (COG226) and peptides with altered apoE sequences (COG1410, and COG248) as shown in Table I. It is notable that either the antennapedia (ANTP) or TAT PTD increases potency of COG1410 from 5.7 µM to 1.0 µM and 1.4 µM, respectively. It is also interesting that COG1410 attached to ANTP (COG 120) is more potent as a monomer than the COG112 monomer, with EC50 values of 1.0 µM and 1.4 µM for COG120 and COG112, respectively. This result suggests that creation of dimeric peptides containing altered apoE domains plus the ANTP or TAT PTD domains may further improve the potency of the peptides. These data demonstrate that apoE-mimetic compounds display potent and selective cytotoxic activity for freshly isolated human B-CLL cells with a wide safety margin.

Figure 6A:
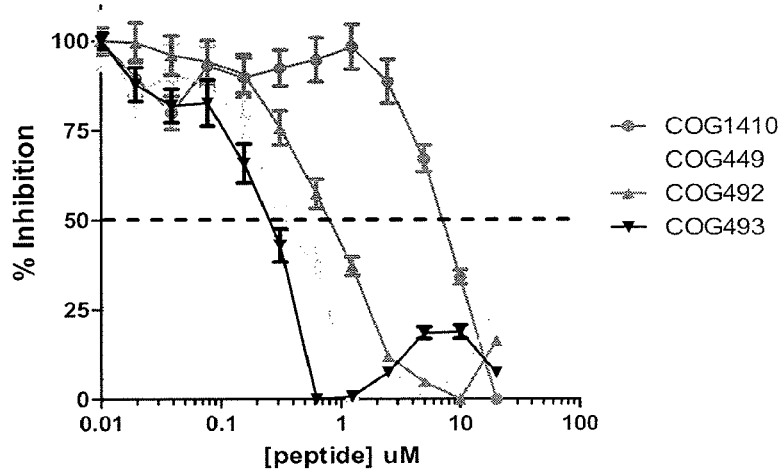
FIG. 6A shows dose response curves for the indicated COG peptides for LPS-induced nitric oxide production in BV2 microglia cells.

We also evaluated the various peptides for efficacy in suppressing nitric oxide production induced by LPS stimulation of BV2 microglia cells as a measure of anti-inflammatory activity as well as the maximum dose tolerated in mice (Table I and FIG. 6A). For the LPS assay, EC50 is the concentration of compound that caused a 50% suppression of nitric oxide release from BV2 cells following LPS stimulation. For mouse toxicity, MTD is the maximum dose of the compound that can be given by intravenous injection without causing deaths after 24 hrs. The ApoE peptide dimers, in particular, exhibited significant potency in the anti-inflammatory assay (FIG. 6A). Coupling the ApoE domain to a protein transduction domain further enhanced the potency of the dimers.

Figure 6B:
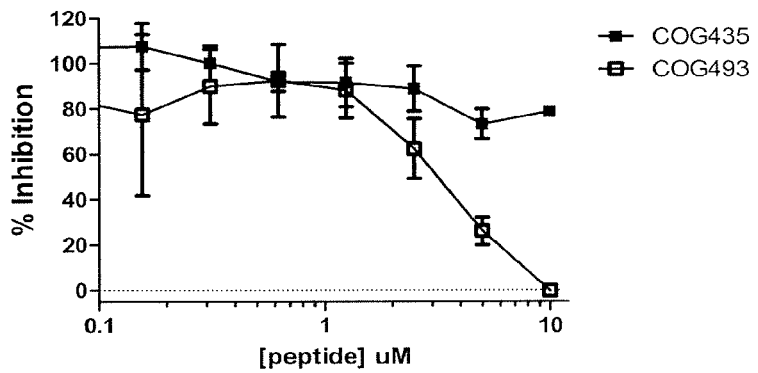
FIG. 6B shows dose response curves for the indicated COG peptides for inhibition of MDA-MB-231 breast cancer cell growth.

Next, we examined the potency of an ApoE peptide dimer versus the monomeric form on proliferation of the MDA-MB-231 breast cancer cell line. MDA-MB-231 cells were treated with various concentrations of either COG435 (monomer; SEQ ID NO: 90) or COG493 (a BMOE-linked dimer of COG 435) peptides for 48 hours. Following peptide treatment, cells were quantified using a MTT assay. The results, shown in FIG. 6B, show that the dimeric form of the ApoE mimetic peptide was significantly more cytotoxic to breast cancer cells than the monomeric form.

Figure 6C:
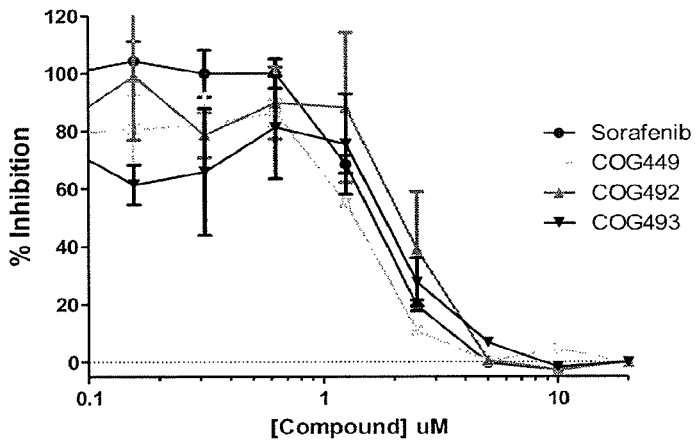
FIG. 6C shows dose response curves for the indicated COG peptides for inhibition of U87MG glioblastoma cell growth.

To determine whether ApoE peptide dimers were cytotoxic to other types of cancer, we evaluated the effect of three different ApoE BMOE-linked peptide dimers (COG449, COG492, COG493; see Table I) on the growth characteristics of U87MG glioblastoma cells. Various concentrations of COG449, COG492, COG493 or Sorafenib were used to treat U87MG glioblastoma cells and viable cells were quanititated using MTT. Sorafenib, which has previously been reported to be cytotoxic to glioblastoma cells (Yang et al. (2010) Mol Cancer Ther., Vol. 9(4):953-962), was used as a positive control. The dose response curve shown in FIG. 6C show that each of the dimeric peptides were cytotoxic to U87MG cells.

This series of experiments demonstrate that ApoE peptides are cytotoxic to three different types of cancer cells. Interestingly, the dimeric form of the ApoE peptides is considerably more potent in inducing cytotoxicity of cancer cells than the monomeric form.

TABLE I

Activity of COG compounds on cancerous B-CLL cells, inflammation, and mouse toxicity

| Compound | Sequence | Form | CLL EC50 (µM) | Fold Change | Normal EC50 (µM) | LPS Assay EC50 (µM) | Mouse MTD (mg/kg) |
|---|---|---|---|---|---|---|---|
| COG056 (rev133) | LLRKRLKRLHSALRVRL (SEQ ID NO: 2) | Monomer | 12.9 ± 4.6 | 1.0 | >20 | >20 | n.d. |
| COG133 | LRVRLASHLRKLRKRLL (SEQ ID NO: 3) | Monomer | 4.4 ± 1.5 | 2.9 | >20 | 8.8 | 16 |
| COG248 | LRVRLAS(Aib)LKRLRK(nitroR)LL (SEQ ID NO: 4) [Aib is amino isobutyric acid and nitroR is a nitroarginine] | Monomer | 2.3 ± 1.3 | 5.5 | >20 | 0.9 | n.d. |
| COG1410 | AS(Aib)LRKL(Aib)KRLL (SEQ ID NO: 5) [Aib is amino isobutyric acid] | Monomer | 5.7 ± 3.0 | 2.3 | >20 | 4.5 | 15 |
| COG226 (TAT-COG1410) | YGRKKRRQRRR-C-AS(Aib)LRKL(Aib)KRLL (SEQ ID NO: 6) | Monomer | 1.4 ± 0.2 | 9.2 | >20 | <1.0 | n.d. |
| COG120 (ANTP-COG1410) | RQIKIWFQNRRMKWKK-C-AS(Aib)LRKL(Aib)KRLL (SEQ ID NO: 7) | Monomer | 1.0 ± 0.2 | 12.6 | >20 | <1.0 | n.d. |
| COG112 (ANTP-COG133) | RQIKIWFQNRRMKWKK-C-LRVRLASHLRKLRKRLL (SEQ ID NO: 1) | Monomer | 1.4 ± 0.7 | 9.2 | >20 | <1.0 | 28 |
| COG445 (disulfide-linked COG112) | COG112-C-C-COG112 [C-C is a disulfide bridge] | Dimer | 0.11 ± 0.08 | 117.3 | >10 | <1.0 | 28 |
| COG449 (BMOE-linked COG112) | COG112-C-BMOE-C-COG112 [BMOE is a bismaleimidoethane linker] | Dimer | 0.077 ± 0.011 | 167.5 | >10 | 0.22 | 12 |
| COG492 (BMOE-linked COG133) | C-LRVRLASHLRKLRKRLL (SEQ ID NO: 15) <BMOE> C-LRVRLASHLRKLRKRLL (SEQ ID NO: 15) [BMOE is a bismaleimidoethane linker] | Dimer | n.d. | n.d. | n.d. | 0.75 | 25 |
| COG435 | WKK-C-LRVRLASHLRKLRKRLL (SEQ ID NO: 90) | Monomer | n.d. | n.d. | n.d. | n.d. | n.d. |
| COG493 (BMOE-linked COG435) | WKK-C-LRVRLASHLRKLRKRLL (SEQ ID NO: 90) <BMOE> WKK-C-LRVRLASHLRKLRKRLL (SEQ ID NO: 90) [BMOE is a bismaleimidoethane linker] | Dimer | n.d. | n.d. | n.d. | 0.17 | 20 |

Example 3. Creation of an ApoE Peptide Dimer Library

Figure 7:
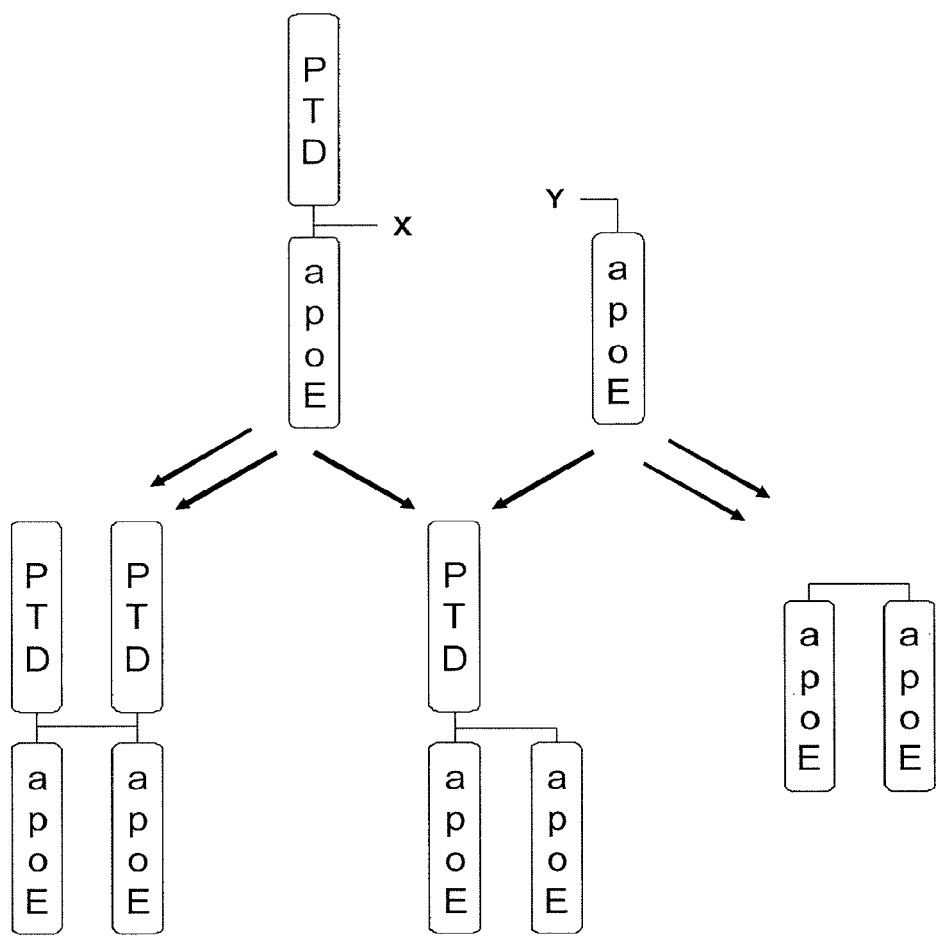
FIG. 7. Schematic representation of the approach to create an ApoE peptide dimer library. PTD=protein transduction domain; ApoE=apoE-mimetic domain; "X" and "Y" represent different linking moieties.

Based on the results demonstrated in Examples 1 and 2 that dimers of ApoE peptides are more potent in inducing cytotoxicity of cancer cells and activating PP2A, twenty eight different monomer ApoE peptides are synthesized that can be coupled with two different coupling chemistries to create a dimer library of sixty four unique compounds. The goal of this Example is to establish a library of chemically stable peptide dimers designed to explore the structure activity relationship between apoE-mimetic peptides and cytotoxicity for CLL cells. Our initial screens with COG peptides were limited to a single dimer peptide, COG112, which has the sequence Ac-RQIKIWFQNRRMKWKKCL-RVRLASHLRKLRKRLL-amide (SEQ ID NO: 1) that contained a disulfide bridge through the cysteine at position 17. This peptide has an antennapedia-derived PTD domain at the N-terminal end and an apoE-mimetic domain in the C-terminal portion such that the dimerized peptide contained two PTD domains and two apoE-mimetic domains. While this dimer of COG112 demonstrated superior potency, it is not possible to determine whether the PTD domain is essential for improved potency or whether a dimer composed of two COG peptides will be sufficient for high potency in cytotoxicity assays. It appears that a PTD does improve cytotoxic potency based on the observation that monomeric COG112 had an ED50 of 1.4±0.7 μM while COG133 that lacks a PTD was three fold less potent with an ED50 of 4.4±1.5 μM (Table I). Based on these results, our strategy for making dimer peptides relies on the combinatorial mixing of peptides that contain a PTD and an apoE-mimetic domain. FIG. 7 illustrates this approach and all peptides in the dimer library contain two apoE-mimetic domains. A series of monomer peptides with reactive groups that can be chemically coupled to create stable dimer peptides is created and combined to make dimer peptides that contain zero, one, or two PTD domains. In order to complete the chemical coupling, we have identified and validated two unique approaches to perform the coupling reactions, namely bismaleimide coupling and click chemistry coupling.

The first method used to create apoE-mimetic dimer peptides utilizes the reaction of a maleimide group with the sulfhydryl group of cysteine. Monomer peptides are created with a single cysteine residue in the peptide monomers and coupled to form a dimer using a bismaleimide linker to create the stable dimer (FIG. 8). Both bismaleimido-ethane (BMOE) and bismaleimido-hexane (BMH) are utilized in the creation of dimers, which allows for bridges of 12 or 16 atoms between the two peptide chains in the dimer peptides. Use of two different length bridging groups allows us to determine the effect of bridging group length on anti-CLL activity. In order to create the bismaleimide linked library, twelve unique monomers are synthesized as listed in Table II. We have selected four unique sequences for the apoE-mimetic domains (COG133, COG1410, COG248, and COG345). COG1410, COG248, and COG345 have previously been shown to exhibit improved anti-inflammatory activity relative to COG133 in NO release assays. An antennapedia PTD (RQIKIWFQNRRMKWKK (SEQ ID NO: 8)) and an HIV TAT PTD (YGRKKRRQRRR (SEQ ID NO: 9)) are used for the PTD domain in the library peptides.

TABLE II

Monomer Peptide Sequences for Bismaleimide Librar Construction

| Designation | Sequence | SEQ ID NO | PTD-domain | apoE-domain |
|---|---|---|---|---|
| A1 | RQIKIWFQNRRMKWKK-C-LRVRLASHLRKLRKRLL | 1 | Antennapedia | COG133 |
| A2 | RQIKIWFQNRRMKWKK-C-AS(Aib)LRKL(Aib)KRLL | 7 | Antennapedia | COG1410 |
| A3 | RQIKIWFQNRRMKWKK-C-LRVRLAS(Aib)LKRLRK(Nitro-Arg)LL | 10 | Antennapedia | COG248 |
| A4 | RQIKIWFQNRRMKWKK-C-LRVRLAS(Aib)LRKLR(K-Ac)RLL | 11 | Antennapedia | COG345 |
| A5 | YGRKKRRQRRR-C-LRVRLASHLRKLRKRLL | 12 | HIV-TAT | COG133 |
| A6 | YGRKKRRQRRR-C-AS(Aib)LRKL(Aib)KRLL | 6 | HIV-TAT | COG1410 |
| A7 | YGRKKRRQRRR-C-LRVRLAS(Aib)LKRLRK(Nitro-Arg)LL | 13 | HIV-TAT | COG248 |
| A8 | YGRKKRRQRRR-C-LRVRLAS(Aib)LRKLR(K-Ac)RLL | 14 | HIV-TAT | COG345 |
| B1 | C-LRVRLASHLRKLRKRLL | 15 | — | COG133 |
| B2 | C-AS(Aib)LRKL(Aib)KRLL | 16 | — | COG1410 |
| B3 | C-LRVRLAS(Aib)LKRLRK(Nitro-Arg)LL | 17 | — | COG248 |
| B4 | C-LRVRLAS(Aib)LRKLR(K-Ac)RLL | 18 | — | COG345 |

Aib = aminoisobutyric acid, K-Ac = Nϵ-Acetyl-lysine, and Nitro-Arg = Nitroguanidinoarginine Following synthesis of the peptides listed in Table II, the peptides are coupled to form dimers using either BMOE or BMH as listed in Table III. In Table III, an X indicates which monomer peptides are coupled together, thereby creating a focused library containing 40 unique members. The initial library is not strictly combinatorial in that only matched apoE sequences are coupled, resulting in dimer peptides that contain two COG133, two COG1410, two COG248, or two COG345 apoE domains. Final compounds that contain two PTD domains and two apoE domains are highlighted in the blue area of the Table, compounds that contain one PTD domain and two apoE domains are highlighted in the yellow area of the Table, and compounds lacking a PTD domain but containing two apoE domains are found in the green area of the Table.

TABLE III

Combinatorial plan for construction of dimer peptides using bismaleimides

| | BMOE | | | | | | | | | | | | BMH | | | | | | | | | | | |
|---|---|---|---|---|---|---|---|---|---|---|---|---|---|---|---|---|---|---|---|---|---|---|---|---|
| | A1 | A2 | A3 | A4 | A5 | A6 | A7 | A8 | B1 | B2 | B3 | B4 | A1 | A2 | A3 | A4 | A5 | A6 | A7 | A8 | B1 | B2 | B3 | B4 |
| A1 | $X^1$ | | | | | | | | $X^2$ | | | | $X^1$ | | | | | | | | $X^2$ | | | |
| A2 | | $X^1$ | | | | | | | | $X^2$ | | | | $X^1$ | | | | | | | | $X^2$ | | |
| A3 | | | $X^1$ | | | | | | | | $X^2$ | | | | $X^1$ | | | | | | | | $X^2$ | |
| A4 | | | | $X^1$ | | | | | | | | $X^2$ | | | | $X^1$ | | | | | | | | $X^2$ |
| A5 | | | | | $X^1$ | | | | $X^2$ | | | | | | | | $X^1$ | | | | $X^2$ | | | |
| A6 | | | | | | $X^1$ | | | | $X^2$ | | | | | | | | $X^1$ | | | | $X^2$ | | |
| A7 | | | | | | | $X^1$ | | | | $X^2$ | | | | | | | | $X^1$ | | | | $X^2$ | |
| A8 | | | | | | | | $X^1$ | | | | $X^2$ | | | | | | | | $X^1$ | | | | $X^2$ |
| B1 | | | | | | | | | $X^3$ | | | | | | | | | | | | $X^3$ | | | |
| B2 | | | | | | | | | | $X^3$ | | | | | | | | | | | | $X^3$ | | |
| B3 | | | | | | | | | | | $X^3$ | | | | | | | | | | | | $X^3$ | |
| B4 | | | | | | | | | | | | $X^3$ | | | | | | | | | | | | $X^3$ |

Figure 9A:
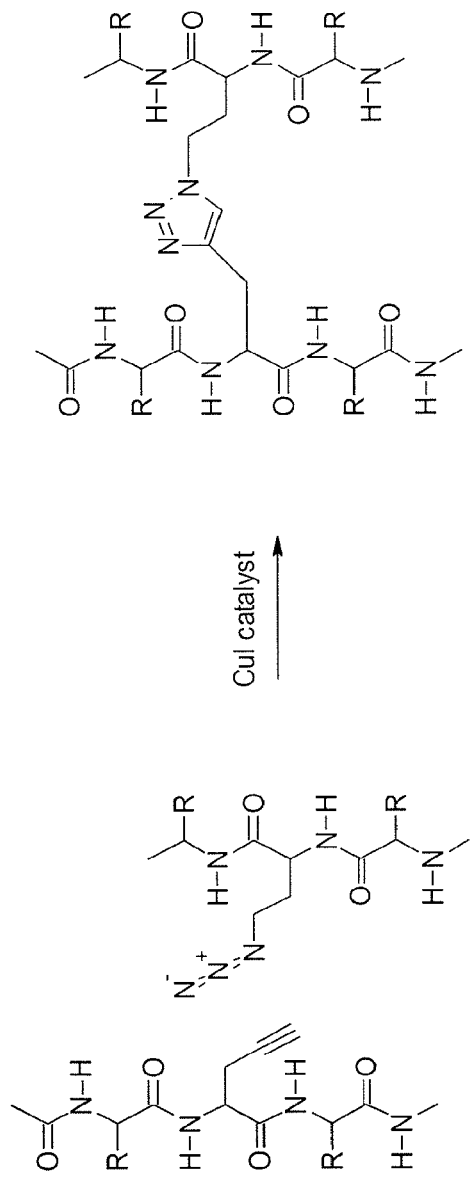
FIGS. 9A-9B. The chemical transformation involved in the "Click Chemistry" reaction. Copper catalyzed 3+2 condensation results in coupling through formation of a stable 1,4-disubstituted triazole.
Figure 9B:
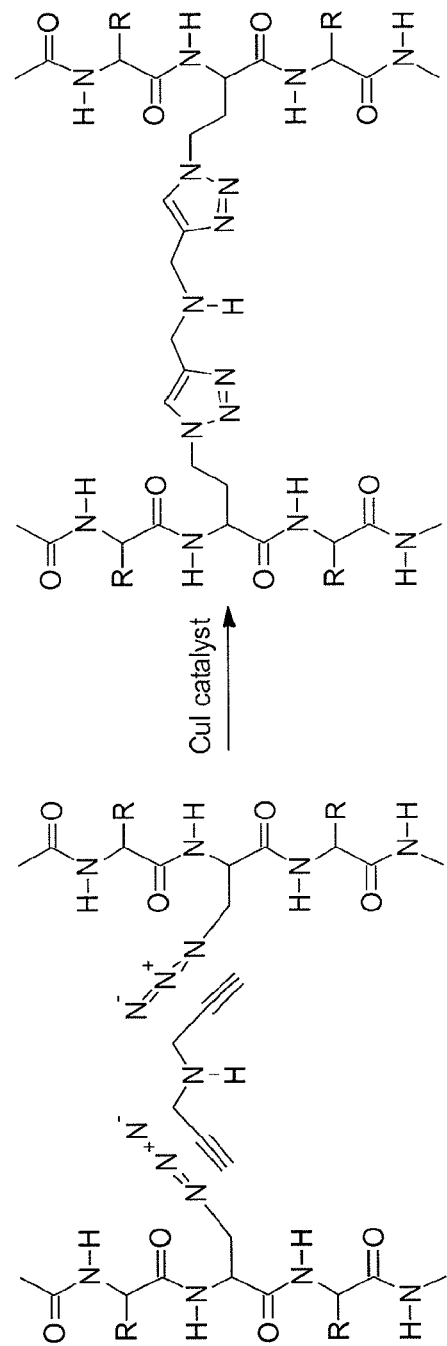

[1]indicates a compound containing two PTD domains and two ApoE domains,
[2]indicates a compound containing one PTD domain and two ApoE domains,
[3]indicates a compound lacking a PTD domain but containing two ApoE domains The second method for coupling of the peptides utilizes "Click" chemistry for coupling the monomers. This coupling method relies on the copper catalyzed 3+2 Huisgen cycloaddition of an azide and a primary alkyne to form a stable 1,4-disubstituted triazole as shown in FIG. 9. The reactive azido and primary alkyne groups are incorporated into peptides during synthesis through commercially available L-azidohomoalanine and L-propargylglycine, respectively. After synthesis of the peptide monomers containing either L-azidohomoalanine or L-propargylglycine, two methods can be used to create dimerized peptides. The first approach is the simple coupling of one monomer containing azidohomoalanine with a propargylglycine-containing monomer using standard reaction conditions (FIG. 9A). This reaction generates a dimer with a short 6 atom bridge between the peptide chains. The second approach utilizes two azidohomoalanine containing monomers that are coupled together through N,N-dipropargylamine (FIG. 9B) to create a 13 atom bridge between the peptide chains. In order to complete the "Click" chemistry library construction, 16 unique monomer peptides are synthesized as listed in Table IV.

TABLE IV

Monomer Peptide Sequences for Click Coupling Library Construction

| Designation | Sequence | SEQ ID NO | PTD-domain | apoE-domain |
|---|---|---|---|---|
| A1 | RQIKIWFQNRRMKWKK-Azh-LRVRLASHLRKLRKRLL | 19 | Antennapedia | COG133 |
| A2 | RQIKIWFQNRRMKWKK-Azh-AS(Aib)LRKL(Aib)KRLL | 20 | Antennapedia | COG1410 |
| A3 | RQIKIWFQNRRMKWKK-Azh-LRVRLAS(Aib)LKRLRK(Nitro-Arg)LL | 21 | Antennapedia | COG248 |
| A4 | RQIKIWFQNRRMKWKK-Azh-LRVRLAS(Aib)LRKLR(K-Ac)RLL | 22 | Antennapedia | COG345 |
| A5 | YGRKKRRQRRR-Azh-LRVRLASHLRKLRKRLL | 23 | HIV-TAT | COG133 |
| A6 | YGRKKRRQRRR-Azh-AS(Aib)LRKL(Aib)KRLL | 24 | HIV-TAT | COG1410 |
| A7 | YGRKKRRQRRR-Azh-LRVRLAS(Aib)LKRLRK(Nitro-Arg)LL | 25 | HIV-TAT | COG248 |
| A8 | YGRKKRRQRRR-Azh-LRVRLAS(Aib)LRKLR(K-Ac)RLL | 26 | HIV-TAT | COG345 |
| B1 | Pgy-LRVRLASHLRKLRKRLL | 27 | — | COG133 |
| B2 | Pgy-AS(Aib)LRKL(Aib)KRLL | 28 | — | COG1410 |
| B3 | Pgy-LRVRLAS(Aib)LKRLRK(Nitro-Arg)LL | 29 | — | COG248 |
| B4 | Pgy-LRVRLAS(Aib)LRKLR(K-Ac)RLL | 30 | — | COG345 |
| C1 | Azh-LRVRLASHLRKLRKRLL | 31 | — | COG133 |
| C2 | Azh-AS(Aib)LRKL(Aib)KRLL | 32 | — | COG1410 |

TABLE IV-continued

Monomer Peptide Sequences for Click Coupling Library Construction

| Designation | Sequence | SEQ ID NO | PTD-domain | apoE-domain |
|---|---|---|---|---|
| C3 | Azh-LRVRLAS(Aib)LKRLRK(Nitro-Arg)LL | 33 | — | COG248 |
| C4 | Azh-LRVRLAS(Aib)LRKLR(K-Ac)RLL | 34 | — | COG345 |

Azh = azidohomoalanine, Pgy = propargylglycine, Aib = aminoisobutyric acid, K-Ac = Nε-Acetyl-lysine, and Nitro-Arg = Nitroguanidinoarginine Following synthesis of the peptides listed in Table IV, the peptides are coupled to form dimers using either the direct Click coupling (FIG. 9A) or via N,N-dipropargylamine coupling (FIG. 9B) using the combinatorial plan shown in Table V. In Table V, an X indicates which monomer peptides are coupled together while the designation Xa or Xb indicates the use of direct Click coupling or via N,N-dipropargylamine Click coupling, respectively, to create the dimerized peptides. This approach generates a focused library containing 24 unique members. Final compounds that contain two PTD domains and two apoE domains are highlighted in the blue area of the Table, compounds that contain one PTD domain and two apoE domains are highlighted in the yellow area of the Table, and compounds lacking a PTD domain but containing two apoE domains are found in the green area of the Table. In the case of the dimers that contain two apoE domains and lacking PTD domains (green area of Table), there are two lengths of linkers between the apoE-mimetic domains. Heterodimerization through direct Click coupling (B1 to C1, B2 to C2, etc.) leads to a shorter 6 atom bridge between the peptide chains and homodimerization using N,N-dipropargylamine results in a longer 13 atom bridge between the peptide chains.

filtration, and unreacted BMOE/BMH is removed by washing prior to drying under vacuum. The BMOE/BMH-linked peptide monomer peptide is dissolved in buffer and mixed with a 1.5-2.0 molar excess of the second monomer peptide. Coupling is monitored by HPLC until the reaction is complete. The resultant peptide is precipitated with ether, collected, washed, purified by reverse phase HPLC to a purity of >90%, and analyzed by LC/MS to determine the molecular mass of the product. Any peptides that do not match the expected mass are rejected and the coupling is repeated.

Click Coupling.

Coupling of the azidohomoalanine and propargylglycine containing peptides is performed using previously described protocols (Chan et al. (2004) Org Lett, Vol. 6(17): 2853-2855). Briefly, equimolar amounts of each monomer peptide are mixed together with copper iodide and ascorbic acid or tris[(1-benzyl-1H-1,2,3-triazol-4-yl)methyl]amine (TBTA). Initially coupling is accomplished with ascorbic acid (Rostovtsev et al. (2002) Angew Chem Int Ed Engl, Vol. 41(14): 2596-2599), but TBTA is used if the ascorbic acid coupling results in poor yield or if damage to the peptide scaffolds is observed. Following coupling, peptides are precipitated with ether, collected and purified by reverse phase HPLC to a purity of >90%. Peptides are analyzed by LC/MS to determine the molecular mass of the product and any peptides that do not match the expected mass are rejected and the coupling is repeated.

TABLE V

Combinatorial plan for construction of Click dimer peptides

|    | A1 | A2 | A3 | A4 | A5 | A6 | A7 | A8 | B1 | B2 | B3 | B4 | C1 | C2 | C3 | C4 |
|----|----|----|----|----|----|----|----|----|----|----|----|----|----|----|----|----|
| A1 | Xb¹ |    |    |    |    |    |    |    | Xa² |    |    |    |    |    |    |    |
| A2 |    | Xb¹ |    |    |    |    |    |    |    | Xa² |    |    |    |    |    |    |
| A3 |    |    | Xb¹ |    |    |    |    |    |    |    | Xa² |    |    |    |    |    |
| A4 |    |    |    | Xb¹ |    |    |    |    |    |    |    | Xa² |    |    |    |    |
| A5 |    |    |    |    | Xb¹ |    |    |    | Xa² |    |    |    |    |    |    |    |
| A6 |    |    |    |    |    | Xb¹ |    |    |    | Xa² |    |    |    |    |    |    |
| A7 |    |    |    |    |    |    | Xb¹ |    |    |    | Xa² |    |    |    |    |    |
| A8 |    |    |    |    |    |    |    | Xb¹ |    |    |    | Xa² |    |    |    |    |
| B1 |    |    |    |    |    |    |    |    |    |    |    |    | Xa³ |    |    |    |
| B2 |    |    |    |    |    |    |    |    |    |    |    |    |    | Xa³ |    |    |
| B3 |    |    |    |    |    |    |    |    |    |    |    |    |    |    | Xa³ |    |
| B4 |    |    |    |    |    |    |    |    |    |    |    |    |    |    |    | Xa³ |
| C1 |    |    |    |    |    |    |    |    |    |    |    |    | Xb³ |    |    |    |
| C2 |    |    |    |    |    |    |    |    |    |    |    |    |    | Xb³ |    |    |
| C3 |    |    |    |    |    |    |    |    |    |    |    |    |    |    | Xb³ |    |
| C4 |    |    |    |    |    |    |    |    |    |    |    |    |    |    |    | Xb³ |

Xa = direct Click coupling,
Xb = Click coupling through N,N-dipropargylamine
[1] indicates a compound containing two PTD domains and two ApoE domains,
[2] indicates a compound containing one PTD domain and two ApoE domains,
[3] indicates a compound lacking a PTD domain but containing two ApoE domains Methods Bismaleimide Coupling.

Coupling of the cysteine containing peptides with bismaleimide compounds is performed as a two step process where a 3-5 fold molar excess BMOE or BMH are initially reacted with the reduced monomer peptide in dilute solution. The peptide is precipitated by addition of ether, collected by

Example 4. Evaluation of ApoE Peptide Dimers

This example outlines experiments designed to evaluate the potency of the peptide dimers from the library described in Example 3. A two step screening cascade is employed. It has previously been shown that high cytotoxicity and leukemia cell apoptosis occur when CLL cells are cultured with nitric oxide synthase (NOS) inhibitors, thereby reducing the concentration of nitric oxide (NO) (Thomas et al. (2008) Free Radic Biol Med, Vol. 45: 18-31). This phenomenon occurs because low to moderate levels of NO are required for maintenance of the anti-apoptotic state of CLL cells (Zhao et al. (1998) Blood, Vol. 92(3): 1031-1043; Levesque et al. (2008) Leuk Res, Vol. 32(7): 1061-70; Kolb et al. (2003) Cardiovasc Haematol Disord, Vol. 3(4): 261-86). Within cells, NO is produced from L-arginine by three NOS isoforms in humans that are encoded by separate genes. NOS1 ("neuronal" NOS) and NOS3 ("endothelial" NOS) generally produce low levels of NO and are constitutively expressed, while inducible NOS (NOS2) is induced by cytokines and microbial factors through activation of NFκB. Like BV2 cells, human cells express NOS2 and produce NO in response to several stimuli including IFN-α, IFN-γ, IL-1, TNFα, IL-6, and LPS (Weinberg (1998) Molecular Med, Vol. 4: 577-591). In human CLL cells, it has been reported that high levels of NOS2 mRNA and protein are constitutively expressed and the cells have high NOS enzyme activity (Zhao et al. (1998) Blood, Vol. 92(3): 1031-1043). Based on these data and the limitations on use of human CLL cells, compounds are initially screened for suppression of NO production in lipopolysaccharide stimulated BV2 microglial cells. This assay is used for the initial screen because BV2 cells grow rapidly and readily express inducible NO synthase (NOS) in response to LPS treatment, leading to measurable amounts of NO production. Therefore, the first screening assay entails treating BV2 cells in an 8 point dose titration curve followed by stimulation with LPS and measuring the ability of the peptide dimers to suppress NO production.

Following determination of the IC50 for NO production in BV2 cells, the twenty peptide dimers with the greatest potency in the NO suppression assay are screened for cytotoxic activity against purified CD19+/CD5+ leukemia cells from CLL patients. Whole blood from CLL patients is obtained and the CD19+/CD5+ CLL cells are isolated by using RosetteSep™ Human B Cell Enrichment Cocktail as described in the methods section below. Unlike homogeneous BV2 cells from culture, it is difficult to obtain enough cells from one patient to screen many peptide dimers with cells from a single patient. Furthermore, due to the diverse nature of CLL with many documented chromosomal abnormalities and phenotypes, it is necessary to screen a single peptide dimer against CLL cells from multiple patients. Therefore, to ensure that pharmacogenomic effects are minimized in this screening step, ED50 values for cytotoxicity of each peptide dimer is determined for CLL cells from not less than six randomly selected patients and the ED50 curves from each individual patient are averaged. Following completion of this screening step, the safety window of each of the 10 most potent peptide dimers from the CLL cell cytotoxicity assays is determined by isolating CD19+ B-cells from normal, age-matched volunteers and determining the ED50 for cytotoxicity of normal B-cells. Similar to the analysis with the CLL cells, the ED50 in B-cell samples is determined from not less than 4 volunteers. A safety window for each peptide dimer is calculated by dividing the ED50 value for cytotoxicity on CLL cells by the ED50 value for cytotoxicity on normal B-cells. The five peptide dimers with the greatest safety window is selected for use in pharmacokinetic profiling.

Pharmacokinetic Profiling of Peptide Dimers

Male C57Bl/6 mice (20-24 g, Charles River, Raleigh, N.C.) are injected with a peptide dimer subcutaneously at a volume of 5 mL/kg in the scruff of the neck. Ten minutes before the desired timepoint, mice are anesthetized and at the desired timepoint blood is drawn by cardiac puncture. Blood from at least 4 mice is used for each timepoint with the samples collected at 5, 10, 15, 30, 45, 60, 90, 120, 180 and 240 minutes for the initial analysis. The samples are processed and the pharmacokinetic analysis is completed. These timepoints were selected based on previous experience with subcutaneously injected COG1410 that shows a dose dependent Tmax of 20-30 minutes and a half life for clearance of 60-90 minutes. In the event that the half life has not been reached, a repeat of the experiment is performed that uses one timepoint before the observed Tmax, a timepoint at the observed Tmax and timepoints extending long enough to adequately determine the half life based on extrapolation of the previous observations of clearance from the plasma. Analysis of three concentrations of the peptide dimer is also performed to determine if there is a dose dependent effect on the pharmacokinetic parameters.

Noncompartmental model analysis is used to estimate pharmacokinetic parameters (Gibaldi and Perrier, 1982) including area under the plasma-concentration time curve from time 0 to time infinity (AUC, 0-∞), peak plasma concentration ($C_{max}$), systemic clearance (CL, which is calculated based on the ratio between the dose and AUC, 0-∞), volume of distribution at steady state (Vss), terminal half-life (t½), which is calculated using a minimum of the last three concentration-time data, and mean residence time in the body (MRT). Data analysis is conducted using WinNonlin professional version 3.1 (Pharsight Corporation, Cary, N.C., USA).

Peptide Dimer Treatment of Eμ-TCL1 Transgenic Mice

Following pharmacokinetic profiling, select peptide dimers are tested in a transgenic mouse model of CLL. Blood is drawn by retro-orbital bleeding from transgenic Eμ-TCL1 mice aged to 9 months for initial analysis to total white cell counts and leukemia cell burden. Animals that show leukemia signs are randomly assigned to treatment groups. At the initiation of treatment, blood is drawn to determine baseline CD5+/CD19+ CLL cell counts and groups of animals (n=20) are subcutaneously injected with a vehicle control (lactated Ringer's solution) or one of the selected peptide dimers at doses and a dose frequency schedule determined by the pharmacokinetic profile data for a total treatment time of 35 days.

Blood is collected from each mouse on a weekly basis by retro-orbital bleeds. This blood is used for determination of total blood leukocyte and lymphocyte counts as well as CD19+/CD5+ cell counts to determine the leukemia burden. After 35 days of treatment, mice are euthanized and the post treatment leukemia burden is measured by cell counting, spleen weight, and histological analysis of bone marrow, spleen, liver, and lymph nodes. All mice dying before 35 days are analyzed in a comparable fashion.

Methods

BV2 Cell Growth, LPS Stimulation and NO Quantitation.

Low passage BV2 microglial cell cultures are maintained in 10% HI (Heat Inactivated) FBS DMEM media (supplemented with MEM NEAA (Non-Essential Amino Acids), sodium pyruvate and Pen-Strep) and continuously cultured until needed. To determine the IC50 values for NO production, peptides are added to BV2 cultures in 1% HI FBS DMEM media (supplemented with MEM NEAA and sodium pyruvate) at a range of final assay concentrations from 1.0 µM in 2 fold dilutions to 7.8 nM followed immediately by addition of LPS (100 ng/mL final concentration) as previously described (Laskowitz et al. (2001) Exp Neurol, Vol. 167(1): 74-85). After incubating for 18±1 hours, conditioned media is removed for analysis of nitrite (the stable oxidation product of released nitric oxide) by the Griess colorimetric assay (Promega). Remaining cells are assayed for viability in an MTT assay (Promega) and the nitrite assay values are normalized for each concentration using the percent viability of cells in the MTT assay. IC50 values for NO inhibition are calculated under the assumption that LPS-only (no peptide added) cultures exhibit a 100% response and no-LPS (no peptide added) cultures exhibit a 0% response. Typically, the absence of LPS exposure to BV2 cells results in levels below the limit of detection in our assays. Similarly, addition of any of the peptides up to 25 µM without LPS results in undetectable NO levels.

CLL Cell Isolation.

Normal B-cells from volunteers and B-CLL cells from patients are isolated using the RosetteSep™ Human B Cell Enrichment Cocktail according to the manufacturer's instructions. This method depletes whole blood of T cells, monocytes, and NK cells using a proprietary antibody cocktail that cross-links unwanted cells in human whole blood to multiple red blood cells (RBCs) forming immunorosettes. This increases the density of the unwanted (rosetted) cells, such that they pellet along with the free RBCs when centrifuged over a buoyant density medium such as Ficoll-Paque®. This leaves the highly enriched B-cell or B-CLL cells at the interface between Ficoll and the plasma. The antibodies in the cocktail contain anti-CD14, anti-CD2 and anti-CD16 antibodies to remove T cells, monocytes, and NK cells, respectively. The purity of these B-cell and B-CLL preparations is then determined by flow cytometry. Preparations typically average less than 2% CD3+ T-cells and less than 0.5% CD14+ monocytes. In the case of B-CLL cell isolation, we routinely obtain preparations that contain less than 1.5% normal CD19+/CD5− B-cells using this method.

CLL Cell Culture/Cytotoxicity Assays.

For cytotoxicity assays, $3 \times 10^6$ CLL cells/well are cultured in 24 well tissue culture plates in 1.5 mL of Hybridoma SFM™ (Gibco, Long Island, N.Y.) as described by Levesque et al. (2001, 2003). All cultures are incubated at 37° C., 5% CO2 in air. Peptide dimers are applied to B-CLL cells ($0.25 \times 10^6$ cells/well in a 96 well plate) and after 72 hours, viable cells are assessed using the MTS assay (Pharmacia) to determine the concentration of peptide dimer that is effective in killing 50% of the input CLL cells (ED50) (Levesque et al., 2003).

Example 5. An ApoE Peptide Dimer Inhibits Akt Signaling in Cancer Cells

Akt signaling is often dysregulated in cancers thereby promoting cellular survival and proliferation. ApoE-based peptides have shown anti-inflammatory effects in various neuropathologies associated with increased Akt signaling. Given the effect of ApoE peptides on other inflammatory pathologies, we investigated the effect of an ApoE peptide dimer on Akt signaling in breast and brain cancer cells. A disulfide dimer of COG112 (SEQ ID NO: 1) was prepared as described in Example 1 (COG445). Adherent breast cancer cells, MDA-MB-231 (MB231), or glioblastoma cells, U87-MG (U87), were serum starved overnight and then exposed to COG445 for 2 hours before stimulating with epidermal growth factor (EGF) for 5 minutes. Western blot analysis showed that COG445 at concentrations up to 1 µM did not alter EGFR activation as determined by EGFR tyrosine 1045 phosphorylation in both U87 (FIG. 10A) and MB231 (data not shown) cell lines. EGFR activation results in the activation of the PI3K/Akt signaling pathway, which is mediated by PDK1 activation. COG445 treatment did not alter PDK1 activation as measured by serine 241 phosphorylation levels in U87 (FIG. 10A) and MB231 (data not shown) cell lines. However, COG445 exposure did result in a dose-dependent decrease of Akt activation in both MB231 and U87 cells (FIG. 10B). Akt serine 473 phosphorylation was decreased in both cell lines at 100 nM and reaches statistical significance at 1 µM COG445.

Figure 11A:
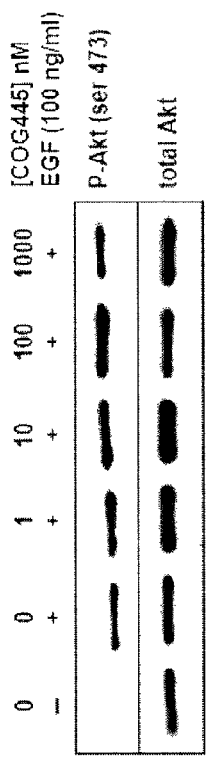
FIGS. 11A-11C. The effect of COG445 on Akt activation is mediated through PP2A.
Figure 11C:
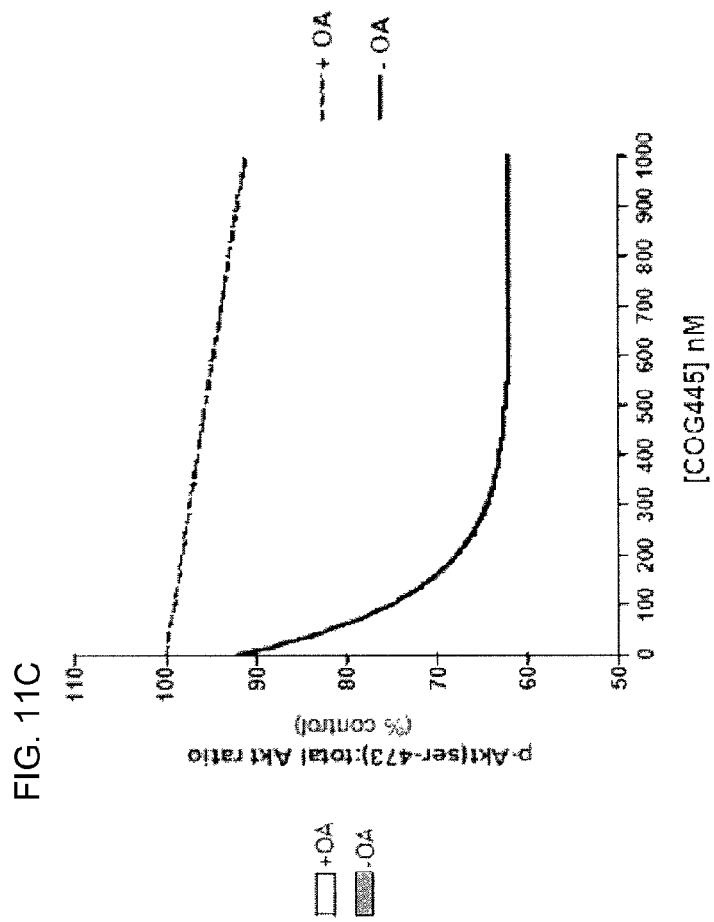
Figure 11B:
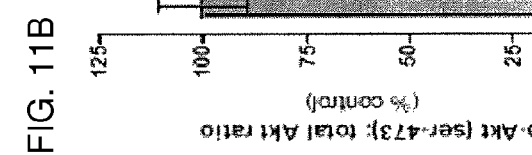

Inhibition of Akt phosphorylation by COG445 appears to be downstream of EGFR/PI3K signaling as EGFR and PDK1 phosphorylation were not altered (FIG. 10A). An endogenous negative regulator of Akt is protein phosphatase 2A (PP2A). To address the potential role of PP2A on COG445 mediated inhibition of Akt, MB231 and U87 cells were exposed to COG445 for two hours in the presence of a PP2A inhibitor, okadaic acid (OA), and then stimulated with EGF. Western blot analysis of MB231 cells shows that COG445 did not inhibit Akt phosphorylation in the presence of OA (FIG. 11A). The difference in Akt phosphorylation between MB231 cells treated with and without OA, in terms of percent of EGF control and with respect to COG445 concentration, is shown in FIG. 11B. At COG445 concentrations ≥100 nM there was a significant difference in Akt phosphorylation, indicating that the inhibition of Akt by COG445 is sensitive to OA. Nonlinear regression analysis further illustrates that COG445 inhibits Akt activation in an okadaic acid sensitive mechanism, consistent with protein phosphatase mediated mechanism of action (FIG. 11C).

Figure 12B:
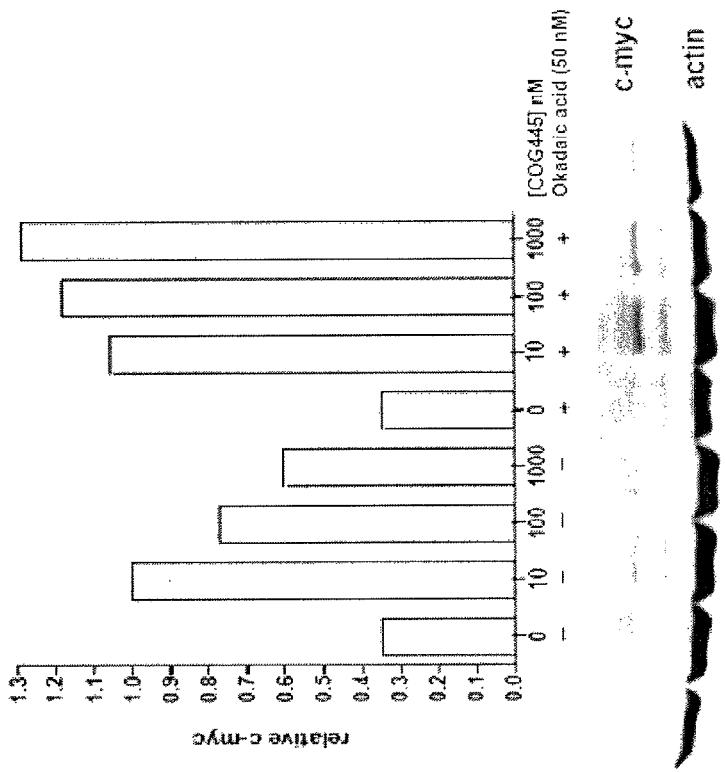
FIG. 12B: Western blot and densitometry analysis of total c-myc protein levels in U87 cells treated with the indicated concentrations of COG445 in the presence or absence of okadaic acid.
Figure 12A:
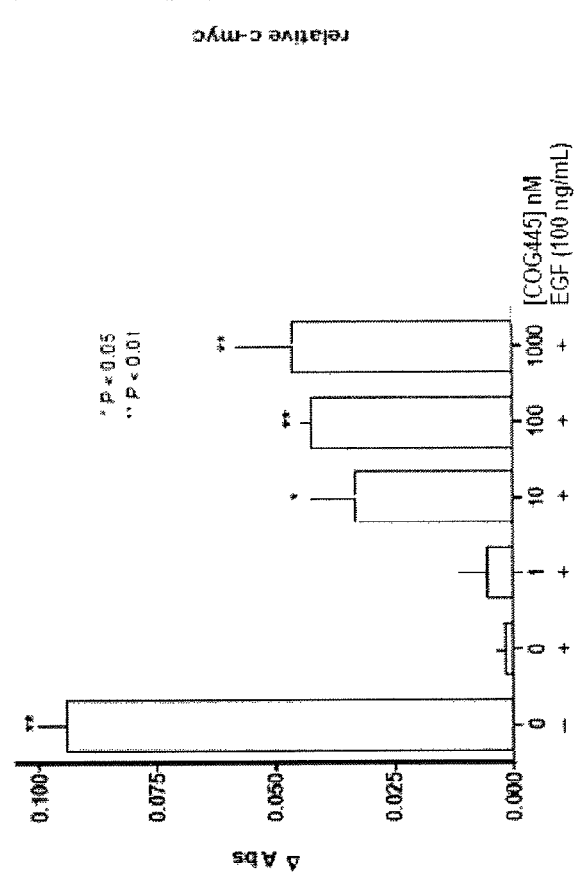
FIG. 12A: Total PP2A activity immunoprecipitated from MDA-MB-231 cells treated with EGF and increasing concentrations of COG445.

To further characterize the effect of COG445 on PP2A activity, MB231 cells were treated as above and the phosphatase activity of immunoprecipitated PP2A was measured. EGF stimulation caused a significant decrease in total PP2A activity compared to untreated serum starved cells (FIG. 12A). Cells treated with COG445 exhibited a significant (P<0.01) increase in PP2A activity at concentrations ≥100 nM. However, the level of PP2A activity did not return to unstimulated control levels. To further explore the extent of PP2A activation in response to COG445, total c-myc protein levels were determined by western blot analysis. C-myc is a substrate for PP2A and upon dephosphorylation is metabolized by ubiquitination and proteasomal degradation. In both U87 (FIG. 12B) and MB231 (data not shown) cell lines, c-myc levels decreased after a two-hour exposure to COG445 in a dose-dependent manner, reaching statistical significance at 1000 nM. Furthermore, c-myc levels are unaltered in response to COG445 in the presence of OA, indicating that PP2A may mediate the decrease in c-myc levels induced by COG445.

Figure 12C:
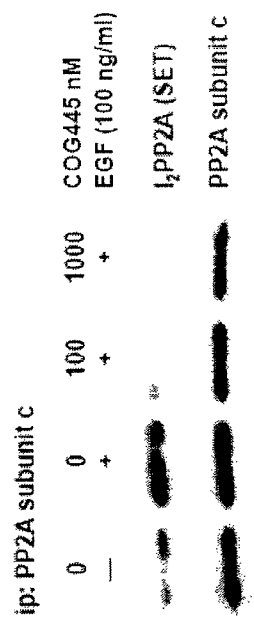
FIG. 12C: Immunoprecipitation of the catalytic subunit of PP2A from MDA-MB-231 cells exposed to EGF and two different concentrations of COG445. The blot is probed for $I_2PP2A$ (SET) and PP2A catalytic subunit.

To examine the mechanism of COG445 on PP2A activity, recombinant human PP2A catalytic subunit was incubated with COG445 and activity was measured. COG445 did not have any effect on the rate of phosphatase activity up to 10 µM (data not shown). These data indicate that COG445 affects PP2A activity on a biochemical level. To further explore the changes of PP2A protein complexes, co-immunoprecipitation experiments were performed on MB231 cells. The potent endogenous inhibitor of PP2A, $I_2PP2A$ (also known as SET), was strongly associated to PP2A in EGF stimulated cells, corresponding to the low PP2A activity, while the association was significantly decreased in unstimulated cells (FIG. 12C). Pre-treatment of the cells with either 0.1 or 1 μM COG445 also strongly diminished the association of I₂PP2A to the catalytic subunit of PP2A (data not shown).

Akt exerts its proliferative signal by phosphorylating protein substrates such as mTOR and GSK-3β. To examine the effects of COG445 on downstream Akt signaling in MB231 cells, mTOR activation and GSK-3β inhibition was measured by western blot analysis. COG445 caused a dose-dependent decrease in mTOR and GSK-3β phosphorylation upon EGF stimulation (FIGS. 13A and B). The phosphorylation of Akt substrates was markedly reduced at COG445 concentration ≥100 nM, corresponding to Akt activation levels. The reduction in mTOR and GSK-3β phosphorylation was eliminated in the presence of okadaic acid, further evidence that PP2A mediates the effects of COG445 on Akt signaling.

Figure 14B:
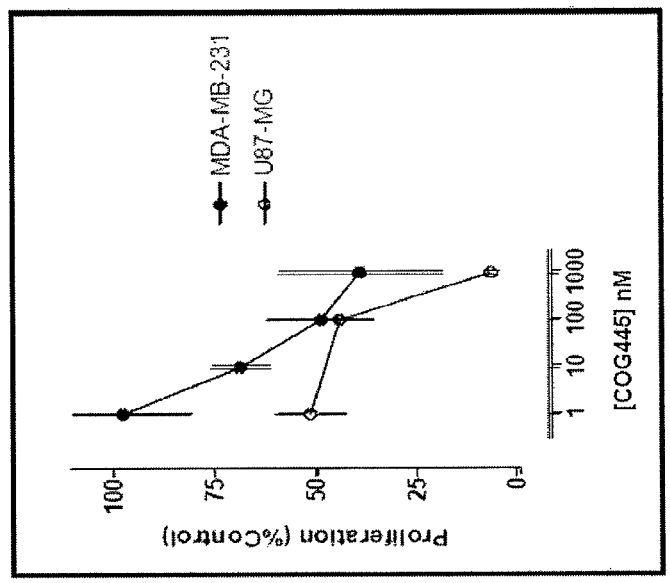
FIG. 14B: Dose response curve of COG445 on proliferation of MDA-MB-231 cells as measured by cell count.
Figure 14A:
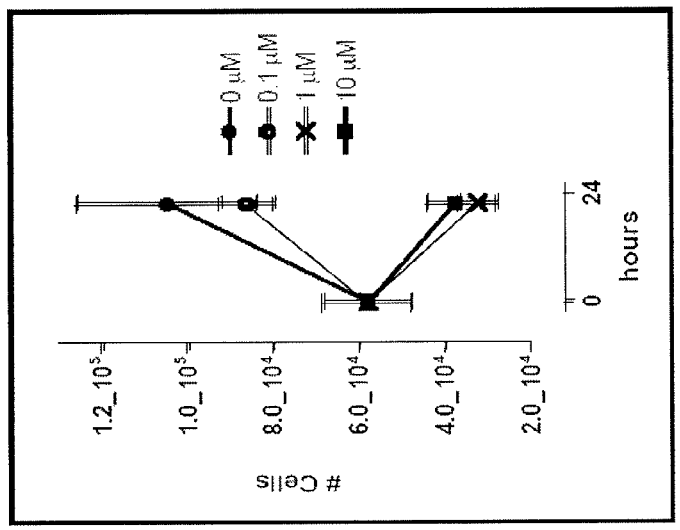
FIG. 14A: Dose response curve of COG445 on proliferation of U87 (open circles) and MDA-MB-231 (filled circles) cells as measured by MTT reduction.

Because COG445 inhibited Akt activation and downstream signaling, we examined the effects of COG445 on cellular proliferation. Adherent MB231 and U87 cells were grown for ~24 hours in the presence of COG445 and cellular proliferation was measured by MTT reduction. COG445 caused a dose-dependent decrease in proliferation for both cancer cell lines tested (FIG. 14A). Furthermore, COG445 inhibited MB231 cellular proliferation as determined by cell count (FIG. 14B). Approximately 6×10⁴ cells were plated in growth media (RPMI+10% FBS) for 24-hours with increasing concentrations of COG445. Incubation of MB231 cells with 0.1 μM COG445 resulted in a slight decrease in cellular proliferation, consistent with the MTT assay data. However at concentrations ≥1 μM COG445, there appears to be a loss of cells. This is partially explained by decreased proliferation, although it is possible that the rate of cellular degradation was increased in the presence of COG445. However, there was no indication of apoptosis after 24 hours in response to 1-1000 nM COG445 administration (data not shown).

The results of these experiments described in this example suggest that ApoE-based peptides may have beneficial effects in cancer chemotherapy by activating the tumor suppressor PP2A.

Figure 15:
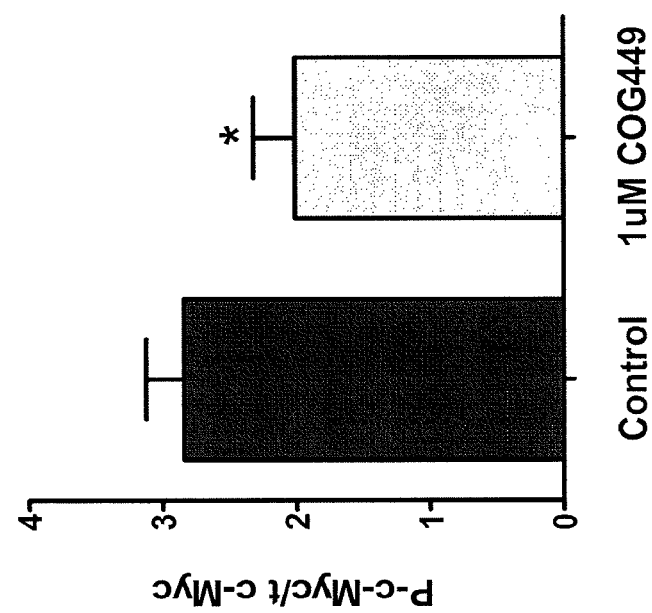
FIG. 15. SET antagonism reduces c-Myc phosphorylation at S62. Raji cells were treated with COG449 or a vehicle control for 20 hrs and lysed. Lysates were analyzed by Western blotting with anti-Phoshpo-S562 and total c-Myc antibodies. * indicates p<0.05.

Example 6. An ApoE Peptide Dimer Reduces C-Myc Phosphorylation in a Burkitt's Lymphoma Cell Line Aberrant c-myc expression has been implicated in various forms of cancer. It has been reported that phosphorylation at serine 62 of c-myc stabilizes the c-myc protein, while dephosphorylation at this serine residue by PP2A directs ubiquitin-mediated degradation of c-myc (see, e.g., Sears et al. (2004) Cell Cycle, Vol. 3: 1133-1137). Because an ApoE peptide dimer increases PP2A activity and promotes c-myc degradation in cancer cell lines (see Examples 2 and 5), we further examined the effect of a stabilized ApoE peptide dimer on c-myc phosphorylation in a c-myc dependent human Raji cell line of Burkitt's lymphoma. We treated Raji cells with COG449, a BMOE-linked dimer of COG112 (see Example 2), or a vehicle control for 20 hr and probed the extracts by Western blotting with an antibody for P-S62 and a total c-myc antibody, which showed a significant reduction of phosphorylation at S62 (FIG. 15).

These results are consistent with those obtained in the experiments described in Examples 2 and 5 and suggest that ApoE peptide dimers can modulate c-myc protein levels in cancer cells perhaps by antagonizing SET and relieving the inhibition of PP2A. Thus, ApoE peptide dimers may represent a new approach to cancer treatment, especially in cancers where SET is overexpressed.

Example 7. SET is Overexpressed in CLL and B-Cell Lymphoma Cells

Figure 16B:
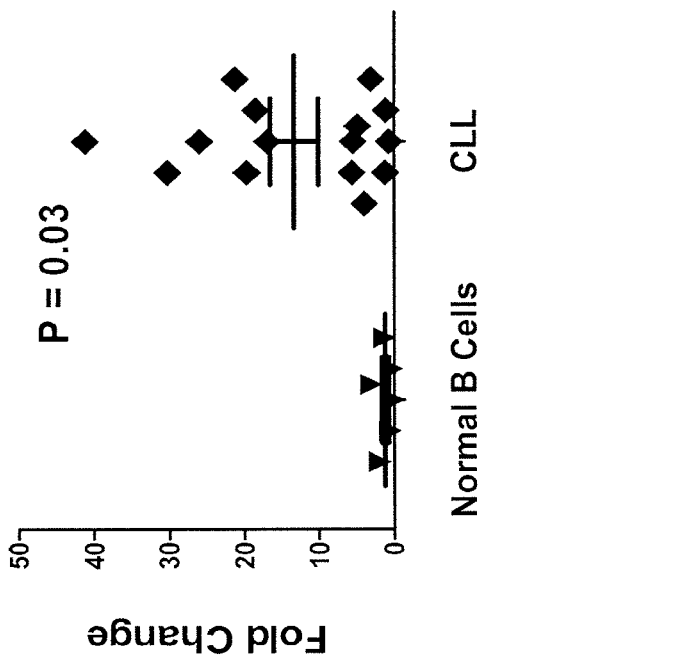
FIGS. 16A-16B. SET is overexpressed in CLL.
Figure 16A:
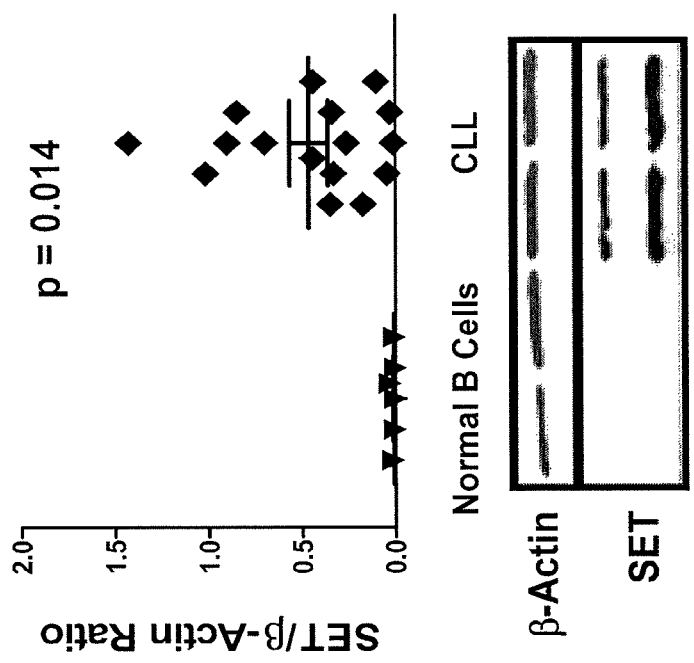

In seeking to study the dysregulation of PP2A in chronic lymphocytic leukemia (CLL), we chose to focus on the endogenous physiological inhibitory proteins of PP2A. Recently, Neviani et al. (Cancer Cell, Vol. 8: 355-68, 2005) reported that the SET oncoprotein (also known as Inhibitor-2 of PP2A, I₂PP2A) was overexpressed in patient-derived chronic myelocytic leukemia (CML) cells and that the SET concentration increased as the patient developed blast crisis. This reference also demonstrated that PP2A activity decreased during blast crisis, resulting in reduced ability of cells to regulate the Akt signaling pathway following BCR/Abl stimulated Akt phosphorylation. Given the convergence of dysregulated Akt signaling in both CML and CLL, we sought to determine whether SET might also be overexpressed in fresh, patient-derived CLL cells. Using primary B-CLL samples from 16 patients and normal B-cells from volunteers, we prepared cell lysates and 40 μg of each lysate was loaded on to a SDS PAGE, transferred to nitrocellulose, and immunoblotting was performed. The bands detected using an anti-SET antibody were quantitated and normalized using β-Actin as a loading control on a LiCor Odyssey fluorescence scanner. We discovered that SET was significantly overexpressed (p<0.05) in the CLL patient samples relative to normal B-cells from volunteers (FIG. 16A). This result was corroborated by determining the expression levels of SET mRNA in patient CLL cells by quantitative PCR (qPCR). The results of this analysis showed statistically significant (p<0.05) higher SET mRNA levels relative to normal B-cells (FIG. 16B). This SET overexpression was independent of apoE genotype or cytogenetic abnormalities of the patients. Documenting SET overexpression in CLL indicates that SET is an important factor in multiple cancers: it is overexpressed in CML (Neviani et al. (2005) Cancer Cell, Vol. 8: 355-68) and diffuse large B-cell lymphoma (Nenasheva et al. (2004) Mol Biol (Mosk), Vol. 38: 265-75). Also in microarray studies of CLL cells, SET upregulation was noted in unmutated IgVH cells (Rosenwald et al. (2001) J Exp Med, Vol. 194:1639-47).

Figure 17A:
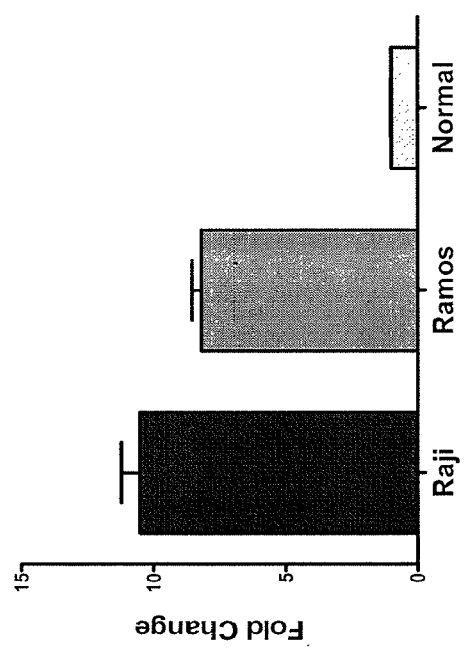
FIGS. 17A-17B. SET is overexpressed in B-cell lymphoma lines.
Figure 17B:
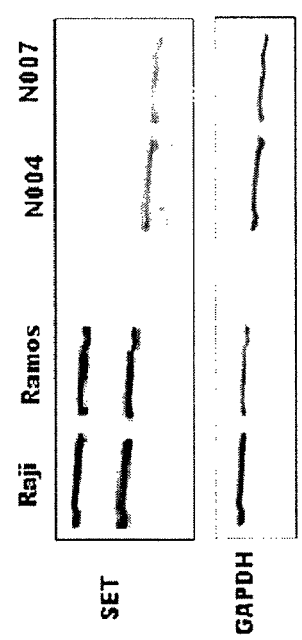

To expand this work, we also evaluated SET overexpression in the Raji and Ramos cell lines of Burkitt's lymphoma, a B-cell Non-Hodgkin's lymphoma (NHL), which unlike CLL cells, is proliferating and can be genetically manipulated. We grew these cells using conditions recommended by ATCC. Cell lysis for Western blotting and isolation of mRNA was performed using standard protocols from 3 separate cultures. Following synthesis of cDNA from the isolated mRNA, qPCR was performed analyzing SET mRNA and 18 S primers and the fold change of the SET expression in Raji and Ramos cells were normalized to that of normal B-cell cDNA expression level (standardized to 1). SET expression levels were 10.5±0.7 fold higher than normal B-cells in Raji cells and 8.2±0.4 for the Ramos cells (p<0.001) (FIG. 17A). Western blotting revealed elevated levels of SET protein as well in Raji and Ramos cells relative to normal B-cell extracts (FIG. 17B). Taken together, these results indicate that overexpression of SET in B-CLL cells and lymphoma cells would decrease PP2A activity and inhibit the ability of PP2A to regulate numerous signaling pathways, such as the Akt-NFκB pathway, the c-Myc oncogene, and the anti-apoptotic Mcl-1 protein, thereby allowing for a pro growth, anti-apoptotic cancerous state to develop in these cells. Thus, SET overexpression may be a key to the maintenance of the cancerous anti-apoptotic state in these cells, and it suggests that antagonism of SET may be an innovative method to treat B-cell malignancies.

Figure 18:
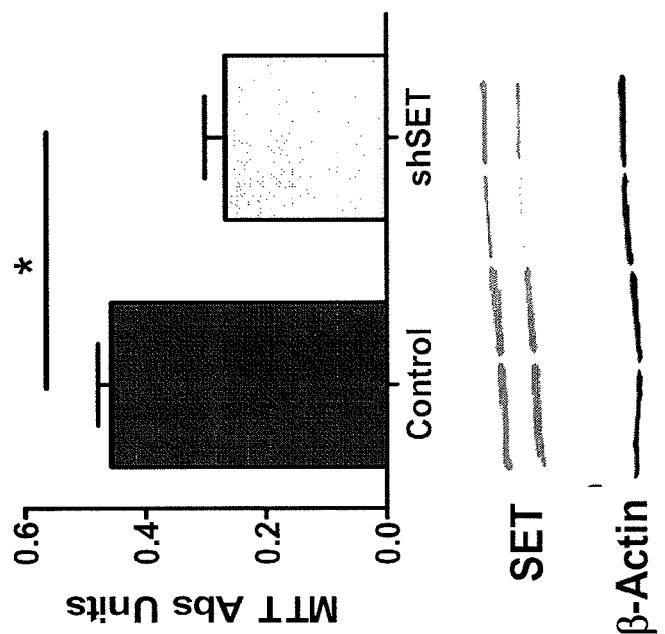
FIG. 18. Silencing of SET inhibits growth of Raji cells. Growth of Raji cells monitored by MTT 72 hr after shRNA for a control or SET was introduced by lentiviral transduction. Western blots show that SET was reduced by about half relative to β-Actin loading controls.

To analyze the effect of reducing the SET activity in cancerous B-cells, we used lentivirus to introduce a shRNA construct to silence SET production in the Raji cell line. When we transduced cells with a SET-specific shRNA construct, the growth rate measured using the MTT assay was significantly decreased relative to a noncoding control shRNA construct (FIG. 18). The SET-specific shRNA construct produced a reduction of the cellular SET levels by approximately 50% relative to the β-Actin loading control protein in Western blots.

Figure 19:
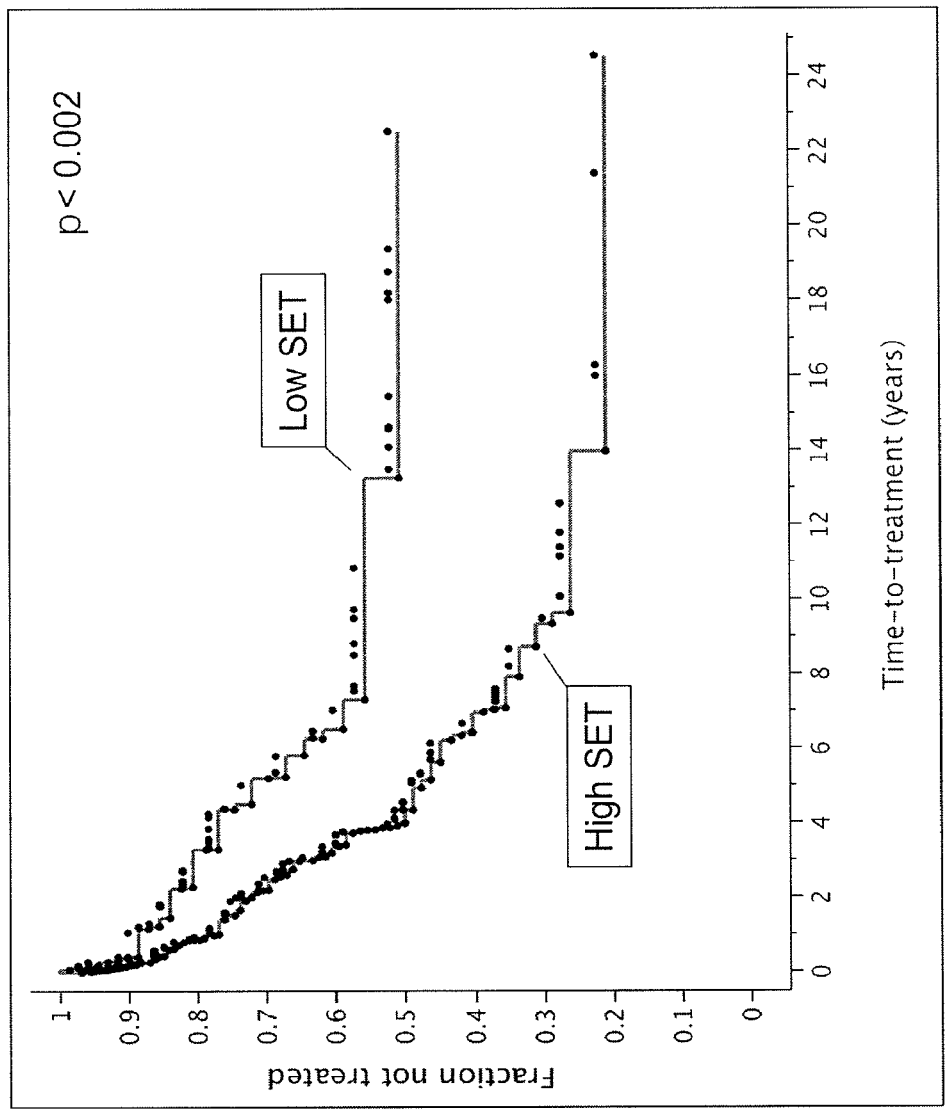
FIG. 19. SET levels may be predictive of CLL disease progression. The time from diagnosis to first needed treatment (the "time-to-treatment") was assessed relative to CLL cell SET level determined by immunoblot. Patients with high levels were compared to those with lower levels (determined by receiver operating characteristics) and had a statistically significantly shorter time-to-treatment (n=226; p<0.002).

To determine if SET levels are indicative of more rapid CLL disease progression, we used Western blotting to quantify SET levels in cell extracts from 226 of the 435 patients in our repository. We created a receiver operator curve to determine a cutoff for high and not-high SET levels. Analysis of the time to first treatment for each of these two groups showed a significant difference—the group with highest SET levels had a reduced time to first treatment relative to patients with lower SET levels (FIG. 19). This preliminary result supports our hypothesis that high CLL SET levels render CLL more aggressive.

Overall, our data demonstrate that SET is overexpressed in CLL and NHL relative to normal B-cells and that antagonism of SET function by reducing its level in cells inhibits growth. Furthermore, our results indicate that measurement of the overexpression of SET from CLL cells or biopsied NHL tissue might be a useful biomarker to predict which patients may require therapy sooner and which patients may benefit from anti-SET therapy, such as ApoE peptide dimers described herein.

Example 8. ApoE Peptide Dimers Reduce Cellular Concentrations of the Anti-Apoptotic Mcl-1 Protein The Myeloid Cell Leukemia-1 (Mcl-1) protein is a member of the Bcl-2 family that regulates apoptosis. Members of this family include the anti-apoptotic members Bcl-2, Bcl-XL and Mcl-1 while pro-apoptotic members include BAD, BID, and BAX (Buggins and Pepper (2010) Leuk Res, Vol. 34: 837-842). The anti-apoptotic Bcl-2 family members associate with pro-apoptotic family members to inhibit mitochondrial outer membrane permeabilization that releases cytochrome-C and initiates the intrinsic apoptotic pathways. CLL cells have been shown to overexpress both Bcl-2 and Mcl-1 (Buggins and Pepper (2010) Leuk Res, Vol. 34: 837-842) and high levels of Bcl-2 and Mcl-1 correlate with poor response to fludaribine therapy in patients (Kitada et al. (1998) Blood, Vol. 91: 3379-8947). Mcl-1 overexpression was demonstrated to arise from B-cell receptor (BCR) engagement and that stimulation of BCR may promote selection of neoplastic B-cell clones (Stevenson and Caligaris-Cappio (2004) Blood, Vol. 103: 4389-9548).

Recently, Peppers et al. measured Mcl-1, Bcl-2, and BAX levels from 185 CLL patients and found that patients with high Mcl-1 levels and low BAX levels, giving rise to a high Mcl-1/BAX ratio had significantly shorter time-to-first-treatment and lower overall survival than patients with lower Mcl-1 levels and ratios between Mcl-1 and BAX (Pepper et al. (2008) Blood, Vol. 112: 3807-3817). In addition to CLL, Mcl-1 overexpression had been reported in B-cell non-Hodgkin's lymphoma (NHL) patients and the expression level correlated with tumor grade where higher expression levels were found in high grade lymphomas (Cho-Vega et al. (2004) Hum Pathol, Vol. 35: 1095-1100). Taken together, these data have been used to suggest that Mcl-1 is the most significant anti-apoptotic protein associated with B-cell malignancies (Gandhi et al. (2008) Blood, Vol. 112: 3538-4051).

Figures 20A, 20B:
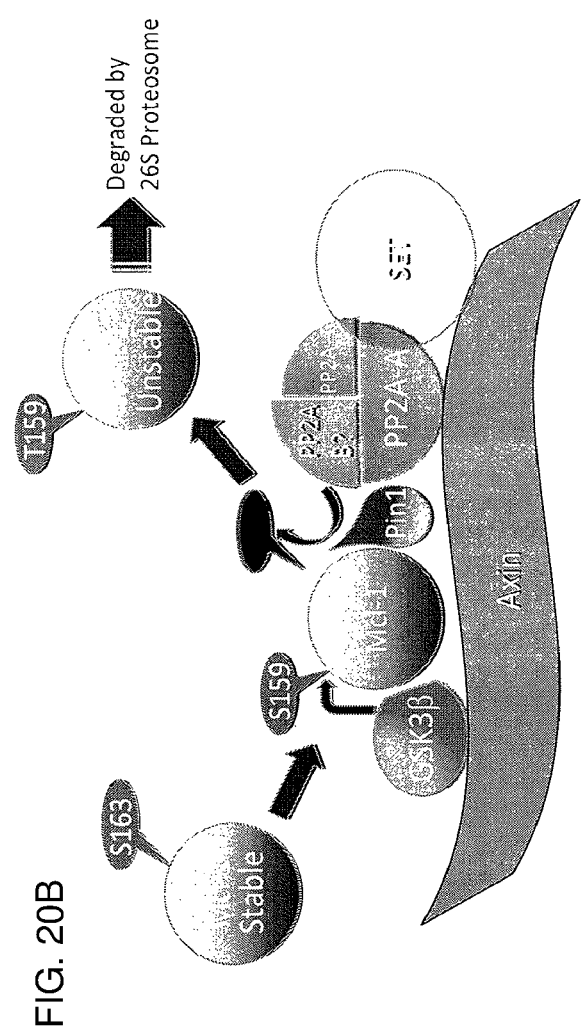
FIGS. 20A-20B. Proposed regulatory mechanisms of Mcl-1 stability.
Figure 21B:
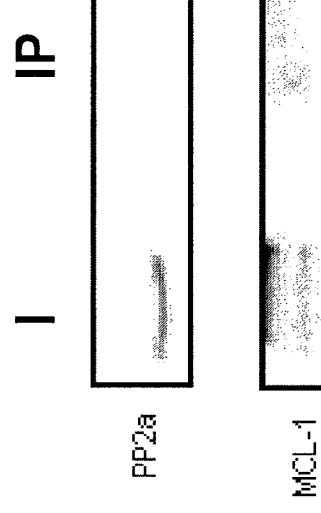
FIGS. 21A-21D. Co-Immunoprecipitation of Mcl-1 associated proteins that may regulate Mcl-1 stability. "I" indicates lanes with input loading control and "IP" indicates immunoprecipitation lanes.
Figure 21A:
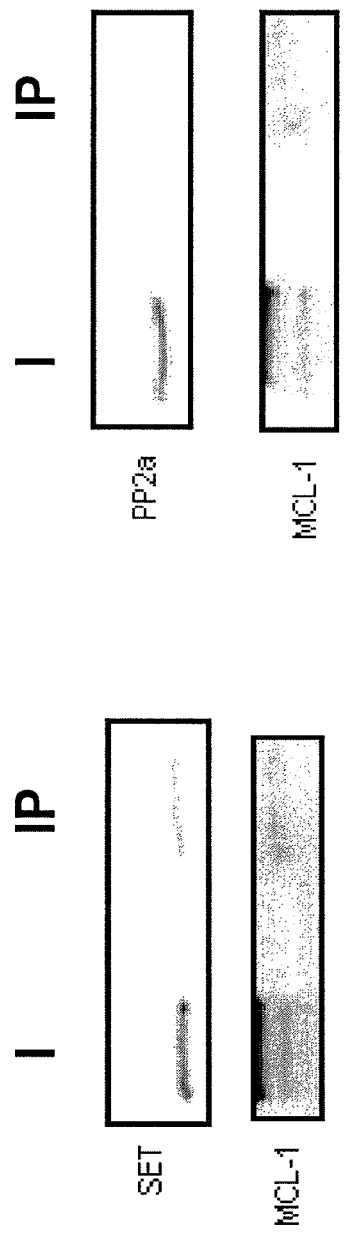
Figure 21D:
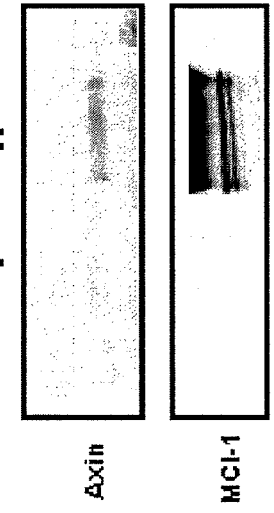
Figure 21C:

Given our results with destabilization of c-myc (see Examples 5 and 6), we began our evaluation of the Mcl-1 protein by analyzing the sequence of c-myc near the T58 and S62 sites that regulates the ubiquitination and proteosomal degradation process and compared this sequence to the Mcl-1 sequence. We observed that there is distinct homology between the c-myc and Mcl-1 motifs with S/T residues at 159 and 163 in Mcl-1 that correspond to the T58 and S62 residues of c-myc as indicated by red arrows in FIG. 20A. Furthermore, there is a proline residue at position 163 in Mcl-1 that corresponds to the proline-63 in c-myc (represented by the purple chevron in FIG. 20A). Based on this overlap in sequences between the regulatory region of c-myc and the sequence of Mcl-1, we hypothesized that a similar regulatory mechanism exists for degradation of Mcl-1. This mechanism would rely upon phosphorylation of T163 followed by GSK3β-mediated phosphorylation of S159 prior to Pin1-mediated proline isomerization at P164. After proline isomerization, T163 would be dephosphorylated by PP2A and the pS159-Mcl-1 protein would then be ubiquitinated and degraded by the proteosome (FIG. 20B). Furthermore, we propose that the regulatory complex would utilize Axin as a scaffolding protein in the same manner as c-myc (FIG. 20B).

To test this hypothesis, we performed immunoprecipitation of Mcl-1 from human CLL cells and checked for co-immunoprecipitation of Pin1, PP2A, Axin, and SET (FIG. 21). Pin1, Axin, and PP2A have all been reported to co-immunoprecipitate with c-myc (Arnold et al. (2009) EMBO J, Vol. 28: 500-512) and each of these proteins were observed to com-immunoprecipitate with Mcl-1. It was also notable that we observed SET in the Mcl-1 immunoprecipitated protein (FIG. 21). It was previously been reported that GSK3β co-immunoprecipitates with Mcl-1 (Ding et al. (2007) Cancer Res, Vol. 67: 4564-4571). Based on the report from Ding et al. and our observations, we have shown that all six of the proteins in the regulatory complex proposed in FIG. 20 have been co-immunoprecipitated with Mcl-1. These data also suggested that antagonism of SET in this complex would increase PP2A activity allowing for dephosphorylation of GSK3β, which was shown to be inversely correlated with Mcl-1 stability, leading to phosphorylation of S159, P164 isomerization, and pT163 dephosphorylation. Following T163 dephosphorylation, ubiquitination and proteosomal degradation of Mcl-1 would reduce the Mcl-1 levels in the cell and allow for activation of apoptosis.

Figure 22:
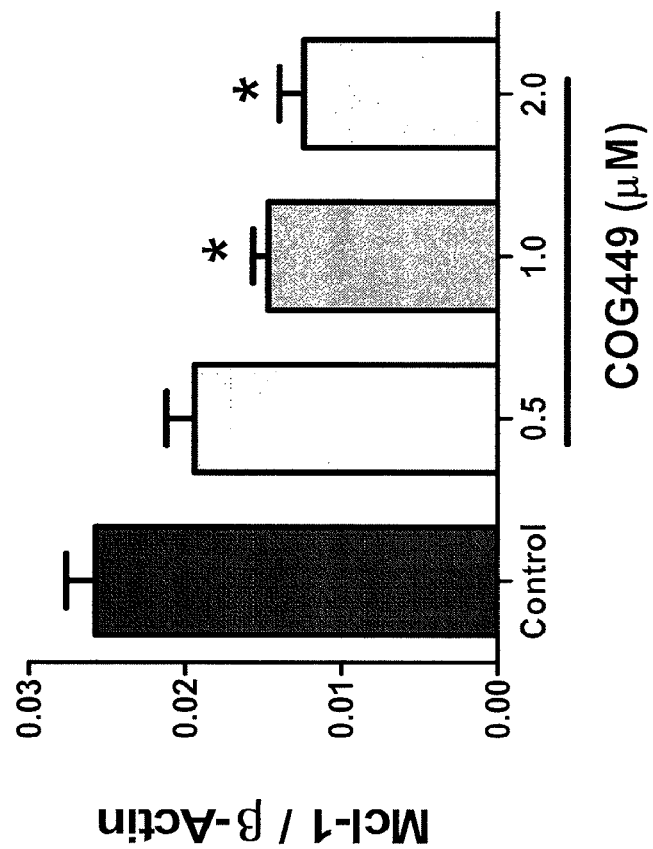
FIG. 22. SET Antagonism reduces cellular Mcl-1 concentrations. Primary human CLL cells were plated and incubated with the indicated concentrations of COG449 for 24 hrs. Cells were lysed, subjected to PAGE and immunoblotted to quantify the Mcl-1 and β-Actin ratio (* indicates p<0.01).

We next sought to determine whether SET antagonism would destabilize Mcl-1. Destabilization of Mcl-1 by treatment with SET antagonists was evaluated by treating primary human CLL cells for 24 hr with the ApoE peptide dimer COG449 (a BMOE-linked dimer of COG112; see Example 2) and evaluating the level of Mcl-1 in the cells. We observed a significant dose-dependent decrease in the Mcl-1 concentration relative to β-Actin as a loading control (FIG. 22). This effect indicates that treatment with COG449 should induce apoptosis in CLL cells and we observed a dose dependent increase in Annexin-V staining with an EC50 of approximately 110 nM (data not shown). These results are consistent with the cytotoxic effects of COG449 and other ApoE mimetic peptides on primary human CLL cells observed in Example 2.

Example 9. ApoE Peptide Dimers Inhibit Growth of Tumor Cells In Vitro and In Vivo To evaluate the effect of COG449, an ApoE peptide dimer (see Example 2), on cancer cell growth in vivo, we analyzed the effects of COG449 treatment of the Ramos cell line of Burkitt's lymphoma, a B-cell non-Hodgkin's lymphoma. Ramos cells are B-cells that overexpress c-myc and form tumors throughout the body. After determining that COG449 inhibited growth with an EC50 of 125 nM in culture, $10^7$ Ramos cells were subcutaneously injected into the left flank of female SCID mice (Schliemann et al. (2009) Blood, Vol. 113: 2275-2283). Tumor growth was monitored daily by palpitation and caliper measurement until tumors reached approximately 150 mm$^3$. At day 11, mice were assigned to two groups so that initial tumor size was approximately equal between groups.

Figure 23:
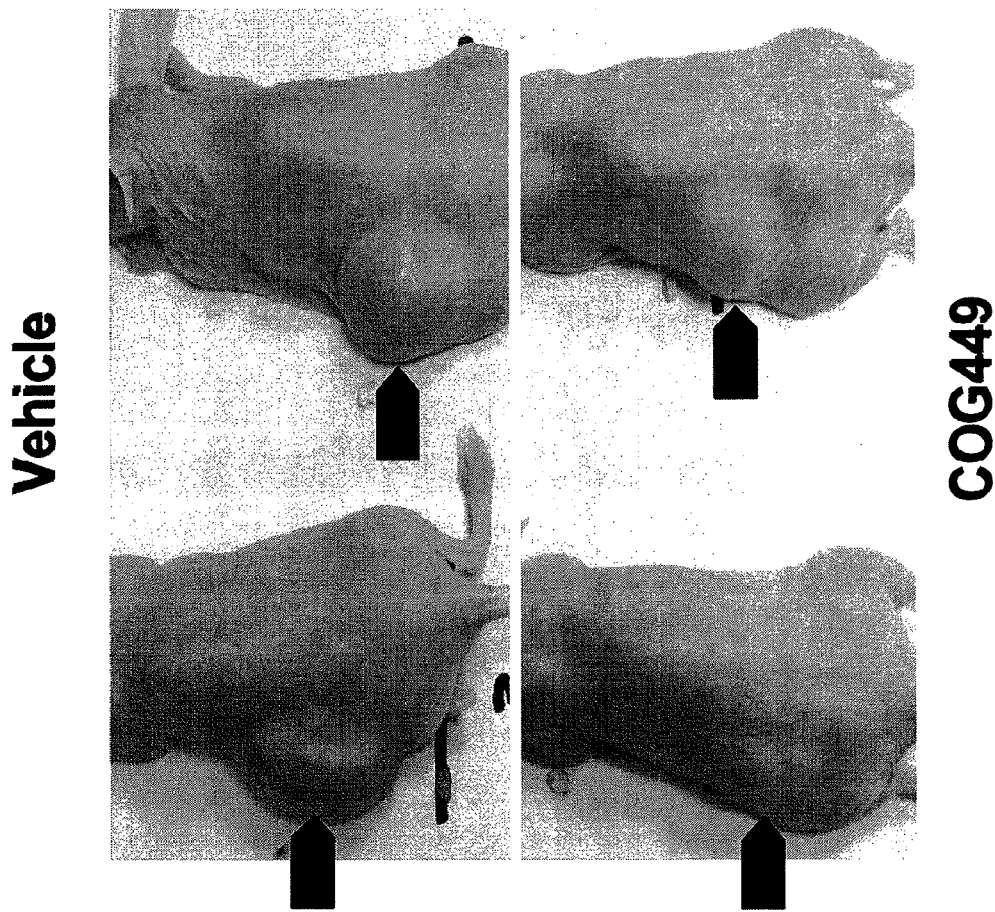
FIG. 23. Inhibition of the Ramos cell line of c-myc dependent Burkitt's lymphoma growth in vivo by treatment with COG449. Tumor growth in SCID mice treated with vehicle or COG449 peptide 19 days after injection with $10^7$ cells from the Ramos cell line of Burkitt's lymphoma.

Tumor measurements and treatment with COG449 (5 mg/kg, subcutaneous injection into the right shoulder area) or a vehicle control were performed by a technician who was blinded to the treatment solutions. At day 19, the tumor volume reached the predetermined size for termination of the experiment and animals were photographed (FIG. 23) and euthanized. Tumors were dissected, weighed, and segmented for pathological examination.

Figure 24A:
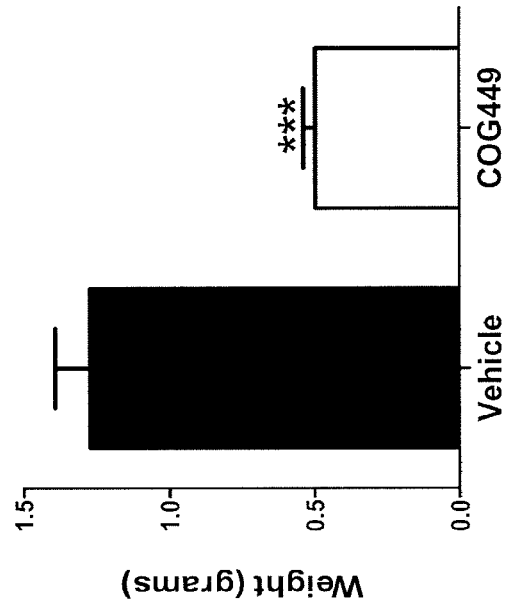
FIG. 24A: A plot of tumor volume of Ramos cell tumor xenografts in SCID mice with COG449 treatment (open squares) or lactated Ringer's solution control (filled squares) being initiated on day 11 once tumors reached a palpable size of 150-200 mm³.
Figure 24B:
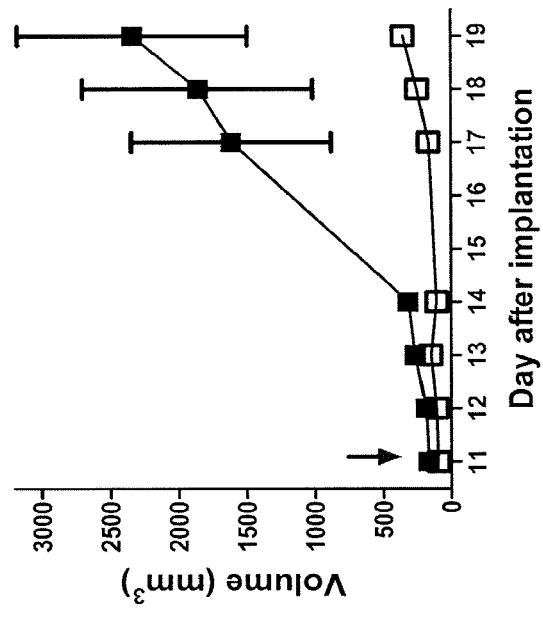
FIG. 24B: Final tumor mass for treated and untreated Ramos tumors harvested on day 19 after implantation. ***=p<0.001 by T-test.

The measured tumor volumes and final tumor weights are plotted in FIG. 24. Statistical analysis by one way ANOVA indicated that tumor growth was significantly inhibited by COG449 and final tumor mass was significantly lower in COG449 treated animals (p<0.001). Disaggregated cells from one portion of the tumors were analyzed by flow cytometry. This analysis showed that the tumor cells were indeed B-cells. Importantly, the significant reduction in tumor growth in the xenograft model demonstrates that COG449 possesses acceptable pharmacological properties for in vivo treatment of cancer.

Example 10. SET and CIP2A are Overexpressed in Triple-Negative Breast Cancer Breast cancer, the most common cancer affecting women, is a heterogeneous disease comprised of several molecular subtypes (Tang et al. (2009) Diagn Mol Pathol, Vol. 18(3): 125-132). Three main subgroups have been defined based on the pattern of expression of the hormone receptors estrogen (ER) and/or progesterone (PR), and the HER2 receptor status: luminal tumors (ER+/HER2−), HER2 amplified tumors (HER2+), and triple negative breast cancer (TNBC, ER−/PR−/HER2−). The identification of subgroups of breast cancer based on biologic differences has allowed the development of targeted therapeutic agents (Di Cosimo and Baselga (2010) Nat Rev Clin Oncol, Vol. 7(3): 139-147). For example, hormone therapies are effective in the treatment of hormone-receptor positive breast cancers while HER2-targeted therapies are useful in the treatment of HER2-positive tumors. TNBC, which lack expression of hormone receptors and HER2, is therefore insensitive to such targeted therapies. TNBC, and the molecularly related Basal-type breast cancer accounts for 15-20% of all invasive breast cancer cases and is characterized by its aggressive clinical behavior, high rates of relapse following chemotherapy, and poor patient survival (Di Cosimo and Baselga, 2010; Ray and Polite (2010) Cancer J, Vol. 16(1): 17-22). In addition, TNBC/Basal-like BC disproportionately afflicts African-American women with incidence as high as 39% (Carey et al. (2006) JAMA, Vol. 295(21): 2492-2502).

The most promising approach to treating women with this devastating disease is the use of molecularly targeted drugs that are specific for activated oncogenic pathways in the disease and thus generally present less toxicity. Thus, understanding the unique molecular changes associated with the development of TNBC is necessary in order to develop new targeted therapies that will be effective against this aggressive tumor type. However, little is actually known about the underlying genetic changes associated with the development of TNBC. Recent work has described aberrant activation of various receptor tyrosine kinase signaling pathways in TNBC, including the EGF, HGF, FAK, FGF, VEGF, and IGF-1 pathways, which can upregulate kinase cascades including Raf/MEK/ERK and PI3K/AKT (Di Cosimo and Baselga, 2010; Turner et al. (2009) Oncogene, Vol. 29(14): 2013-2023; Kurebayashi (2009) Breast Cancer, Vol. 16(4): 275-280). Additionally, defects in apoptotic pathways, including p53, Bcl2 and Mcl-1, are also common in TNBC.

Several naturally occurring inhibitors of PP2A have been identified, including SET (also known as I$_2$PP2A) and Cellular Inhibitor of PP2A (CIP2A). CIP2A has recently been described as an important PP2A inhibitor in multiple cancer types (Khanna et al. (2009) Cancer Inst, Vol. 101(11): 793-805). It is overexpressed in 39% of breast cancers and this is associated with clinical aggressiveness (Come et al. (2009) Clin Cancer Res, Vol. 15(16): 5092-5100). CIP2A overexpression cooperates with Ras and c-Myc for cell transformation, while its suppression inhibits tumor growth (Sablina et al. (2008) Cancer Metastasis Rev, Vol. 27(2): 137-146). CIP2A has been shown to interact with c-Myc and PP2A and display c-Myc stabilization activity (Junttila et al. (2007) Cell, Vol. 130(1): 51-62). CIP2A appears to selectively inhibit PP2A targeted to c-Myc (Westermarck and Hahn (2008) Trends Mol Med, Vol. 14(4): 152-160). The phosphoprotein SET is reported to have general PP2A inhibitory activity (Li et al. (1995) Biochemistry, Vol. 34(6): 1988-1996). SET was originally identified as a fusion protein in acute myelogenous leukemia and it is upregulated in multiple cancer types (Westermarck and Hahn, 2008).

Figure 25A:
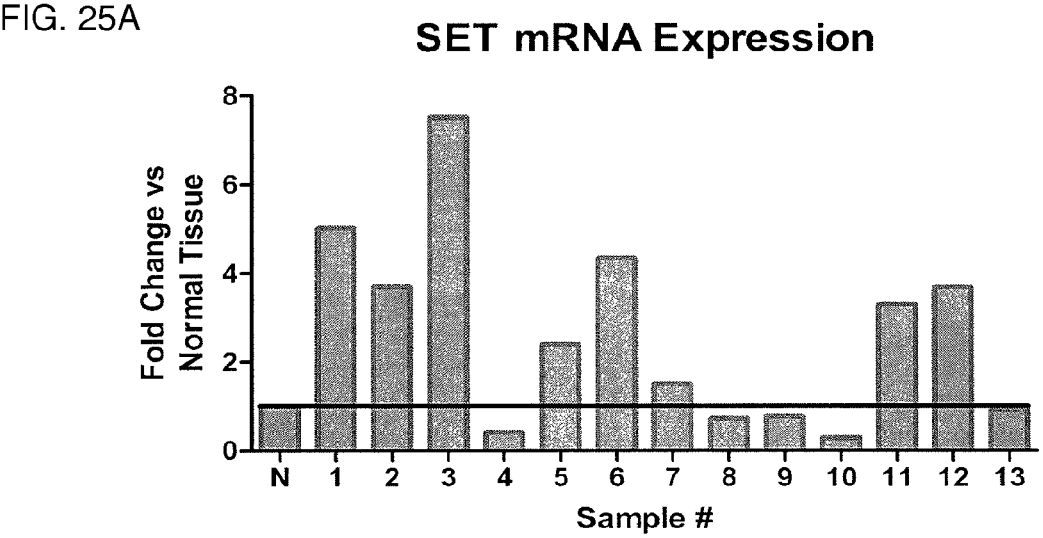
FIGS. 25A-25B. SET and CIP2A are overexpressed in human primary triple negative breast cancer (TNBC).
Figure 25B:
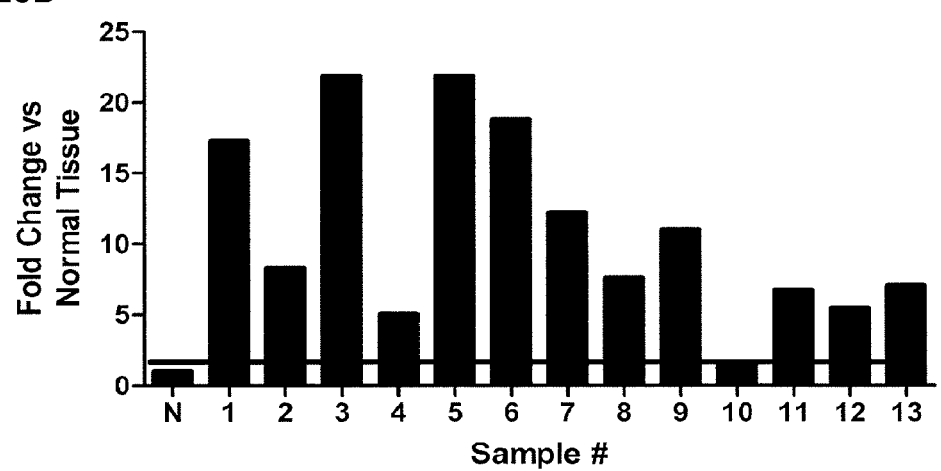
Figure 26:
FIG. 26. SET is overexpressed in human breast cancer cell lines. SET protein expression along with actin in TNBC cell lines by western blotting.

To determine whether these endogenous PP2A inhibitors are expressed in triple negative breast cancers as well, we evaluated SET and CIP2A expression by qRT-PCR in 13 cDNA samples from TNBC tumors and found overexpression in 7 of 13 for SET and 12 of 13 for CIP2A (FIGS. 25A and B). We also examined SET protein levels in human triple negative breast cancer cell lines relative to an actin control and found that SET is overexpressed in several breast cancer cell lines (FIG. 26).

ApoE mimetic peptides bind to SET and activate PP2A (see Example 5). We previously found that a peptide derived from amino acids 133-149 (known as COG133) inhibited inflammation and the production of cytokines and nitric oxide through reduced activation of the NF-κB pathway (Singh et al. (2008) J Biol Chem, Vol. 283(24):16752-16761). In order to study the underlying mechanism of this effect, COG133 was biotin labeled and used to affinity purify protein binding partners. Interestingly, the primary binding partner was the SET oncoprotein. The identification of SET, a potent PP2A inhibitor (Li et al. (1996) Journal of Biological Chemistry, Vol. 271(19): 11059-11062, as the binding partner of the apoE-mimetic peptide suggested that the peptides would bind SET and prevent it from binding to and inhibiting PP2A. COG449, a dimer derivative of COG133 (see Example 2) with improved potency and bioavailability, was also found to bind SET (data not shown).

Together, these studies emphasize a critical role for PP2A suppression in breast cancer and support an innovative approach for re-activating the PP2A tumor suppressor through therapies antagonizing its inhibitors.

Example 11. SET Antagonism with an ApoE Peptide Dimer Reduces Phosphorylation of a Cancer Related PP2A Target To determine if antagonism of SET with COG449, a BMOE-linked dimer of COG112 (see Example 2), reduced the phosphorylation of a known PP2A target that is implicated in breast cancer, we evaluated the status of eIF4E.

Figure 27:
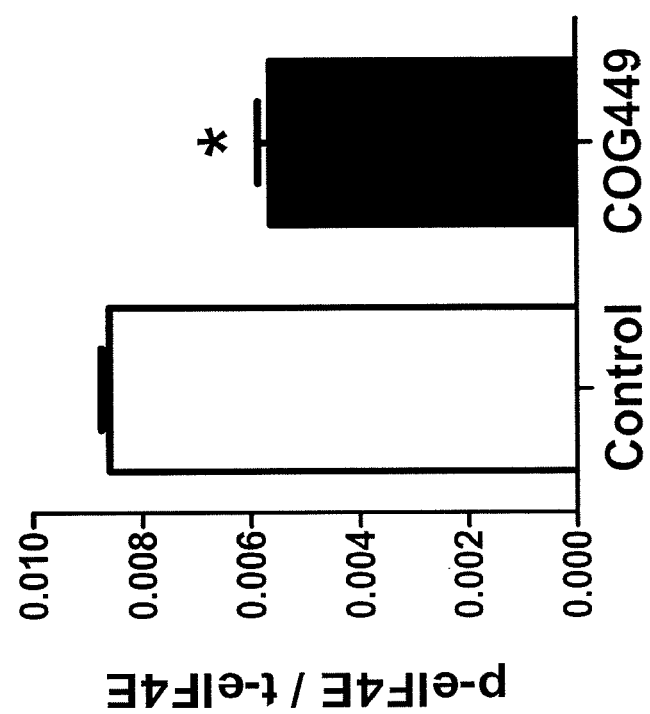
FIG. 27. COG449 reduces phosphorylation of eIF4E. U87MG glioblastoma cells were treated with COG449 (1 µM) or a vehicle control for 20 hrs and phosphorylation of eIF4E was determined by Western blotting with a phospho-specific antibody and a total eIF4E antibody. Treatment with COG449 reduced the ratio of the phospho- to total-eIF4E protein (n=3). * indicates p<0.01 compared to the vehicle control.

We previously demonstrated that antagonism of SET using related COG peptides reduced the phosphorylation of Akt (see Example 5), and the activity of NFκB (Singh et al., 2008). To analyze the effect of PP2A activation on the mTOR pathway, we analyzed the phosphorylation status of eIF4E and found that SET antagonism by COG449 treatment resulted in decreased phosphorylation of eIF4E (FIG. 27). Taken together, these data suggest that targeting a single protein, SET, with an ApoE peptide dimer results in down-regulation of signaling pathways that are implicated in proliferation and maintenance of an anti-apoptotic state that is required for tumorigenic growth of triple negative breast cancer.

Figure 28:
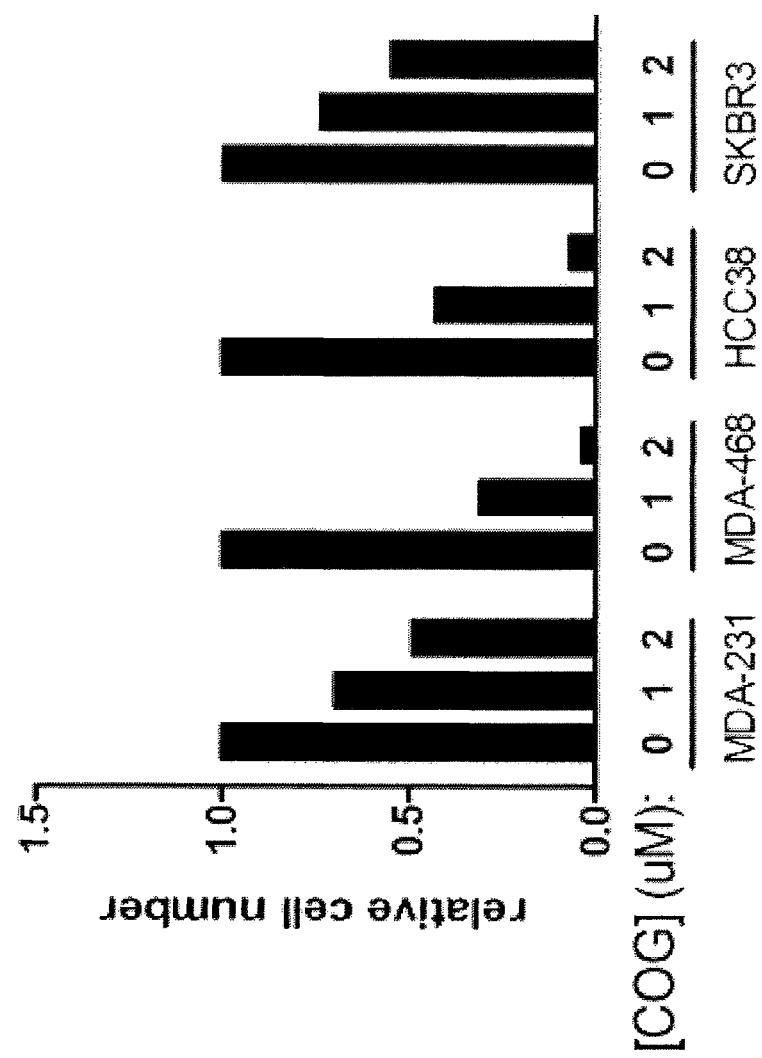
FIG. 28. Cytotoxic effects of COG449 in breast cancer cells. Cell lines were grown in serum-free media and COG449 as indicated for 24 hrs. Cellular proliferation was measured by cell counting. Cell number is represented relative to control, untreated cells.

Example 12. The ApoE Peptide Dimer COG449 Inhibits Growth of Breast Cancer Tumor Cells In Vitro and In Vivo Following demonstration of the activation of PP2A by the BMOE-linked COG112 peptide dimer, COG449 (see Example 2), and the inhibitory effects of COG449 on several PP2A targets, we explored whether this peptide had any anti-tumor activity. To determine whether COG449 might be effective in the treatment of human breast cancers, we treated several breast cancer cell lines with COG449 and found that COG449 was cytotoxic to all cell lines, including several triple negative breast cancer (TNBC) lines (MDA-231, MDA-468, and HCC38) (FIG. 28).

Figure 29:
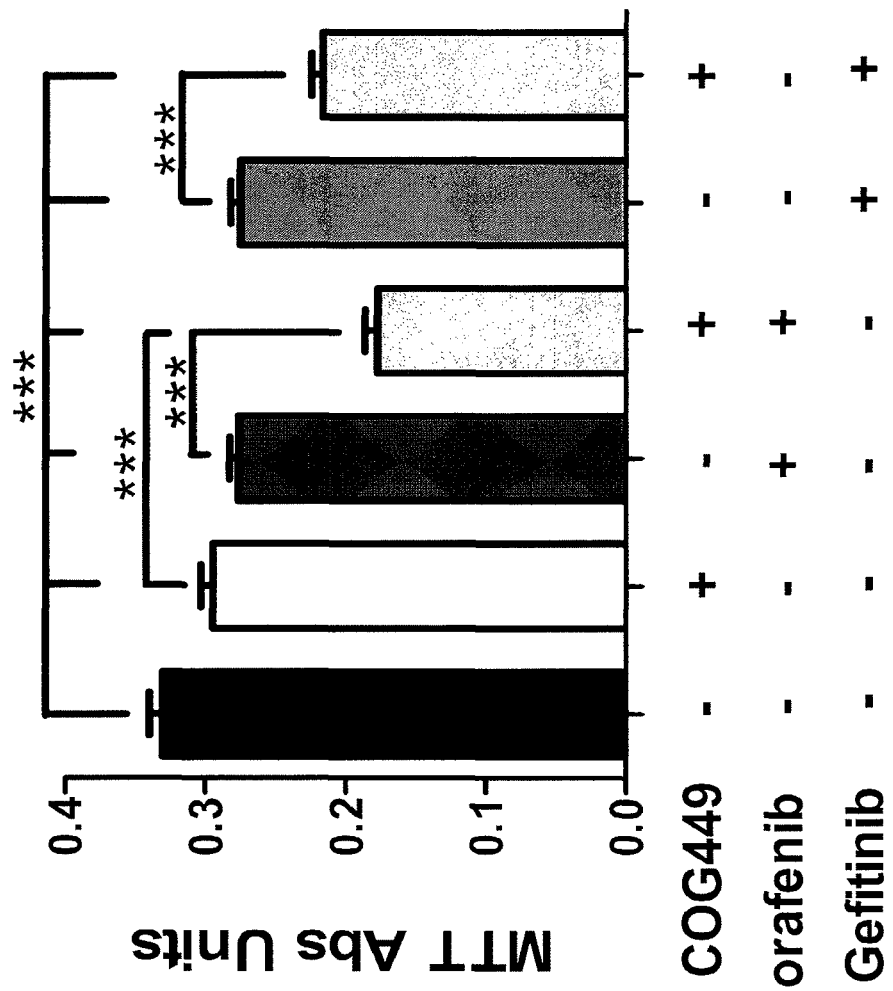
FIG. 29. Combination treatment with COG449 and sorafenib or gefitinb on triple negative breast cancer (TNBC) cell line growth. MDA-231 cells were grown in the presence of COG449, sorafenib, or gefitinb at sub-lethal doses as indicated. After 48 hrs, live cells were quantified using the MTT assay. *** indicates p<0.001.
Figure 30A:
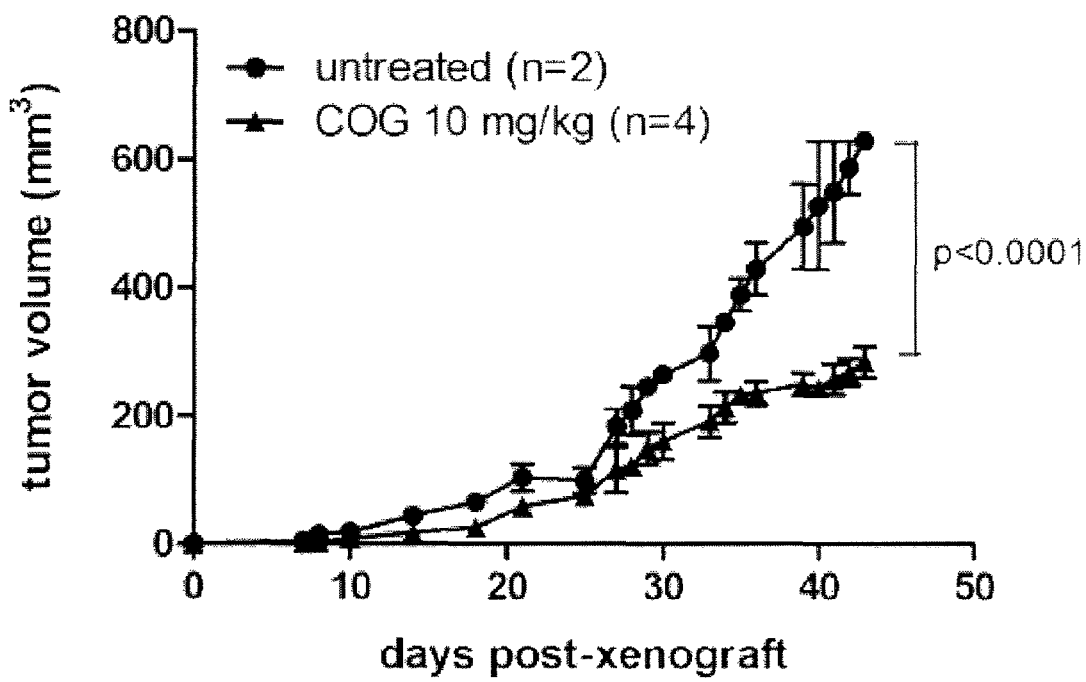
FIGS. 30A-30B. Inhibition of triple negative breast cancer (TNBC) tumor growth in xenografts with COG449 treatment.
Figure 30B:
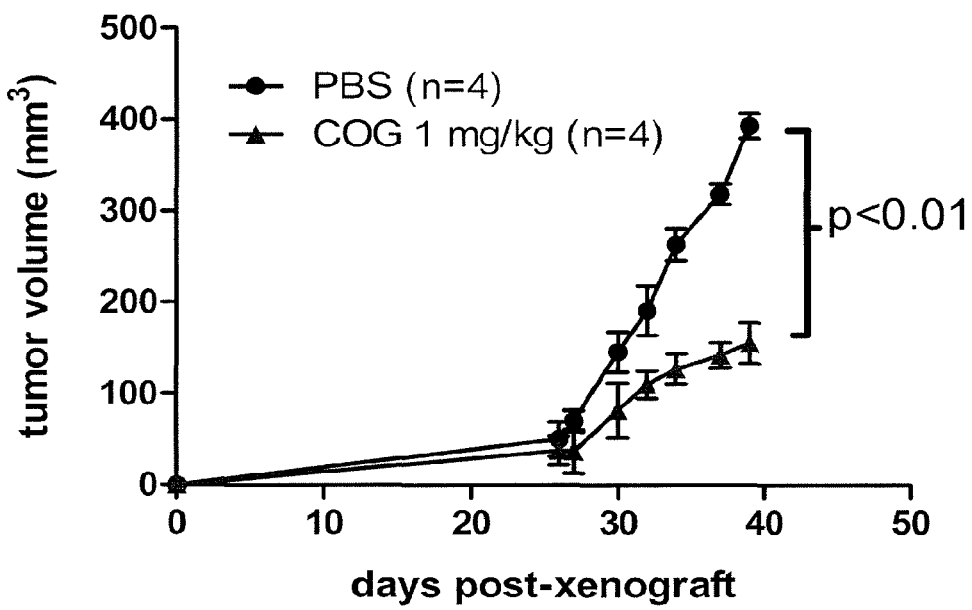

To begin assessment of the potential of combination therapies with COG449, we analyzed the effect of treating MDA-231 cells with sub-lethal doses of COG449 and the multi-kinase inhibitor Sorafenib or the EGFR inhibitor Gefitinib at concentrations below their ED50 doses. The combination of COG449 and Sorafenib or Gefitinib produced a robust cytotoxic effect that was greater than the effect of either compound alone (FIG. 29). We also evaluated the effects of COG449 in vivo using xenograft experiments. To determine whether COG449 might be effective against TNBC tumors in xenografts, immune compromised NOD/SCID gamma-chain null (NSG) mice were injected with MDA-231 cells into their 4th mammary glands. Once tumors became palpable at around 10 days, tumors were treated by twice weekly subcutaneous injection of COG449 at 10 mg/kg. At 28 days post-xenograft, daily intra-tumor injection of COG449 was initiated and continued until sacrifice (FIG. 30A). In order to use a more clinically relevant treatment paradigm, MDA-231 xenografted mice were treated 3-times a week with 1 mg/kg COG449 by intravenous injection (FIG. 30B). No cytotoxic effects were observed in mice in either of these studies. The effective inhibition of tumor growth in these xenograft models indicate that COG449 has suitable pharmacological properties for the treatment of cancer. Furthermore, we have administered COG449 by intravenous infusion at doses of 10-15 mg/kg without any observed adverse effects. When COG449 doses were increased to 20 mg/kg we observed mild edema in the front paws and lethargy as the first adverse events associated with the administration of COG449. Together, these data suggest that a wide safety window exists between tumor suppressive doses and doses that elicit toxic effects.

It is understood that the disclosed invention is not limited to the particular methodology, protocols and reagents described as these may vary. It is also understood that the terminology used herein is for the purposes of describing particular embodiments only and is not intended to limit the scope of the present invention which will be limited only by the appended claims.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the exemplary methods, devices, and materials are as described. All patents, patent applications and other publications cited herein and the materials for which they are cited are specifically incorporated by reference in their entireties.

Those skilled in the art will recognize, or be able to ascertain using no more than routine experimentation, many equivalents to the specific embodiments of the invention described herein. Such equivalents are intended to be encompassed by the following claims.

The invention claimed is:

1. A peptide dimer comprising a first ApoE peptide and a second ApoE peptide, wherein each of said first and second ApoE peptides is no more than 20 amino acids in length and comprises a sequence selected from the group consisting of CLRVRLASHLRKLRKRLL (SEQ ID NO: 15), CAS(Aib)LRKL(Aib)KRLL (SEQ ID NO: 16), CLRVRLAS(Aib)LKRLRK(Nitro-Arg)LL (SEQ ID NO: 17), and CLRVRLAS(Aib)LRKLR(K-Ac)RLL (SEQ ID NO: 18), wherein the first and second ApoE peptides are covalently cross-linked through the cysteine residue at each amino terminus via a bismaleimide linker.

2. The peptide dimer of claim 1, wherein said bismaleimide is bismaleimido-ethane or bismaleimido-hexane.

3. The peptide dimer of claim 1, wherein said first and second ApoE peptides are the same.

4. The peptide dimer of claim 1, wherein said first and second ApoE peptides are different.

5. The peptide dimer of claim 1, wherein said first ApoE peptide is conjugated to a first protein transduction domain through one or more first linking residues.

6. The peptide dimer of claim 5, wherein said first protein transduction domain is selected from the group consisting of peptides derived from antennapedia, TAT, SynB1, SynB3, SynB5, and polyarginine.

7. The peptide dimer of claim 6, wherein said first protein transduction domain has a sequence of RQIKIWFQNRRMKWKK (SEQ ID NO: 8), YGRKKRRQRRR (SEQ ID NO: 9), or WKK.

8. The peptide dimer of claim 5, wherein said one or more first linking residues is cysteine, azidohomoalanine, or propargylglycine.

9. The peptide dimer of claim 5, wherein said second ApoE peptide is conjugated to a second protein transduction domain through one or more second linking residues.

10. The peptide dimer of claim 9, wherein said second protein transduction domain is selected from the group consisting of peptides derived from antennapedia, TAT, SynB1, SynB3, SynB5, and polyarginine.

11. The peptide dimer of claim 10, wherein said second protein transduction domain has a sequence of RQIKIWFQNRRNIKWKK (SEQ ID NO: 8), YGRKKRRQRRR (SEQ ID NO: 9), or WKK.

12. The peptide dimer of claim 9, wherein said one or more second linking residues is cysteine, azidohomoalanine, or propargylglycine.

13. A pharmaceutical composition comprising an effective amount of a peptide dimer of claim 1 and a pharmaceutically acceptable carrier.

14. The peptide dimer of claim 1, wherein said first ApoE peptide is conjugated to a first protein transduction domain through a first cysteine residue, said second ApoE peptide is conjugated to a second protein transduction domain through a second cysteine residue, wherein each of said first and second protein transduction domains has a sequence of RQIKIWFQNRRMKWKK (SEQ ID NO: 8) and is conjugated to the amino terminal end of each first and second ApoE peptides, and wherein each said first and second ApoE peptides has a sequence of CLRVRLASHLRKLRKRLL (SEQ ID NO: 15).

* * * * *

SEQUENCE LISTING

```
<160> NUMBER OF SEQ ID NOS: 90

<210> SEQ ID NO 1
<211> LENGTH: 34
<212> TYPE: PRT
<213> ORGANISM: Artificial Sequence
<220> FEATURE:
<223> OTHER INFORMATION: ApoE mimetic peptide

<400> SEQUENCE: 1

Arg Gln Ile Lys Ile Trp Phe Gln Asn Arg Arg Met Lys Trp Lys Lys
1               5                   10                  15

Cys Leu Arg Val Arg Leu Ala Ser His Leu Arg Lys Leu Arg Lys Arg
            20                  25                  30

Leu Leu
```

```
<210> SEQ ID NO 2
<211> LENGTH: 17
<212> TYPE: PRT
<213> ORGANISM: Artificial Sequence
<220> FEATURE:
<223> OTHER INFORMATION: ApoE mimetic peptide

<400> SEQUENCE: 2

Leu Leu Arg Lys Arg Leu Lys Arg Leu His Ser Ala Leu Arg Val Arg
1               5                   10                  15

Leu

<210> SEQ ID NO 3
<211> LENGTH: 17
<212> TYPE: PRT
<213> ORGANISM: Artificial Sequence
<220> FEATURE:
<223> OTHER INFORMATION: ApoE mimetic peptide

<400> SEQUENCE: 3

Leu Arg Val Arg Leu Ala Ser His Leu Arg Lys Leu Arg Lys Arg Leu
1               5                   10                  15

Leu

<210> SEQ ID NO 4
<211> LENGTH: 17
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (15)..(15)
<223> OTHER INFORMATION: Xaa may be nitroarginine

<400> SEQUENCE: 4

Leu Arg Val Arg Leu Ala Ser Xaa Leu Lys Arg Leu Arg Lys Xaa Leu
1               5                   10                  15

Leu

<210> SEQ ID NO 5
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib

<400> SEQUENCE: 5

Ala Ser Xaa Leu Arg Lys Leu Xaa Lys Arg Leu Leu
1               5                   10

<210> SEQ ID NO 6
<211> LENGTH: 24
<212> TYPE: PRT
<213> ORGANISM: Artificial Sequence
```

```
<220> FEATURE:
<223> OTHER INFORMATION: ApoE mimetic peptide
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 6

Tyr Gly Arg Lys Lys Arg Arg Gln Arg Arg Cys Ala Ser Xaa Leu
1               5                   10                  15

Arg Lys Leu Xaa Lys Arg Leu Leu
            20

<210> SEQ ID NO 7
<211> LENGTH: 29
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Aib

<400> SEQUENCE: 7

Arg Gln Ile Lys Ile Trp Phe Gln Asn Arg Arg Met Lys Trp Lys Lys
1               5                   10                  15

Cys Ala Ser Xaa Leu Arg Lys Leu Xaa Lys Arg Leu Leu
            20                  25

<210> SEQ ID NO 8
<211> LENGTH: 16
<212> TYPE: PRT
<213> ORGANISM: Artificial Sequence
<220> FEATURE:
<223> OTHER INFORMATION: antennapedia protein transduction domain

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: HIV TAT protein transduction domain

<400> SEQUENCE: 9

Tyr Gly Arg Lys Lys Arg Arg Gln Arg Arg Arg
1               5                   10

<210> SEQ ID NO 10
<211> LENGTH: 34
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (25)..(25)
```

<223> OTHER INFORMATION: Aib
<220> FEATURE:
<221> NAME/KEY: MISC_FEATURE
<222> LOCATION: (32)..(32)
<223> OTHER INFORMATION: Xaa may be nitroarginine

<400> SEQUENCE: 10

Arg Gln Ile Lys Ile Trp Phe Gln Asn Arg Arg Met Lys Trp Lys Lys
1               5                   10                  15

Cys Leu Arg Val Arg Leu Ala Ser Xaa Leu Lys Arg Leu Arg Lys Xaa
            20                  25                  30

Leu Leu

<210> SEQ ID NO 11
<211> LENGTH: 34
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (25)..(25)
<223> OTHER INFORMATION: Aib
<220> FEATURE:
<221> NAME/KEY: MISC_FEATURE
<222> LOCATION: (31)..(31)
<223> OTHER INFORMATION: Xaa may be acetyl lysine

<400> SEQUENCE: 11

Arg Gln Ile Lys Ile Trp Phe Gln Asn Arg Arg Met Lys Trp Lys Lys
1               5                   10                  15

Cys Leu Arg Val Arg Leu Ala Ser Xaa Leu Arg Lys Leu Arg Xaa Arg
            20                  25                  30

Leu Leu

<210> SEQ ID NO 12
<211> LENGTH: 29
<212> TYPE: PRT
<213> ORGANISM: Artificial Sequence
<220> FEATURE:
<223> OTHER INFORMATION: ApoE mimetic peptide

<400> SEQUENCE: 12

Tyr Gly Arg Lys Lys Arg Arg Gln Arg Arg Cys Leu Arg Val Arg
1               5                   10                  15

Leu Ala Ser His Leu Arg Lys Leu Arg Lys Arg Leu Leu
            20                  25

<210> SEQ ID NO 13
<211> LENGTH: 29
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (20)..(20)
<223> OTHER INFORMATION: Aib
<220> FEATURE:
<221> NAME/KEY: MISC_FEATURE
<222> LOCATION: (27)..(27)
<223> OTHER INFORMATION: Xaa may be nitroarginine

<400> SEQUENCE: 13

Tyr Gly Arg Lys Lys Arg Arg Gln Arg Arg Cys Leu Arg Val Arg
1               5                   10                  15

Leu Ala Ser Xaa Leu Lys Arg Leu Arg Lys Xaa Leu Leu
            20                  25

<210> SEQ ID NO 14
<211> LENGTH: 29
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (20)..(20)
<223> OTHER INFORMATION: Aib
<220> FEATURE:
<221> NAME/KEY: MISC_FEATURE
<222> LOCATION: (26)..(26)
<223> OTHER INFORMATION: Xaa may be acetyl lysine

<400> SEQUENCE: 14

Tyr Gly Arg Lys Lys Arg Arg Gln Arg Arg Arg Cys Leu Arg Val Arg
1               5                   10                  15
Leu Ala Ser Xaa Leu Arg Lys Leu Arg Xaa Arg Leu Leu
            20                  25

<210> SEQ ID NO 15
<211> LENGTH: 18
<212> TYPE: PRT
<213> ORGANISM: Artificial Sequence
<220> FEATURE:
<223> OTHER INFORMATION: ApoE mimetic peptide

<400> SEQUENCE: 15

Cys Leu Arg Val Arg Leu Ala Ser His Leu Arg Lys Leu Arg Lys Arg
1               5                   10                  15
Leu Leu

<210> SEQ ID NO 16
<211> LENGTH: 13
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (9)..(9)
<223> OTHER INFORMATION: Aib

<400> SEQUENCE: 16

Cys Ala Ser Xaa Leu Arg Lys Leu Xaa Lys Arg Leu Leu
1               5                   10

<210> SEQ ID NO 17
<211> LENGTH: 18
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (9)..(9)
<223> OTHER INFORMATION: Aib
<220> FEATURE:
<221> NAME/KEY: MISC_FEATURE
<222> LOCATION: (16)..(16)
<223> OTHER INFORMATION: Xaa may be nitroarginine

```
<400> SEQUENCE: 17

Cys Leu Arg Val Arg Leu Ala Ser Xaa Leu Lys Arg Leu Arg Lys Xaa
1               5                   10                  15

Leu Leu

<210> SEQ ID NO 18
<211> LENGTH: 18
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (9)..(9)
<223> OTHER INFORMATION: Aib
<220> FEATURE:
<221> NAME/KEY: MISC_FEATURE
<222> LOCATION: (15)..(15)
<223> OTHER INFORMATION: Xaa may be acetyl lysine

<400> SEQUENCE: 18

Cys Leu Arg Val Arg Leu Ala Ser Xaa Leu Arg Lys Leu Arg Xaa Arg
1               5                   10                  15

Leu Leu

<210> SEQ ID NO 19
<211> LENGTH: 34
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (17)..(17)
<223> OTHER INFORMATION: Xaa may be azidohomoalanine

<400> SEQUENCE: 19

Arg Gln Ile Lys Ile Trp Phe Gln Asn Arg Arg Met Lys Trp Lys Lys
1               5                   10                  15

Xaa Leu Arg Val Arg Leu Ala Ser His Leu Arg Lys Leu Arg Lys Arg
                20                  25                  30

Leu Leu

<210> SEQ ID NO 20
<211> LENGTH: 29
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (17)..(17)
<223> OTHER INFORMATION: Xaa may be azidohomoalanine
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Aib

<400> SEQUENCE: 20

Arg Gln Ile Lys Ile Trp Phe Gln Asn Arg Arg Met Lys Trp Lys Lys
1               5                   10                  15

Xaa Ala Ser Xaa Leu Arg Lys Leu Xaa Lys Arg Leu Leu
                20                  25
```

```
<210> SEQ ID NO 21
<211> LENGTH: 34
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (17)..(17)
<223> OTHER INFORMATION: Xaa may be azidohomoalanine
<220> FEATURE:
<221> NAME/KEY: MOD_RES
<222> LOCATION: (25)..(25)
<223> OTHER INFORMATION: Aib
<220> FEATURE:
<221> NAME/KEY: MISC_FEATURE
<222> LOCATION: (32)..(32)
<223> OTHER INFORMATION: Xaa may be nitroarginine

<400> SEQUENCE: 21

Arg Gln Ile Lys Ile Trp Phe Gln Asn Arg Arg Met Lys Trp Lys Lys
1               5                   10                  15

Xaa Leu Arg Val Arg Leu Ala Ser Xaa Leu Lys Arg Leu Arg Lys Xaa
            20                  25                  30

Leu Leu

<210> SEQ ID NO 22
<211> LENGTH: 34
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (17)..(17)
<223> OTHER INFORMATION: Xaa may be azidohomoalanine
<220> FEATURE:
<221> NAME/KEY: MOD_RES
<222> LOCATION: (25)..(25)
<223> OTHER INFORMATION: Aib
<220> FEATURE:
<221> NAME/KEY: MISC_FEATURE
<222> LOCATION: (31)..(31)
<223> OTHER INFORMATION: Xaa may be acetyl lysine

<400> SEQUENCE: 22

Arg Gln Ile Lys Ile Trp Phe Gln Asn Arg Arg Met Lys Trp Lys Lys
1               5                   10                  15

Xaa Leu Arg Val Arg Leu Ala Ser Xaa Leu Arg Lys Leu Arg Xaa Arg
            20                  25                  30

Leu Leu

<210> SEQ ID NO 23
<211> LENGTH: 29
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (12)..(12)
<223> OTHER INFORMATION: Xaa may be azidohomoalanine

<400> SEQUENCE: 23

Tyr Gly Arg Lys Lys Arg Arg Gln Arg Arg Xaa Leu Arg Val Arg
1               5                   10                  15

Leu Ala Ser His Leu Arg Lys Leu Arg Lys Arg Leu Leu
```

<210> SEQ ID NO 24
<211> LENGTH: 24
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (12)..(12)
<223> OTHER INFORMATION: Xaa may be azidohomoalanine
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 24

Tyr Gly Arg Lys Lys Arg Arg Gln Arg Arg Xaa Ala Ser Xaa Leu
1               5                   10                  15

Arg Lys Leu Xaa Lys Arg Leu Leu
            20

<210> SEQ ID NO 25
<211> LENGTH: 29
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (12)..(12)
<223> OTHER INFORMATION: Xaa may be azidohomoalanine
<220> FEATURE:
<221> NAME/KEY: MOD_RES
<222> LOCATION: (20)..(20)
<223> OTHER INFORMATION: Aib
<220> FEATURE:
<221> NAME/KEY: MISC_FEATURE
<222> LOCATION: (27)..(27)
<223> OTHER INFORMATION: Xaa may be nitroarginine

<400> SEQUENCE: 25

Tyr Gly Arg Lys Lys Arg Arg Gln Arg Arg Xaa Leu Arg Val Arg
1               5                   10                  15

Leu Ala Ser Xaa Leu Lys Arg Leu Arg Lys Xaa Leu Leu
            20                  25

<210> SEQ ID NO 26
<211> LENGTH: 29
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (12)..(12)
<223> OTHER INFORMATION: Xaa may be azidohomoalanine
<220> FEATURE:
<221> NAME/KEY: MOD_RES
<222> LOCATION: (20)..(20)
<223> OTHER INFORMATION: Aib
<220> FEATURE:
<221> NAME/KEY: MISC_FEATURE
<222> LOCATION: (26)..(26)
<223> OTHER INFORMATION: Xaa may be acetyl lysine

<400> SEQUENCE: 26

Tyr Gly Arg Lys Lys Arg Arg Gln Arg Arg Xaa Leu Arg Val Arg
1               5                   10                  15

Leu Ala Ser Xaa Leu Arg Lys Leu Arg Xaa Arg Leu Leu
            20                  25

<210> SEQ ID NO 27
<211> LENGTH: 18
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (1)..(1)
<223> OTHER INFORMATION: Xaa may be propargylglycine

<400> SEQUENCE: 27

Xaa Leu Arg Val Arg Leu Ala Ser His Leu Arg Lys Leu Arg Lys Arg
1               5                   10                  15

Leu Leu

<210> SEQ ID NO 28
<211> LENGTH: 13
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (1)..(1)
<223> OTHER INFORMATION: Xaa may be propargylglycine
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (9)..(9)
<223> OTHER INFORMATION: Aib

<400> SEQUENCE: 28

Xaa Ala Ser Xaa Leu Arg Lys Leu Xaa Lys Arg Leu Leu
1               5                   10

<210> SEQ ID NO 29
<211> LENGTH: 18
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (1)..(1)
<223> OTHER INFORMATION: Xaa may be propargylglycine
<220> FEATURE:
<221> NAME/KEY: MOD_RES
<222> LOCATION: (9)..(9)
<223> OTHER INFORMATION: Aib
<220> FEATURE:
<221> NAME/KEY: MISC_FEATURE
<222> LOCATION: (16)..(16)
<223> OTHER INFORMATION: Xaa may be nitroarginine

<400> SEQUENCE: 29

Xaa Leu Arg Val Arg Leu Ala Ser Xaa Leu Lys Arg Leu Arg Lys Xaa
1               5                   10                  15

Leu Leu

```
<210> SEQ ID NO 30
<211> LENGTH: 18
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (1)..(1)
<223> OTHER INFORMATION: Xaa may be propargylglycine
<220> FEATURE:
<221> NAME/KEY: MOD_RES
<222> LOCATION: (9)..(9)
<223> OTHER INFORMATION: Aib
<220> FEATURE:
<221> NAME/KEY: MISC_FEATURE
<222> LOCATION: (15)..(15)
<223> OTHER INFORMATION: Xaa may be acetyl lysine

<400> SEQUENCE: 30

Xaa Leu Arg Val Arg Leu Ala Ser Xaa Leu Arg Lys Leu Arg Xaa Arg
1               5                   10                  15

Leu Leu

<210> SEQ ID NO 31
<211> LENGTH: 18
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (1)..(1)
<223> OTHER INFORMATION: Xaa may be azidohomoalanine

<400> SEQUENCE: 31

Xaa Leu Arg Val Arg Leu Ala Ser His Leu Arg Lys Leu Arg Lys Arg
1               5                   10                  15

Leu Leu

<210> SEQ ID NO 32
<211> LENGTH: 13
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (1)..(1)
<223> OTHER INFORMATION: Xaa may be azidohomoalanine
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (9)..(9)
<223> OTHER INFORMATION: Aib

<400> SEQUENCE: 32

Xaa Ala Ser Xaa Leu Arg Lys Leu Xaa Lys Arg Leu Leu
1               5                   10

<210> SEQ ID NO 33
<211> LENGTH: 18
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
```

```
<222> LOCATION: (1)..(1)
<223> OTHER INFORMATION: Xaa may be azidohomoalanine
<220> FEATURE:
<221> NAME/KEY: MOD_RES
<222> LOCATION: (9)..(9)
<223> OTHER INFORMATION: Aib
<220> FEATURE:
<221> NAME/KEY: MISC_FEATURE
<222> LOCATION: (16)..(16)
<223> OTHER INFORMATION: Xaa may be nitroarginine

<400> SEQUENCE: 33

Xaa Leu Arg Val Arg Leu Ala Ser Xaa Leu Lys Arg Leu Arg Lys Xaa
1               5                   10                  15

Leu Leu

<210> SEQ ID NO 34
<211> LENGTH: 18
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MISC_FEATURE
<222> LOCATION: (1)..(1)
<223> OTHER INFORMATION: Xaa may be azidohomoalanine
<220> FEATURE:
<221> NAME/KEY: MOD_RES
<222> LOCATION: (9)..(9)
<223> OTHER INFORMATION: Aib
<220> FEATURE:
<221> NAME/KEY: MISC_FEATURE
<222> LOCATION: (15)..(15)
<223> OTHER INFORMATION: Xaa may be acetyl lysine

<400> SEQUENCE: 34

Xaa Leu Arg Val Arg Leu Ala Ser Xaa Leu Arg Lys Leu Arg Xaa Arg
1               5                   10                  15

Leu Leu

<210> SEQ ID NO 35
<211> LENGTH: 17
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (14)..(14)
<223> OTHER INFORMATION: Xaa may be acetyl lysine

<400> SEQUENCE: 35

Leu Arg Val Arg Leu Ala Ser Xaa Leu Arg Lys Leu Arg Xaa Arg Leu
1               5                   10                  15

Leu

<210> SEQ ID NO 36
<211> LENGTH: 13
<212> TYPE: PRT
<213> ORGANISM: Artificial Sequence
<220> FEATURE:
<223> OTHER INFORMATION: protein transduction domain peptide

<400> SEQUENCE: 36

Gly Arg Lys Lys Arg Arg Gln Arg Arg Arg Pro Pro Gln
```

```
1               5                    10
```

<210> SEQ ID NO 37
<211> LENGTH: 7
<212> TYPE: PRT
<213> ORGANISM: Artificial Sequence
<220> FEATURE:
<223> OTHER INFORMATION: protein transduction domain peptide

<400> SEQUENCE: 37

```
Arg Arg Met Lys Trp Lys Lys
1               5
```

<210> SEQ ID NO 38
<211> LENGTH: 18
<212> TYPE: PRT
<213> ORGANISM: Artificial Sequence
<220> FEATURE:
<223> OTHER INFORMATION: protein transduction domain peptide

<400> SEQUENCE: 38

```
Arg Gly Gly Arg Leu Ser Tyr Ser Arg Arg Arg Phe Ser Thr Ser Thr
1               5                   10                  15

Gly Arg
```

<210> SEQ ID NO 39
<211> LENGTH: 10
<212> TYPE: PRT
<213> ORGANISM: Artificial Sequence
<220> FEATURE:
<223> OTHER INFORMATION: protein transduction domain peptide

<400> SEQUENCE: 39

```
Arg Arg Leu Ser Tyr Ser Arg Arg Arg Phe
1               5                   10
```

<210> SEQ ID NO 40
<211> LENGTH: 17
<212> TYPE: PRT
<213> ORGANISM: Artificial Sequence
<220> FEATURE:
<223> OTHER INFORMATION: protein transduction domain peptide

<400> SEQUENCE: 40

```
Arg Gly Gly Arg Leu Ala Tyr Leu Arg Arg Arg Trp Ala Val Leu Gly
1               5                   10                  15

Arg
```

<210> SEQ ID NO 41
<211> LENGTH: 8
<212> TYPE: PRT
<213> ORGANISM: Artificial Sequence
<220> FEATURE:
<223> OTHER INFORMATION: protein transduction domain peptide

<400> SEQUENCE: 41

```
Arg Arg Arg Arg Arg Arg Arg Arg
1               5
```

<210> SEQ ID NO 42
<211> LENGTH: 17
<212> TYPE: PRT
<213> ORGANISM: Artificial Sequence
<220> FEATURE:
<223> OTHER INFORMATION: ApoE mimetic peptide
<220> FEATURE:

```
<221> NAME/KEY: MISC_FEATURE
<222> LOCATION: (9)..(9)
<223> OTHER INFORMATION: Xaa may be N-methylated leucine
<220> FEATURE:
<221> NAME/KEY: MOD_RES
<222> LOCATION: (17)..(17)
<223> OTHER INFORMATION: AMIDATION

<400> SEQUENCE: 42

Leu Arg Val Arg Leu Ala Ser His Xaa Arg Lys Leu Arg Lys Arg Leu
1               5                   10                  15

Leu

<210> SEQ ID NO 43
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 43

Ala Ser His Xaa Arg Lys Leu Arg Lys Arg Leu Leu
1               5                   10

<210> SEQ ID NO 44
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 44

Ala Ser Xaa Leu Arg Lys Leu Arg Lys Arg Leu Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
```

<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 45

Asp Ser Xaa Leu Arg Lys Leu Arg Lys Arg Leu Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 46

Ala Ser His Leu Arg Lys Leu Xaa Lys Arg Leu Leu
1               5                   10

<210> SEQ ID NO 47
<211> LENGTH: 15
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (14)..(14)
<223> OTHER INFORMATION: Aib
<220> FEATURE:
<221> NAME/KEY: MOD_RES
<222> LOCATION: (15)..(15)
<223> OTHER INFORMATION: AMIDATION

<400> SEQUENCE: 47

Asp Arg Xaa Ala Ser His Leu Arg Lys Leu Arg Lys Arg Xaa Leu
1               5                   10                  15

<210> SEQ ID NO 48
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)

```
<223> OTHER INFORMATION: Aib
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 48

Asp Ser Xaa Leu Arg Lys Leu Arg Lys Arg Xaa Leu
1               5                   10

<210> SEQ ID NO 49
<211> LENGTH: 15
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (15)..(15)
<223> OTHER INFORMATION: AMIDATION

<400> SEQUENCE: 49

Asp Arg Xaa Ala Ser His Leu Arg Lys Leu Xaa Lys Arg Leu Leu
1               5                   10                  15

<210> SEQ ID NO 50
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 50

Asp Ser Xaa Leu Arg Lys Leu Xaa Lys Arg Leu Leu
1               5                   10

<210> SEQ ID NO 51
<211> LENGTH: 15
<212> TYPE: PRT
<213> ORGANISM: Artificial Sequence
<220> FEATURE:
```

```
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (15)..(15)
<223> OTHER INFORMATION: AMIDATION

<400> SEQUENCE: 51

Asp Arg Xaa Ala Ser Xaa Leu Arg Lys Leu Arg Lys Arg Leu Leu
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (15)..(15)
<223> OTHER INFORMATION: AMIDATION

<400> SEQUENCE: 52

Asp Arg Xaa Ala Ser His Leu Arg Lys Leu Arg Lys Arg Leu Leu
1               5                   10                  15

<210> SEQ ID NO 53
<211> LENGTH: 13
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (9)..(9)
<223> OTHER INFORMATION: Aib
<220> FEATURE:
<221> NAME/KEY: MOD_RES
<222> LOCATION: (13)..(13)
<223> OTHER INFORMATION: AMIDATION

<400> SEQUENCE: 53

Cys Ala Ser Xaa Leu Arg Lys Leu Xaa Lys Arg Leu Leu
1               5                   10

<210> SEQ ID NO 54
```

```
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 54

Asp Ser Xaa Leu Arg Lys Leu Xaa Lys Arg Leu Leu
1               5                   10

<210> SEQ ID NO 55
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 55

Ala Ser Xaa Leu Arg Lys Leu Xaa Lys Arg Leu Val
1               5                   10

<210> SEQ ID NO 56
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION
```

-continued

```
<400> SEQUENCE: 56

Ala Ser Xaa Leu Arg Lys Leu Xaa Lys Arg Leu Met
1               5                   10

<210> SEQ ID NO 57
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 57

Ala Ser Xaa Leu Arg Lys Leu Xaa Lys Arg Leu Ile
1               5                   10

<210> SEQ ID NO 58
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 58

Ala Ser Xaa Leu Arg Lys Leu Xaa Lys Arg Leu Ala
1               5                   10

<210> SEQ ID NO 59
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
```

```
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 59

Ala Ser Xaa Leu Arg Lys Leu Xaa Lys Ala Leu Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (10)..(10)
<223> OTHER INFORMATION: Orn
<220> FEATURE:
<221> NAME/KEY: MOD_RES
<222> LOCATION: (12)..(12)
<223> OTHER INFORMATION: AMIDATION

<400> SEQUENCE: 60

Ala Ser Xaa Leu Arg Lys Leu Xaa Lys Xaa Leu Leu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (10)..(10)
<223> OTHER INFORMATION: Xaa is nitroarginine
<220> FEATURE:
<221> NAME/KEY: MOD_RES
<222> LOCATION: (12)..(12)
<223> OTHER INFORMATION: AMIDATION

<400> SEQUENCE: 61

Ala Ser Xaa Leu Arg Lys Leu Xaa Lys Xaa Leu Leu
1               5                   10
```

```
<210> SEQ ID NO 62
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (10)..(10)
<223> OTHER INFORMATION: Xaa is homoarginine
<220> FEATURE:
<221> NAME/KEY: MOD_RES
<222> LOCATION: (12)..(12)
<223> OTHER INFORMATION: AMIDATION

<400> SEQUENCE: 62

Ala Ser Xaa Leu Arg Lys Leu Xaa Lys Xaa Leu Leu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (10)..(10)
<223> OTHER INFORMATION: Xaa is dimethyl arginine
<220> FEATURE:
<221> NAME/KEY: MOD_RES
<222> LOCATION: (12)..(12)
<223> OTHER INFORMATION: AMIDATION

<400> SEQUENCE: 63

Ala Ser Xaa Leu Arg Lys Leu Xaa Lys Xaa Leu Leu
1               5                   10

<210> SEQ ID NO 64
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
```

<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 64

Ala Ser Xaa Leu Arg Lys Leu Xaa Ala Arg Leu Leu
1               5                   10

<210> SEQ ID NO 65
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (9)..(9)
<223> OTHER INFORMATION: Xaa is acetyl lysine
<220> FEATURE:
<221> NAME/KEY: MOD_RES
<222> LOCATION: (12)..(12)
<223> OTHER INFORMATION: AMIDATION

<400> SEQUENCE: 65

Ala Ser Xaa Leu Arg Lys Leu Xaa Xaa Arg Leu Leu
1               5                   10

<210> SEQ ID NO 66
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (9)..(9)
<223> OTHER INFORMATION: Xaa is azalysine
<220> FEATURE:
<221> NAME/KEY: MOD_RES
<222> LOCATION: (12)..(12)
<223> OTHER INFORMATION: AMIDATION

<400> SEQUENCE: 66

Ala Ser Xaa Leu Arg Lys Leu Xaa Xaa Arg Leu Leu
1               5                   10

<210> SEQ ID NO 67
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 67

Ala Ser His Xaa Arg Lys Leu Xaa Lys Arg Leu Leu
1               5                   10

<210> SEQ ID NO 68
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION, Nle

<400> SEQUENCE: 68

Ala Ser Xaa Leu Arg Lys Leu Xaa Lys Arg Leu Xaa
1               5                   10

<210> SEQ ID NO 69
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES

```
<222> LOCATION: (8)..(8)
<223> OTHER INFORMATION: Aib
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: AMIDATION

<400> SEQUENCE: 69

Ala Ser Xaa Leu Arg Lys Leu Xaa Lys Arg Xaa Leu
1               5                   10

<210> SEQ ID NO 70
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: AMIDATION, Nle

<400> SEQUENCE: 70

Ala Ser Xaa Leu Arg Lys Leu Xaa Lys Arg Xaa Xaa
1               5                   10

<210> SEQ ID NO 71
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (10)..(10)
<223> OTHER INFORMATION: Orn
<220> FEATURE:
<221> NAME/KEY: MOD_RES
<222> LOCATION: (12)..(12)
<223> OTHER INFORMATION: AMIDATION, Nle

<400> SEQUENCE: 71
```

```
Ala Ser Xaa Leu Arg Lys Leu Xaa Lys Xaa Leu Xaa
1               5                   10
```

<210> SEQ ID NO 72
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (10)..(10)
<223> OTHER INFORMATION: Orn
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: AMIDATION

<400> SEQUENCE: 72

```
Ala Ser Xaa Leu Arg Lys Leu Xaa Lys Xaa Xaa Leu
1               5                   10
```

<210> SEQ ID NO 73
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (10)..(10)
<223> OTHER INFORMATION: Orn
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: AMIDATION, Nle

<400> SEQUENCE: 73

```
Ala Ser Xaa Leu Arg Lys Leu Xaa Lys Xaa Xaa Xaa
1               5                   10
```

<210> SEQ ID NO 74

```
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (10)..(10)
<223> OTHER INFORMATION: Xaa is homoarginine
<220> FEATURE:
<221> NAME/KEY: MOD_RES
<222> LOCATION: (12)..(12)
<223> OTHER INFORMATION: AMIDATION, Nle

<400> SEQUENCE: 74

Ala Ser Xaa Leu Arg Lys Leu Xaa Lys Xaa Leu Xaa
1               5                   10

<210> SEQ ID NO 75
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (10)..(10)
<223> OTHER INFORMATION: Xaa is homoarginine
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: AMIDATION

<400> SEQUENCE: 75

Ala Ser Xaa Leu Arg Lys Leu Xaa Lys Xaa Xaa Leu
1               5                   10

<210> SEQ ID NO 76
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
```

-continued

```
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (10)..(10)
<223> OTHER INFORMATION: Xaa is homoarginine
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: AMIDATION, Nle

<400> SEQUENCE: 76

Ala Ser Xaa Leu Arg Lys Leu Xaa Lys Xaa Xaa Xaa
1               5                   10

<210> SEQ ID NO 77
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION

<400> SEQUENCE: 77

Ala Ser Xaa Leu Xaa Lys Leu Xaa Lys Arg Leu Leu
1               5                   10

<210> SEQ ID NO 78
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: Orn
<220> FEATURE:
```

```
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (10)..(10)
<223> OTHER INFORMATION: Orn
<220> FEATURE:
<221> NAME/KEY: MOD_RES
<222> LOCATION: (12)..(12)
<223> OTHER INFORMATION: AMIDATION

<400> SEQUENCE: 78

Ala Ser Xaa Leu Xaa Lys Leu Xaa Lys Xaa Leu Leu
1               5                   10

<210> SEQ ID NO 79
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: AMIDATION, Nle

<400> SEQUENCE: 79

Ala Ser Xaa Leu Xaa Lys Leu Xaa Lys Arg Leu Xaa
1               5                   10

<210> SEQ ID NO 80
<211> LENGTH: 13
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: Nle
<220> FEATURE:
<221> NAME/KEY: MOD_RES
```

<222> LOCATION: (13)..(13)
<223> OTHER INFORMATION: AMIDATION, Nle

<400> SEQUENCE: 80

Ala Ser Xaa Leu Xaa Lys Leu Xaa Lys Arg Leu Xaa Xaa
1               5                   10

<210> SEQ ID NO 81
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (10)..(10)
<223> OTHER INFORMATION: Orn
<220> FEATURE:
<221> NAME/KEY: MOD_RES
<222> LOCATION: (12)..(12)
<223> OTHER INFORMATION: AMIDATION, Nle

<400> SEQUENCE: 81

Ala Ser Xaa Leu Xaa Lys Leu Xaa Lys Xaa Leu Xaa
1               5                   10

<210> SEQ ID NO 82
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (10)..(10)
<223> OTHER INFORMATION: Orn
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)

<223> OTHER INFORMATION: AMIDATION, Nle

<400> SEQUENCE: 82

Ala Ser Xaa Leu Xaa Lys Leu Xaa Lys Xaa Xaa Xaa
1               5                   10

<210> SEQ ID NO 83
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 83

Ala Ser His Leu Arg Lys Leu Arg Lys Arg Leu Leu
1               5                   10

<210> SEQ ID NO 84
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 84

Ala Ser His Cys Arg Lys Leu Cys Lys Arg Leu Leu
1               5                   10

<210> SEQ ID NO 85
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 85

Ala Ser Cys Leu Arg Lys Leu Cys Lys Arg Leu Leu
1               5                   10

<210> SEQ ID NO 86
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES

```
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 86

Cys Ser His Leu Arg Lys Leu Cys Lys Arg Leu Leu
1               5                   10

<210> SEQ ID NO 87
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 87

Ala Ser His Leu Arg Lys Cys Arg Lys Arg Cys Leu
1               5                   10

<210> SEQ ID NO 88
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 88

Ala Ser His Cys Arg Lys Leu Arg Lys Arg Cys Leu
1               5                   10

<210> SEQ ID NO 89
<211> LENGTH: 6
<212> TYPE: PRT
<213> ORGANISM: Artificial Sequence
<220> FEATURE:
<223> OTHER INFORMATION: c-myc regulatory motif
<220> FEATURE:
<221> NAME/KEY: MISC_FEATURE
<222> LOCATION: (1)..(1)
<223> OTHER INFORMATION: Xaa may be serine or threonine
<220> FEATURE:
<221> NAME/KEY: MISC_FEATURE
<222> LOCATION: (2)..(2)
<223> OTHER INFORMATION: Xaa may be any amino acid
<220> FEATURE:
<221> NAME/KEY: MISC_FEATURE
<222> LOCATION: (5)..(5)
<223> OTHER INFORMATION: Xaa may be serine or threonine

<400> SEQUENCE: 89

Xaa Xaa Ser Ser Xaa Pro
1               5
```

```
<210> SEQ ID NO 90
<211> LENGTH: 21
<212> TYPE: PRT
<213> ORGANISM: Artificial Sequence
<220> FEATURE:
<223> OTHER INFORMATION: ApoE mimetic peptide

<400> SEQUENCE: 90

Trp Lys Lys Cys Leu Arg Val Arg Leu Ala Ser His Leu Arg Lys Leu
1               5                   10                  15

Arg Lys Arg Leu Leu
            20
```